United States Patent [19]

Wissner et al.

[11] 4,245,121

[45] Jan. 13, 1981

[54] PROSTENOIC ACIDS AND ESTERS

[75] Inventors: Allan Wissner, Monsey, N.Y.; Martin J. Weiss, Oradell; Karel F. Bernady, South Summerville, both of N.J.

[73] Assignee: American Cyanamid Company, Stamford, Conn.

[21] Appl. No.: 118,276

[22] Filed: Feb. 4, 1980

Related U.S. Application Data

[62] Division of Ser. No. 783,033, Mar. 30, 1977, Pat. No. 4,197,407.

[51] Int. Cl.³ .................................... C07C 177/00
[52] U.S. Cl. .................................... 562/500; 556/441; 556/412; 260/410.9 R; 260/413; 560/118; 560/231
[58] Field of Search ............... 560/118, 231; 502/500, 502/410.9 R, 413; 556/441, 442

[56] References Cited

U.S. PATENT DOCUMENTS 4,132,738   1/1979   Kluender .................... 260/586

*Primary Examiner*—Robert Gerstl
*Attorney, Agent, or Firm*—Richard J. Hammond

[57] ABSTRACT

This disclosure describes derivatives, analogs, and congeners of prostanoic acid having a terminal cyclic moiety in the $\beta$-chain which possess the pharmacological activities associated with the prostaglandins.

20 Claims, No Drawings

PROSTENOIC ACIDS AND ESTERS

This is a division, of application Ser. No. 783,033, filed Mar. 30, 1977, now U.S. Pat. No. 4,197,407.

BACKGROUND OF THE INVENTION

Applicants are now aware of any prior art reference which, in their respective judgments as one skilled in the prostaglandin art, would anticipate or render obvious the novel compounds of the instant invention; however, for the purpose of fully developing the background of the invention and establishing the state of the requisite art, the following references are set forth: U.S. Pat. No. 3,884,969; Japanese Pat. No. 3,884,969; German Offen. No. 2,515,770; German Offen. No. 2,510,818; and Netherlands published Patent Application No. 7,410-185.

BRIEF SUMMARY OF THE INVENTION

This invention relates to novel prostenoic acids and esters of the formula:

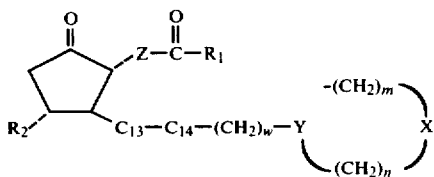

wherein $R_1$ is selected from the group consisting of hydroxy, triloweralkylsilyloxy ($C_1$ to $C_4$) and straight or branched chain alkoxy ($C_1$ to $C_6$); $R_2$ is selected from the group consisting of hydrogen, hydroxy, triloweralkylsilyloxy ($C_1$ to $C_4$), and alkanoyloxy ($C_2$ to $C_5$); Y is a trivalent radical selected from the group consisting of

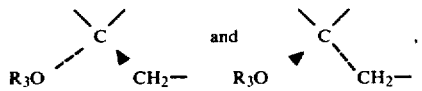

wherein $R_3$ is selected from the group consisting of hydrogen, triloweralkylsilyl and alkanoyl ($C_2$ to $C_5$); X is a divalent radical selected from the group consisting of

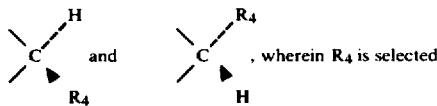, wherein $R_4$ is selected from the group consisting of a branched or straight chain alkyl group ($C_1$ to $C_7$), hydrogen, phenoxy and phenoxy substituted with a compound selected from the group consisting of halogen, trifluoromethyl, and methoxy; n is zero or an integer from 1 to 4; m is zero or an integer from 1 to 4; the sum of n and m has the value of 2 to 4; the moiety $C_{13}$–$C_{14}$ is ethylene or trans vinylene; w is 1 or zero; and Z is a divalent radical selected from the group consisting of

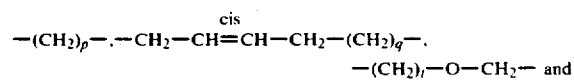

$-(CH_2)_t-O-CH_2-$ and
$-(CH_2)_t-S-CH_2-$ wherein p is an integer from 5 to 7, q is an integer from 1 to 3, and t is an integer from 3 to 5.

Also claimed in this invention are 11,15-bis-deoxy PGE compounds of the formula:

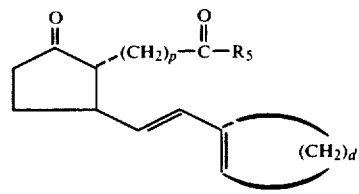

wherein p is an integer from 5 to 7; d is an integer from 3 to 5; and $R_5$ is selected from the group consisting of hydroxyl and $C_1$-$C_3$ alkoxy.

DETAILED DESCRIPTION OF THE INVENTION

Useful pharmacologically acceptable salts of the above formula wherein $R_1$ is hydroxy are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

The compounds of this invention are administered in various ways for various purposes, e.g., intravenously, intramuscularly, subcutaneously, orally, intravaginally, rectally, bucally, sublingually, topically and in the form of sterile implants for prolonged action.

For intravenous injection or infusion, sterile aqueous isotonic solutions are preferred. For that purpose, it is preferred because of increased water solubility that $R_1$ be hydrogen or a pharmacologically acceptable cation. For subcutaneous or intramuscular injection, sterile solutions or suspensions of the acid, salt, or ester formed in aqueous or non-aqueous media are used. Tablets, capsules, and liquid preparation such as syrups, elixirs, and simple solutions, with the usual pharmaceutical carriers are used for oral or sublingual administration. For rectal or vaginal administration, suppositories prepared as known in the art are used. For tissue implants, a sterile tablet or silicone rubber capsule or other object containing or impregnated with the substance is used. On certain occasions it may be advantageous to administer the compounds of this invention as clathrate compounds with substances such as α-cyclodextrin.

The prostaglandins are a family of closely related compounds which have been obtained from various animal tissues and which stimulate smooth muscle, lower arterial blood pressure, antagonize epinephrine-induced mobilization of free fatty acids, and have other pharmacological and autopharmacological effects in mammals. See Bergstom, et al., J. Biol. Chem., 238, 3555 (1963) and Horton, Experientia, 21, 113 (1965) and references cited therein. All of the so-called natural prostaglandins are derivatives of prostanoic acid:

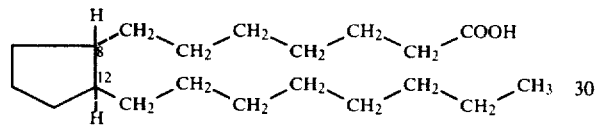

The hydrogen atoms attached to C-8 and C-12 are in trans-configuration. The natural prostaglandins represent only one of the possible optical isomers. The compounds of this invention include all possible optical isomers.

The compounds of this invention which have the structure as shown in formula (A) wherein $R_1$, Z, $R_2$, Y, m, n, w and X are as herein above defined are said to be in the same configuration as the natural prostaglandins with respect to the configurations at $C_8$, $C_{11}$ and $C_{12}$ and are designated by the prefix nat. The enantiomer, represented by formula (B) is said to be in the mirror image or ent configuration. A substituent at $C_{11}$ drawn with a dotted line ($C_{11}$ - - - $R_2$) is said to have an α configuration; a solid line ($C_{11}$—$R_2$) indicates a β configuration. The configuration at Y and X will be expressed in terms of R and S as is understood in the art.

For example, the compound represented by formula (C) is named: nat-15S,16S-11α,15-dihydroxy-9-oxo-15,16-trimethylene-13-trans-prostenoic acid; its enantiomer (Formula D) is named ent-15R,16R-11α,15-dihydroxy-9-oxo-15,16-trimethylene-13-trans-prostenoic acid. The racemate [1:1 mixture of (C) and (D)] is named nat-15S,16S-(and ent-15R,16R)11α,15-dihydroxy-9-oxo-15,16-trimethylene-13-trans-prostenoic acid. In a similar manner, the compounds represented by formulae (E) to (J) have the configurations shown below.

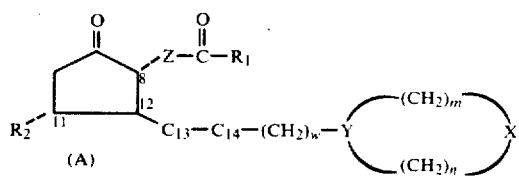

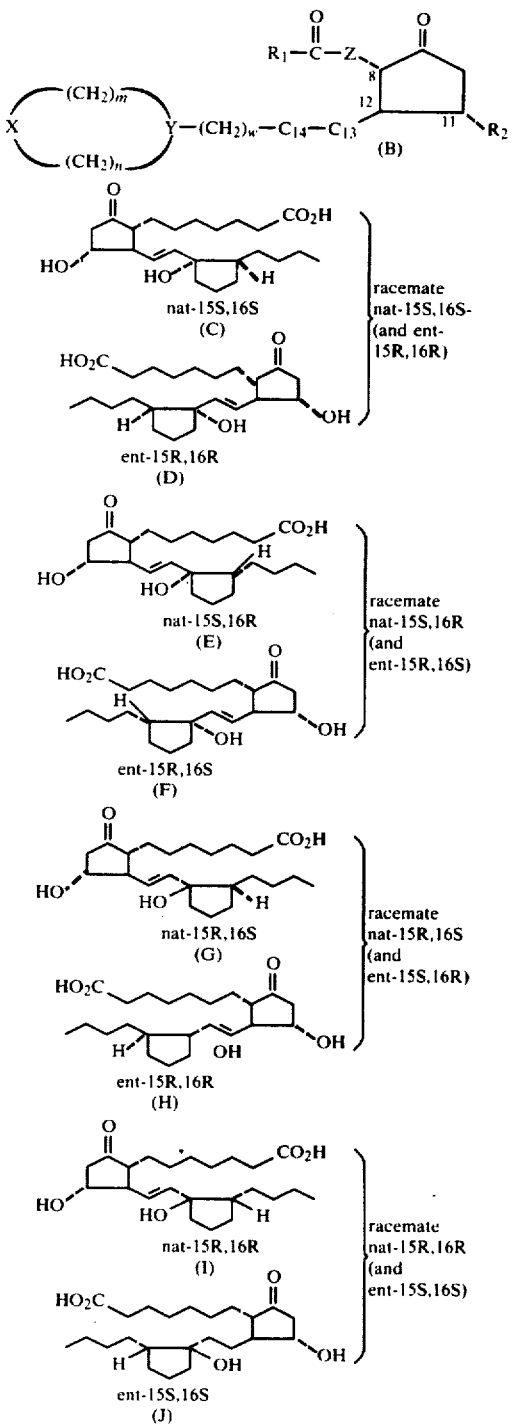

In each of the above formulae (C to J) the hydroxy group at $C_{11}$ is named "-11α-hydroxy".

The novel compounds of this invention can be prepared by the reaction sequences illustrated in Flowsheet A below, wherein n, m, X, w, and Z are as hereinabove defined; $R_1'$ is straight or branched-chain alkoxy ($C_1$ to $C_{12}$) or triloweralkylsilyloxy ($C_1$ to $C_4$); $R_2'$ is hydrogen, triloweralkylsilyloxy ($C_1$-$C_4$) or alkanoyloxy ($C_2$ to $C_5$); $R_1''$ and $R_2''$ are hydroxy.

Flowsheet A
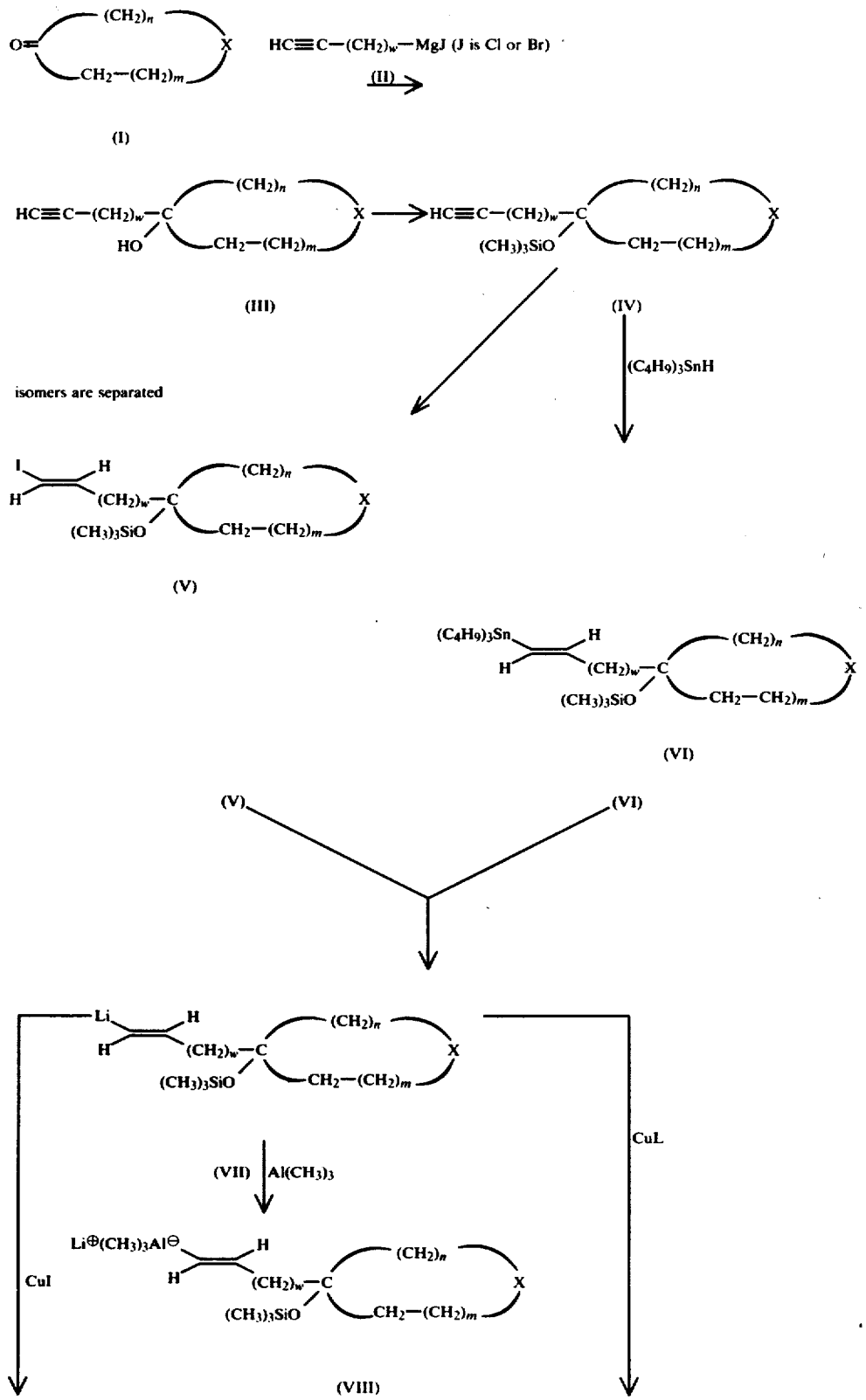

-continued
Flowsheet A

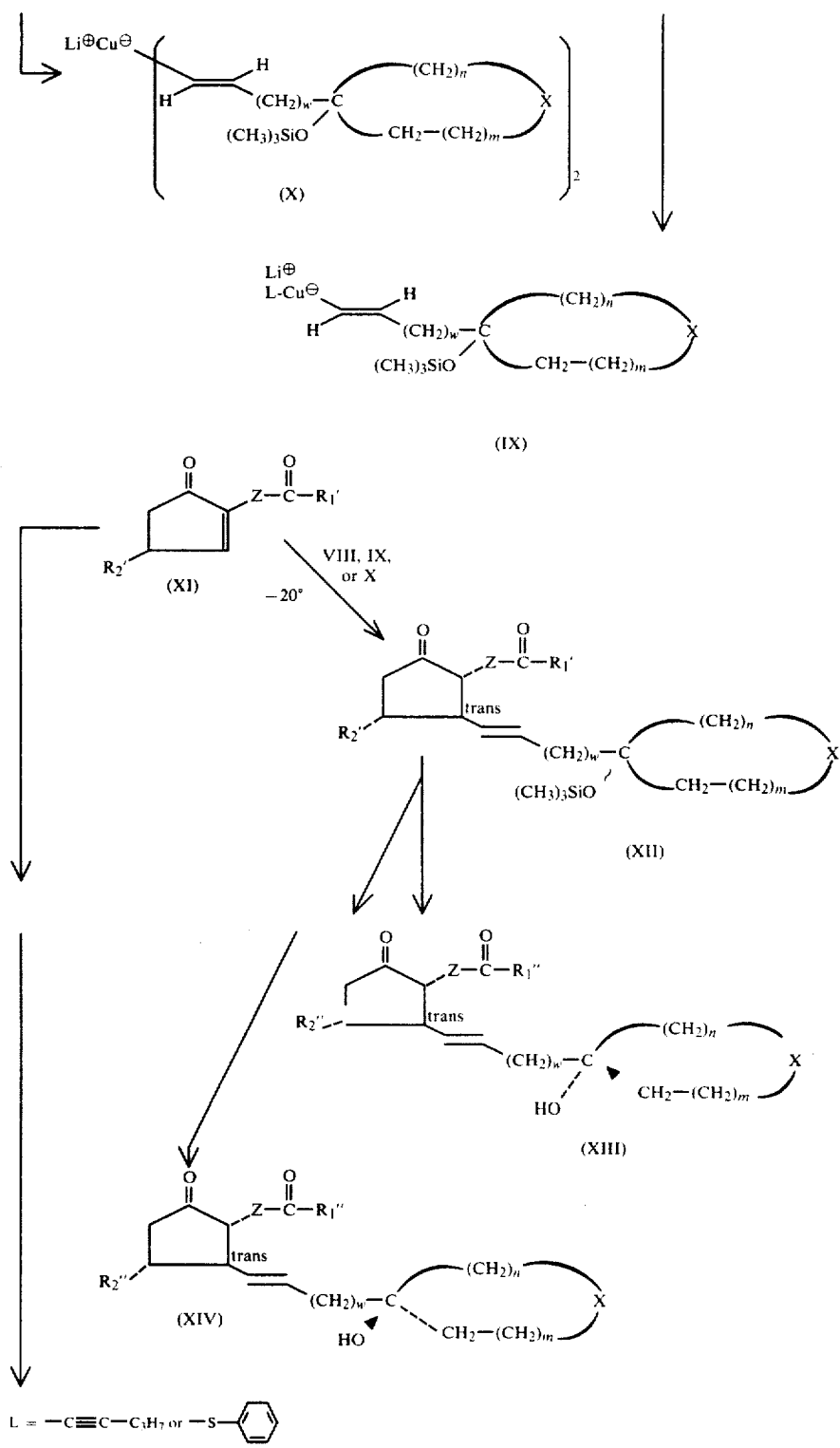

In accordance with the scheme as outlined hereinabove in Flowsheet A a ketone (I) is reacted with a Grignard reagent (II) such as acetylene magnesium chloride (II, w=0) or propargyl magnesium bromide (II, w=1) to give the acetylenic alcohols (III). In those cases where X is not —CH$_2$— two isomeric acetylenic alcohols are formed. These isomers can be separated by procedures well known to the art including fractional crystallization, fractional distillation and various chromatographic procedures. The individual isomers can then be carried through the remaining reactions outlined in Flow-sheet A.

The acetylenic alcohol (III) is converted to its trimethylsilyl ether in the usual manner. The silylated derivative (IV) is then treated with diisoamylborane (prepared in situ in tetrahydrofuran solution at ice bath temperatures from 2-methyl-2-butene, sodium borohydride and boron trifluoride ethereate) and then anhydrous trimethylamine oxide. The resulting solution and an iodine solution in tetrahydrofuran are then added simultaneously to an aqueous solution of sodium hydroxide to give the 1-iodo-3-trimethylsilyloxy-trans-1-alkene (V).

The vinyl iodide (V) is converted to the trans-vinyl lithium derivative (VII) with clean retention of configuration by treatment at about −78° C. in hexane or toluene solution with either one equivalent of n-butyl lithium or two equivalents of t-butyl lithium. It is preferable for this treatment to proceed for about one hour at −78° C., then for about one hour at −40° C. and finally for about one hour at about 0° C. For the subsequent preparation of lithio alanate reagents (VIII) it is preferable to use n-butyl lithium, and for the lithio cuprate reagents (IX) or (X) t-butyl lithium is the agent of choice. The same vinyl lithium derivative (VII) can be prepared from the 1-tri-n-butylstannyl 3-trimethylsilyloxy-trans-alkene (VI) by treatment of (VI) with n-butyl lithium in hexane solution at −40° to 0° C. (VI) in turn is readily prepared by the addition of tri-n-butyl tin hydride to the acetylene (IV) in the presence of bisazoisobutyronitrile followed by vacuum distillation at a high enough temperature (about 170° C.) to isomerize any of the cis-vinyl tin compound to the trans-vinyl tin compound.

For the preparation of the alanate reagent (VIII) or the like, a molar equivalent of a tri-lower alkyl (1–5 carbon atoms) aluminum (e.g., trimethyl aluminum), dissolved in a solvent such as hexane, is added to the vinyl lithium derivative (VII) at about 0° C. After about 15–45 minutes at this temperature and requisite blocked cyclopentenone (XI) is added and the reaction mixture is stirred for about 18 hours at ambient temperatures. The mixture is quenched with aqueous hydrochloric acid in the cold and the product is obtained by extraction. In the 11-deoxy series the blocking trialkylsilyl group is removed on treatment with acetic acid: tetrahydrofuran:water (4:2:1) at room temperatures for about twenty minutes. The ester group can then be saponified in the usual manner. In the 11-oxy series, the silyl groups are removed by treatment with acetic acid:-water:tetrahydrofuran (20:10:3) at about 40° C. for about 4 hours. Alkyl esters of the 11-oxy series are not disturbed by this treatment and cannot be saponified by chemical means in view of the instability of the 11-hydroxy-9-ketone to base treatment. However, the ester can be cleaved by treatment with Baker's Yeast, a procedure well-known in the art.

For the preparation of the asymmetrical lithio cuprate (IX) or the like, a solution of one molar equivalent of copper (I)-1-alkyne, preferably copper (I)-1-pentyne, in anhydrous hexamethylphosphorus triamide, preferably three to five molar equivalents, and anhydrous ether is added to one molar equivalent of the aforementioned vinyl lithium (VII) solution cooled to about −78° C. The solution is then stirred for about one hour at −78° C. A cuprate reagent containing a p-thiophenoxide ligand

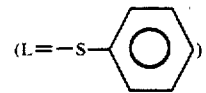

can also be used; it is prepared by first forming lithium thiophenoxide by adding an equivalent of n-butyl lithium in hexane to an etheral solution of thiophenol. To this is then added a solution of one equivalent of tri-n-butyl phosphine copper iodide complex in ether. The resulting solution of phenylthio copper is added at −78° C. under inert gas to the solution of the vinyl lithium compound (VII). The mixture is then maintained at −78° C. for one hour. To either of these cuprate solutions at −78° C. a molar equivalent of the requisite cyclopentenone (XI) is added. After several hours at −20° C. the reaction mixture is quenched with aqueous ammonium chloride solution and the blocked product (XII) is isolated in the usual manner. The deblocking of this product is then carried out in the manner as described hereinabove.

The products are finally purified by chromatographic procedures in the usual manner.

In those cases where X is not $CH_2$ and $m \neq n - 1$, two isomers are formed which differ in the configuration at $C_{15}(w = \theta)$ or $C_{16}(w = 1)$; both isomers are racemates and they can be separated from each other by chromatographic procedures well known in the art. In the 11-deoxy series, this separation can be effected at either the alkyl ester of prostenoic acid stage.

For the preparation of the symmetrical lithio cuprate (X) one molar equivalent of copper (I) iodide tributylphosphine complex, dissolved in anhydrous ether, is added at about −78° C. to two molar equivalents of the aforementioned vinyl lithium (VII) solution in hexanes, cooled to −78° C. After about one hour at this temperature, the lithio cuprate (X) is treated with the requisite cyclopentenone (XI) as described hereinabove for the conjugate addition with the 1-alkynyl lithio cuprate (IX).

In order to ensure a trans-relationship in (XII), (XIV) or (XIII), these products can be submitted to conditions known in the literature to equilibrate cis 8-iso-PGE$_1$ to a mixture containing about 90% of the trans-product [see E. G. Daniels, et al., J. A. C. S., 90, 5894 (1968)]. These conditions involve treatment with potassium acetate in aqueous methanol for about 96 hours at room temperature. The cis and trans products are separable by chromatographic procedures.

Most of the cyclopentenones required for the purposes of this invention have been described in the literature or can be prepared by procedures quite analogous to those already described. Appropriate references are provided in the examples which follow. The synthesis of certain nonreference requisite cyclopentenones is also described therein.

The 13-dihydro derivatives ($C_{13}$–$C_{14}$ is ethylene) of this invention can be prepared by reduction of the $\Delta^{13}$ function in the corresponding 13-prostenoic acids or esters. This reduction can be accomplished by catalytic reduction, preferably at low pressure with a noble metal catalyst in an inert solvent at ambient temperatures.

The prostanoic and prostenoic carboxylic acids of this invention are convertible to the corresponding alkyl esters by treatment with the appropriate diazoalkane in the usual manner. The preparation of diazoalkanes by various procedures are well-described in the art, see for example C. D. Gutsche, *Organic Reactions*, VIII, 389 (1954). Certain of the esters of this invention can also be obtained directly by use of the appropriate cyclopentenone ester (see XI). The various esters can also be prepared by any of several procedures well-known in the art via an acid chloride (prior blocking of free alcohol groups with appropriate blocking groups such as trialkylsilyl, tetrahydropyranyl and the like) or mixed anhydrides and treatment of these intermediates with the appropriate alcohol. Mixed anhydrides can be obtained by treatment of the prostaglandin acid in a solvent such as dioxane at a temperature in the range of 0° C. to 15° C. with a molar equivalent of a tri-alkylamine, preferably triethylamine, tributylamine and the like, and then a molar equivalent of isobutyl chlorocarbonate or the like. The resulting mixed anhydride is then treated with the appropriate alcohol to give the derivatized product. [For a pertinent literature analogy see Prostaglandins, 4, 738 (1973).]

An alternative procedure involves treatment of the prostaglandin acid with a molar equivalent of the trialkyl amine in an excess of the appropriate alcohol in an anhydrous solvent such as methylene chloride, a molar equivalent of p-toluenesulfonyl chloride is then added (if necessary, a second molar equivalent can be added) and after stirring at ambient temperatures for about 15 minutes to one hour the product is worked-up in the usual manner. (For a pertinent literature analogy see U.S. Pat. No. 3,821,279, June 28, 1974). A third procedure involves use of dicyclohexylcarbodiimide in the usual manner; for a pertinent literature analogy see German Offen. 2,365,205 (July 11, 1974); Chem. Abst., 81, 120098 g. (1974).

The esterified alcohol derivatives ($R_2$ is alkanoyloxy and/or $R_3$ is alkanoyl) are also prepared in the usual manner by procedures well-known in the art form the appropriate alkanoic acid anhydride or acid chloride.

Certain of the ketones (I) of this invention are prepared as indicated in Flowsheet B below:

Flowsheet B

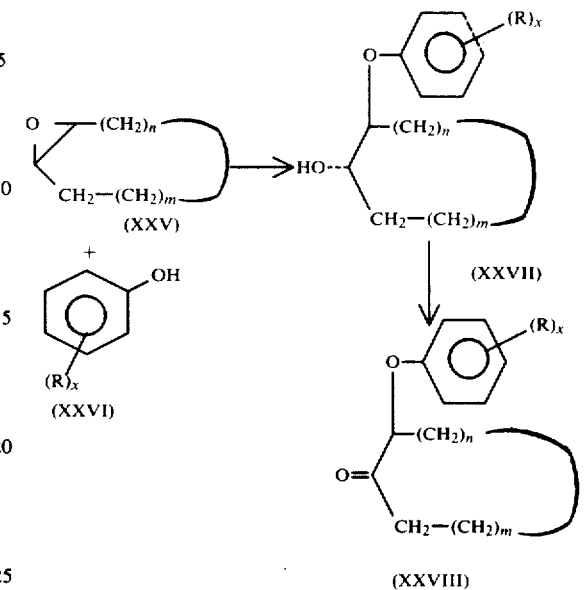

(XXVIII)

wherein n and m are as hereinabove defined and the moiety

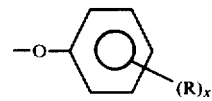

represents a phenoxy group which is optionally substituted with one or more halogen, trifluoromethyl, and lower alkyloxy ($C_1$ to $C_4$) groups.

As indicated in Flowsheet B the reaction of an epoxide (XXV) with a substituted or unsubstituted phenol (XXVI) in the presence of a catalytic amount of aqueous sodium hydroxide and a phase transfer catalyst such as methyl tricapryly ammonium chloride and the like at 70°-80° C. gives the phenoxy substituted alcohol (XXVII) which in turn is oxidized with an oxidizing reagent such as pyridinium chlorochromate in methylene chloride to give the phenoxy substituted ketone (XXVIII).

The other ketones (I) used in this invention are known in the literature or can be made by procedures well known to the art [G. Lardelli, U. Lamberti, W. T. Walles and A. P. de Jonge, *Rec. Trav. Chem. Pays-Bas,* 86 481 (1967); Ng. Ph. Buu-Hoi, T. B. Loc and Ng. Dat Xuong., Bull. Soc. *Chem. France* 174 (1958); and G. H. Posner, *Organic Reactions,* 19, 1 (1972)].

Compounds of the formulae (XXIX) and (XXX) are prepared by heating (100°-200° C.) the corresponding 15-hydroxy compounds resulting in dehydration.

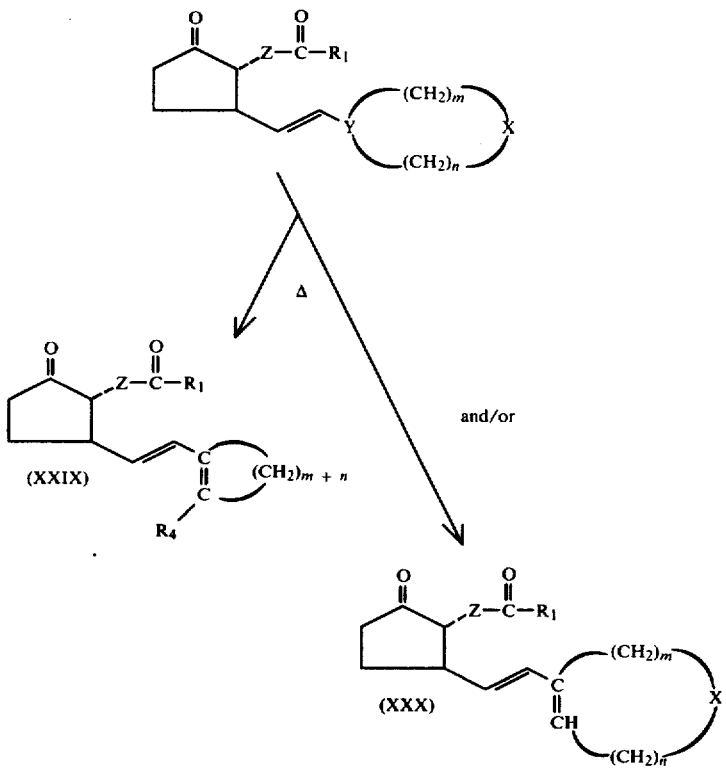

Also embraced within the scope of this invention are the various intermediates, the use of which is described herein. These are represented by the following generic formulae (K) and (L).

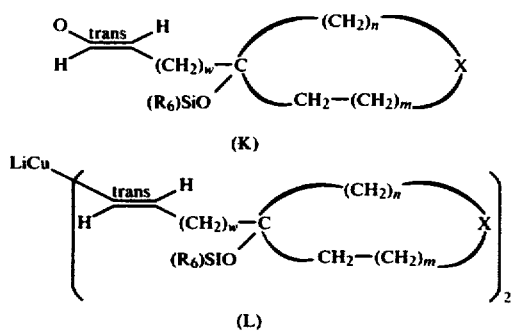

Wherein w, n, m and X are as hereinabove defined; $R_6$ is lower alkyl ($C_1$ to $C_6$); Q is iodine, triloweralkyl ($C_1-C_6$) tin, lithium,

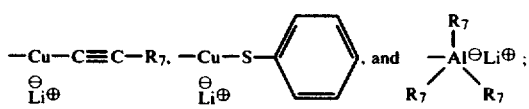

$R_7$ is lower alkyl ($C_1-C_7$).

When the compounds of this invention are prepared from racemic starting compounds two racemates are obtained. In appropriate instances these racemates can be separated from each other by careful application of the usual chromatographic procedures. In the more difficult instances it may be necessary to apply high pressure liquid chromatography including recycling techniques. [See G. Fallick, *American Laboratory*, 19–27 (August, 1973) as well as references cited therein. Additional information concerning high speed liquid chromatography and the instruments necessary for its application is available from Waters Associate, Inc., Maple Street, Milford, Mass.]

It is also possible to prepare the individual enantiomers in the 11-oxy series via the conjugate addition procedure discussed above by starting with a resolved 4-oxycyclopentenone [see (XI), $R_2'$ is tri-loweralkylsilyloxy]. The resulting products (XIV) and (XIII) after deblocking as described hereinabove are obtained in their optically active forms.

The 4-hydroxycyclopentenone racemates may be resolved into their component enantiomers (XXXI) and (XXXII) by derivatizing the ketone function with a reagent having an optically active center. The resulting diastereomeric mixture can then be separated by fractional crystallization, or by chromatography, or by high speed liquid chromatography involving, if necessary, recycling techniques. Among the useful optically active ketone derivatizing reagents are 1-α-aminoxy-γ-methylpentanoic acid hydrochloride [to give (XXXIII)], (R)-2-aminoxy-3,3-dimethylbutyric acid hydrochloride, and 4-α-methylbenzyl semicarbazide. After separation of the diastereomeric derivatives, reconstitution of the keto function provides the individual 4-hydroxycyclopentenone enantiomers (XXXI) and (XXXII). A useful procedure for the resolution of a 4-hydroxycyclopentenone racemate via an oxime such as (XXXIII) is described in the art [R. Pappo, P. Collins and C. Jung, *Tetrahedron Letters*, 943 (1973)].

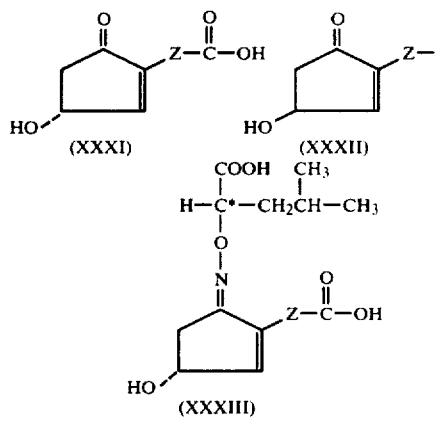

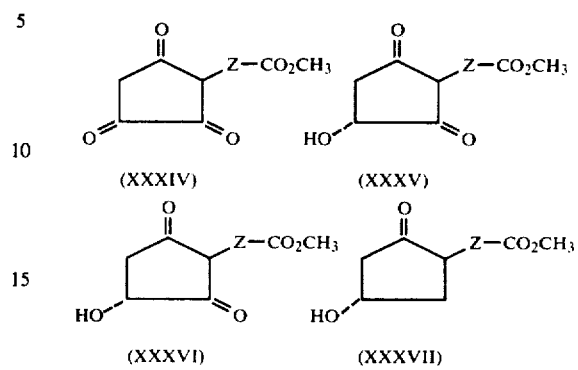

An alternative procedure for the preparation of the 4(R)-hydroxycyclopentenone enantiomers such as (XXXI) involves as a key step the selective microbiological or chemical reduction of trione (XXXIV) to the 4(R)-hydroxycyclopentanedione (XXXV). A wide variety of microorganisms are capable of accomplishing this asymmetric reduction, one of the most useful being *Dipodascus uninicleatus*. This step also can be achieved chemically by catalytic hydrogenation in the usual manner (for example, under about one atmosphere of hydrogen in methanol) using a soluble rhodium catalyst with chiral phosphine ligands, such as (1,5-cyclooctadiene)-bis-(o-anisylcyclohexylmethylphosphine)rhodium (I) tetrafluoroborate in the presence of one equivalent of organic base, such as triethylamine.

Conversion of hydroxycyclopentanedione (XXXV) to an enol ether or enol ester, (XXXVI, E=alkyl, preferably iso-propyl; aroyl such as benzoyl; or arylsulfonyl such as 2-mesitylenesulfonyl), is accomplished by treatment, for example, with isopropyl iodide and a base such as potassium carbonate in refluxing acetone for from 15 to 20 hours, or with a base such as triethylamine and 0.95 equivalents of benzoyl chloride or a slight excess of 2-mesitylenesulfonyl chloride, in a non-protropic solvent at a temperature of about $-10°$ to $-15°$ C. Reduction of (XXXVI) with excess sodium bis(2-methoxyethoxy)aluminum hydride in a solvent such as tetrahydrofuran or toluene at low temperatures, such as $-60°$ to $-78°$ C., followed by mild acid hydrolysis (representative conditions: aqueous dilute hydrochloric acid, pH 2.5; or oxalic acid, sodium oxalate in chloroform) at ambient temperatures from 1 to 3 hours provides the 4(R)-hydroxycyclopentenone ester (XXXVII). The ester (XXXVII), after blocking the hydroxy function as described hereinabove, can be subjected to conjugate addition reactions also as described hereinabove. The conjugate addition product, after deblocking the 11- and 15-hydroxy groups, will then be a methyl ester which can be hydrolyzed to the corresponding carboxylic acid by enzymatic or microbiological procedures, for example with baker's yeast or by exposure to *Rhizopus oryzae*.

For a description of these procedures in the art see: C. J. Sih, et al, J. A. C. S., 95, 1676 (1973); J. B. Heather, et al., *Tetrahedron Letters*, 2213 (1973); R. Pappo and P. W. Collins, *Tetrahedron Letters*, 2627 (1972); and R. Pappo, P. Collins, and C. Jung, Ann. N.Y. Acad. Sci., 180, 64 (1971). For a description of the baker's yeast procedure see C. J. Sih, et al., J. A. C. S., 94, 3643 (1972).

Procedures for the preparation of the requisite cyclopentanetriones (XXXIV) are well-established in the art and generally involve the treatment of an $-1$ oxo long chain ester (XXXVIII) with methyl or ethyl oxalate and a base such as sodium methoxide in methanol, followed by treatment with dilute hydrochloric acid in aqueous methanol to effect the dealkoxalylation of the intermediate (XXXIX). See J. Kutsube and M. Matsui, *Agr. Biol. Chem.*, 33 1078 (1969); P. Collins, C. J. Jung and R. Pappo, *Israel Journal of Chemistry*, 6, 839 (1968); R. Pappo, P. Collins and C. Jung, Ann. N.Y. Acad. Sci., 180, 64 (1971); C. J. Sih, et al., J. A. C. S., 95, 1676 (1973) (see reference 7); and J. B. Heather, et al., *Tetrahedron Letters*, 2313 (1973) for pertinent background literature.

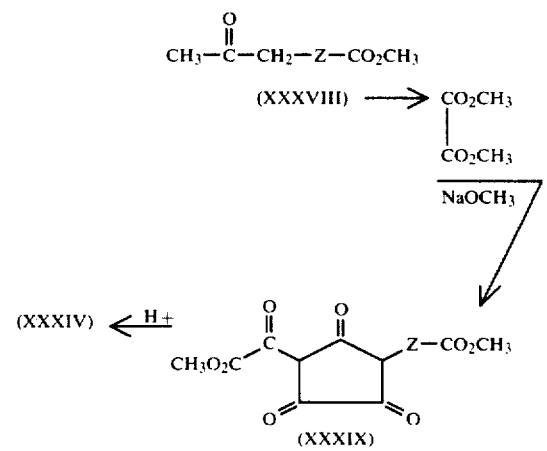

The intermediate keto esters (XXXVIII) may be prepared by a variety of methods known to the art. One useful procedure is outlined below and involves alkylation of ethyl acetoacetate sodium salt (XL) in the usual manner with the appropriate side-chain precursor (XLI, X=Cl, Br, I, preferably Br or I) followed by decarbethoxylation and reesterification, all in the usual manner.

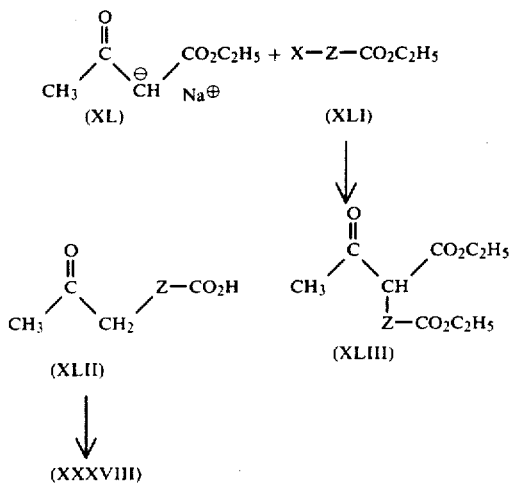

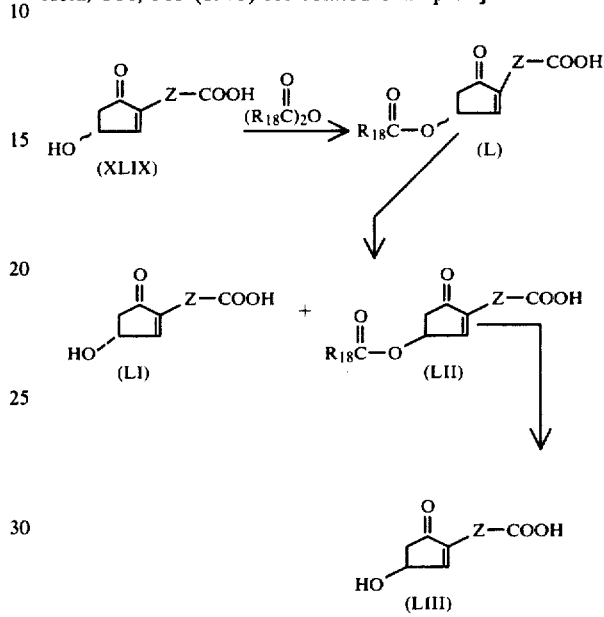

The side-chain precursors (XLI) are commercially available where Z is —$(CH_2)_p$—, and can be prepared as described in Belgian Pat. No. 786,215 (granted and opened to inspection Jan. 15, 1973).

Those precursors wherein Z is —$(CH_2)_t$—O—$CH_2$— can be prepared by the transformations shown directly below starting with the mono-tetrahydropyranyl derivative (XLIV). Thus, (XLIV) is converted to the lithium alcoholate by treatment with butyl lithium, the alcoholate is then O-alkylated with ethyl bromoacetate to provide (XLV), which on de-O-tetrahydropyranylation, mesylation and reaction with lithium bromide gives the required (XLVI). (These and all the above-described transformations can be effected in the usual manner, well-established in the art; pertinent examples for most of the reactions can be found in the above-cited Belgian patent 786,215.)

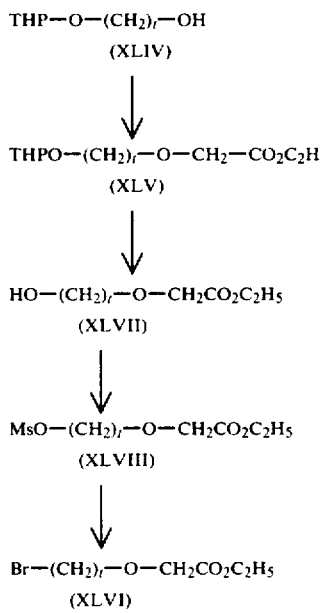

It is also possible to resolve the 4-hydroxycyclopentenone racemate (XLIX) by microbiological means. Thus, treatment of the 4-O-alkanoyl or aroyl derivatives (L, $R_{18}$=aryl or alkyl) of racemate (XLIX) (preferably the 4-O-acetyl and 4-O-propionyl derivatives) with an appropriate microorganism, preferably a Saccharomyces species e.g., 1375-143, affords preferential de-O-acylation of the 4(R)-enantiomer to give (LI), which is then separated from the unreacted 4(S)-O-acyl enantiomer (LII) by chromatographic procedures. After separation, mild hydrolysis of the 4(S) derivative (LII) provides the 4(S)-hydroxycyclopentenone (LIII). [See N. J. Marsheck and M. Miyano, *Biochima et Biophysica Acta*, 316, 363 (1973) for related examples.]

It is also possible to prepare the individual 4-hydroxycyclopentenones (LI) and (LIII) directly by selective microbial hydroxylations of the corresponding 4-unsubstituted cyclopentenone (LIV). For example, with *Aspergillus niger* ATCC 9142; a selective 4(R)-hydroxylation of [LIV, Z=$(CH_2)_6$] has been reported; see S. Kurozumi, T. Tora and S. Ishimoto, *Tetrahedron Letters*, 4959 (1973). Other microorganisms can also accomplish this hydroxylation.

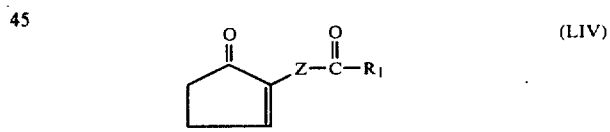

An alternative resolution procedure involves derivatization of the alcohol function of the racemic hydroxycyclopentenone to give ester-acid derivatives such as (LV) wherein $R_1''$ is hydrogen or an alkoxy group, n' is zero or two and Z is as hereinabove defined.

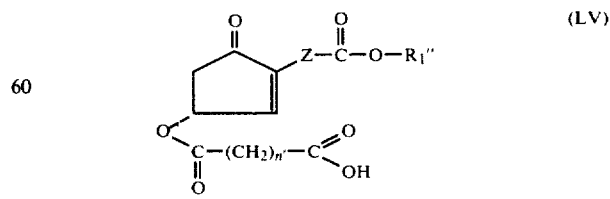

Such derivatives may be obtained from the corresponding free hydroxycyclopentenone by treatment in the usual manner with oxalyl chloride, succinyl chloride, succinic anhydride and the like. Treatment of the resulting acid or diacid ($R_1'' = $hydrogen) with optically active amines e.g., 1-(−)-α-methylbenzylamine, d-(+)-α-methylbenzylamine, brucine, dehydroabietylamine, strychnine, quinine, cinchonine, quinidine ephedrine, (+)-α-amino-1-butanol and the like, and fractional recrystallization of the resulting diastereomeric mixtures followed by cleavage of the 4-oxy ester function in each of the individually isolated diastereomers provides the individual 4(R)- and 4(S)-hydroxycyclopentenone enantiomers (LVI) and (LVII) or their respective esters. Cleavage of the oxalate acid ester (LV, n=0) can be accomplished by treatment with lead tetraacetate in pyridine solution. For an example of a similar use of oxalate acid-esters see J. G. Molotkovsky and L. D. Bergelson, *Tetrahedron Letters*, 4791 (No. 50, 1971); For an example of the use of a succinate acid-ester see B. Goffinet, Ger. Offen. 2,263,880; *Chem. Abstracts*, 79, 7815$z$ (1973).

Resolution of a 9-hydroxy racemate (the component enantiomers are illustrated by LVIII and LIX below) may be accomplished by conversion of the racemate, wherein the $C_{11}$ and $C_{15}$ or $C_{16}$ hydroxy functions have been preferentially blocked by trialkylsilyl groups, (for example, by first derivatizing the two hydroxy functions in the corresponding 9-oxo derivative and then reducing the 9-carbonyl as described hereinabove), to the corresponding phthalate half acid-ester, deblocking the $C_{11}$ and $C_{15}$ hydroxy functions and conversion of the diacid (e.g., LX) to a mixture of diastereomeric bis salts (e.g., LXI) with an optically active amine (e.g., 1-(−)-α-methylbenzylamine, D-(+)-α-methylbenzylamine, brucine, dehydroabietylamine, strychnine, quinine, cinchonine, cinchonidine, quinidine, ephedrine, deoxyephedrine, amphetamine, (+)-2-amino-1-butanol, (−)-2-amino-1-butanol and the like). The resulting diastereomers are then separated by fractional crystallization and the individual components are then converted by acidification and saponification to the individual optically active parent 9α-hydroxy enantiomers (LVIII) and (LIX), oxidation of which, after preferential blocking of the $C_{11}$ and $C_{15}$ hydroxy functions with tetrahydropyranyl or trialkylsilyl groups, provides, after deblocking, the corresponding individual 9-oxo enantiomers (LXII) and (LXIII). If necessary, the 11- and 15-hydroxy groups can be converted to tetrahydropyranyloxy groups prior to saponification of the phthalate ester. (For an appropriate literature procedure see E. W. Yankee, C. H. Lin and J. Fried, *Journ. Chem. Soc.*, 1972, 1120).

Another procedure involves reduction of the 9-keto racemate with a stereoselective reducing agent such as lithium perhydro-9b-borophenalyl hydride to give a 9α-hydroxy racemate (as the prostenoic acid ester and with the $C_{11}$ and $C_{15}$ or $C_{16}$ alcohol functions preferentially blocked as trialkylsilyl ethers) to the diastereomeric carbamates with an optically active isocyanate, e.g., (+)-1-phenylethylisocyanate or (−)-1-phenylethylisocyanate, followed by deblocking. Separation of the resulting diastereomers, for example (LXIV) and (LXV), can be accomplished by fractional crystallization or by the usual chromatographic procedures, or if necessary by high speed liquid chromatography involving, if necessary, recycling techniques. Base-treatment of the individual diastereomeric carbamates affords the individual diastereomeric alcohols, for example (LVII) and (LXVI).

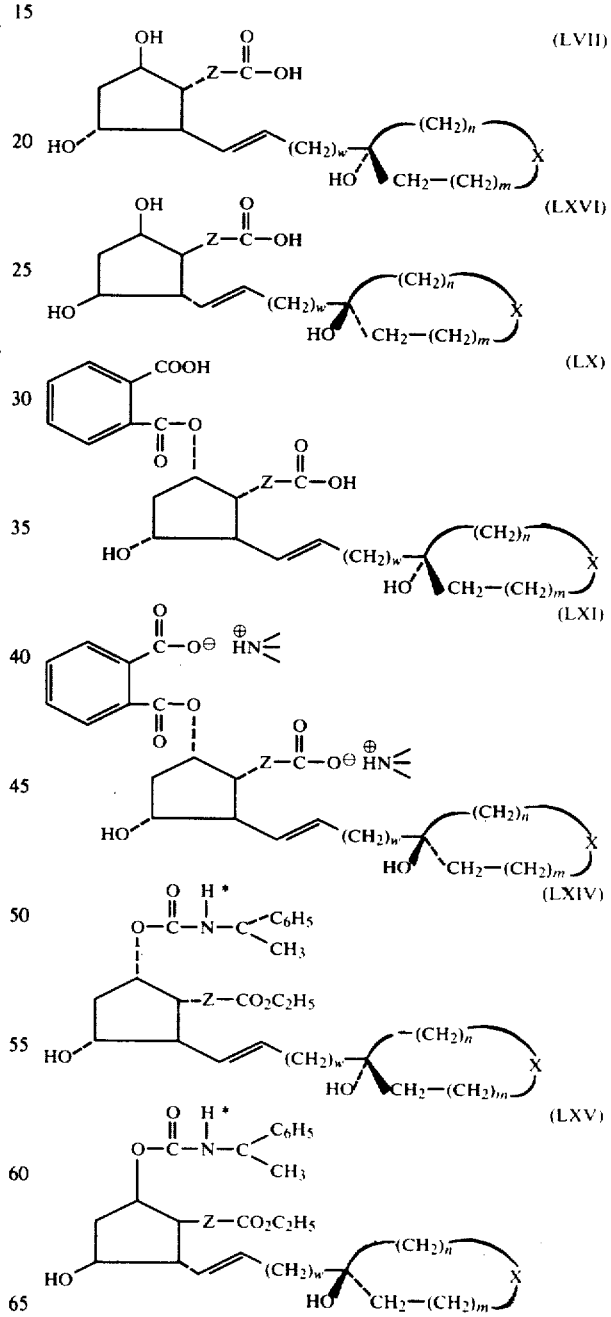

It is also possible to effect resolution of the 9α-hydroxy racemate, preferably as the prostenoate ester,

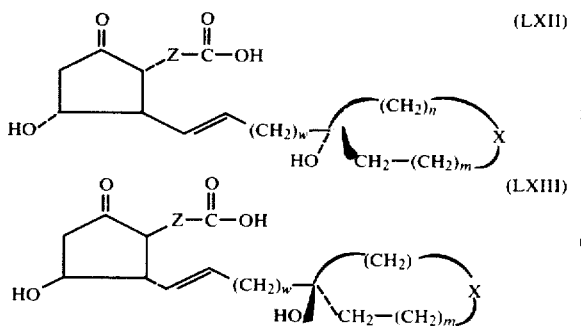

by esterification of the 9α-hydroxy function (prior preferential blocking as discussed hereinabove of $C_{11}$ and $C_{15}$ or $C_{16}$-hydroxy functions as trialkylsilyl ethers) with an optically active acid, via its acid chloride followed by deblocking the $C_{11}$ and $C_{15}$ or $C_{16}$ alcohol groups. Suitable optically active acids include ω-camphoric acid, menthoxyacetic acid, 3α-acetoxy-Δ⁵-etianic acid, (−)-α-methoxy-α-trifluoromethylphenylacetic acid and (+)-α-methoxy-α-trifluoromethylphenylacetic acid, and the like. The resulting diastereomeric esters, for example, (LXVII) and (LXVIII), are then separated by fractional crystallization or by chromatographic techniques including, if necessary, the use of high speed liquid chromatography. Saponification of the individual diastereomers then provides the individual 9α-hydroxyprostenoic acid enantiomers (LVIII) and (LXVI).

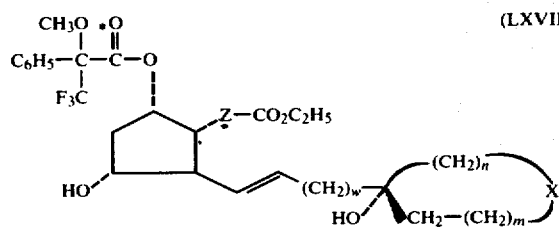

Although the above-described procedures are illustrated with examples having the 11α-hydroxy group, they apply as well to the members of the 11-deoxy series.

Another resolution procedure, less useful than the methods described above which are based on the 9α-hydroxy derivative, but which is particularly applicable to the 11-deoxy compounds of this invention, involves derivatization of the keto function of the 9-oxoprostenoic acid or ester racemate with the usual type of ketone derivatizing agents bearing an optically active center. The resulting mixture of diastereomeric derivatives can then be separated by fractional crystallization or by chromatography or, if necessary, by high speed liquid chromatography. The individual diastereomeric keto derivatives, for example, (LXIX) and (LXX), are then convertible to the individual 9-oxo enantiomers, for example (LXXI) and (LXXII), by any of the usual cleavage techniques, provided that they are sufficiently mild so as not to disturb the sensitive 11-hydroxy-9-keto system if it is present. (This latter point is not a problem with 11-unsubstituted derivatives.) Ketone reduction of the 9-oxo-enantiomer as described hereinabove then provides the corresponding 9α-hydroxy or 9β-hydroxy enantiomer. Among the optically active reagents useful for ketone derivatization are 1-α-aminoxy-γ-methylpentanoic acid hydrochloride [E. Testa, et al., Helv. Chimica Acta, 47 (3), 766 (1973)], menthylhydrazine, and 4-α-methylbenzylsemicarbazide. A useful procedure for the cleavage of oximes such as (LXIX) and (LXX) involves treatment of the oxime at about 60° C. for about 4 hours in 1:2 aqueous-tetrahydrofuran buffered with ammonium acetate and containing titanium trichloride.

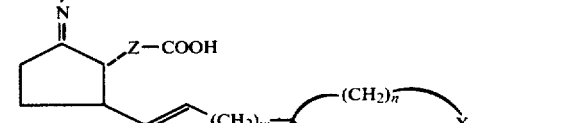

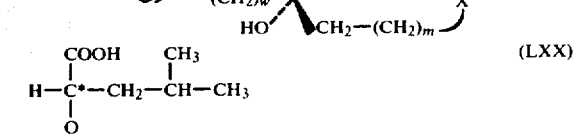

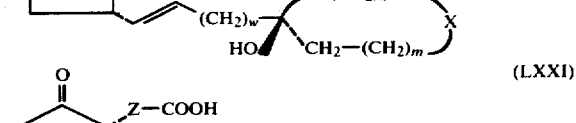

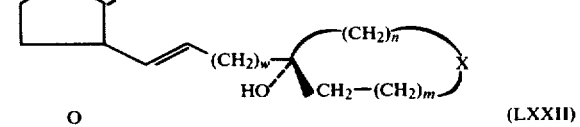

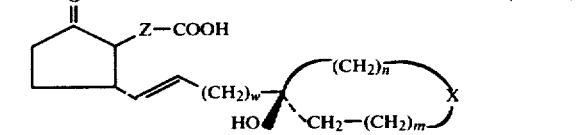

Other useful ketone derivatizing agents are optically active 1,2-glycols, e.g., D(−)-2,3-butanediol, or 1,2-dithiols, e.g., L(+)-2,3-butanedithiol. These are used to convert the 9-oxo racemate to 9,9-alkylenedioxa or 9,9-alkylenedithia diastereomers. Separation of diastereomers by chromatographic procedures, followed by regeneration of the individual 9-oxo enantiomer by ketal cleavage can be accomplished by procedures well-known in the art. Both ketalization and deketalization would have to be accomplished by procedures which would not disrupt the 11-oxo-9-keto system, which of course, is not a problem in the 11-unsubstituted series.

The preparation of the requisite cyclopentenones which contain a sulfur atom in the α-chain is described in Flowsheet C. In accordance with Flowsheet C wherein t is hereinabove described, treatment of 2-furyllithium (LXXIII) with a ω-chloroaldehyde (LXXIV) provides the chloroalcohol (LXXV). Treatment of the chloroalcohol (LXXV) with ethylmercaptoacetate furnishes the hydroxy ester (LXXVI) which upon hydrolysis with sodium formate/formic acid provides the 3-hydroxy-cyclopentenone (LXXVII). Treatment of the cyclopentenone (LXXVII) with sulfuric acid provides the required 4-hydroxy-cyclopentenone (LXXVIII) which after treatment with chlorotrimethylsilane and hexamethyl disilazene in pyridine provides the bissilylated cyclopentenone (LXXIX).

The 3-hydroxy-cyclopentenones of the type (LXXVII), the 4-hydroxy-cyclopentenones of the type (LXXVIII), and the bissilylated or bistetrahydropyrayl protected or other suitably protected 4-hydroxy-cyclopentenone of the type (LXXIX) are novel and useful compounds which are also embraced by this invention, as are the novel intermediates required for their preparation.

more useful than one of the corresponding above-mentioned known prostaglandins for at least one of the pharmacological purposes indicated below for the latter, either because it has a different and narrower spectrum of biological activity than the known prostaglandins, and therefore is more specific in its activity and causes smaller and fewer undesired side effects than the known prostaglandins, or because or its prolonged ac-

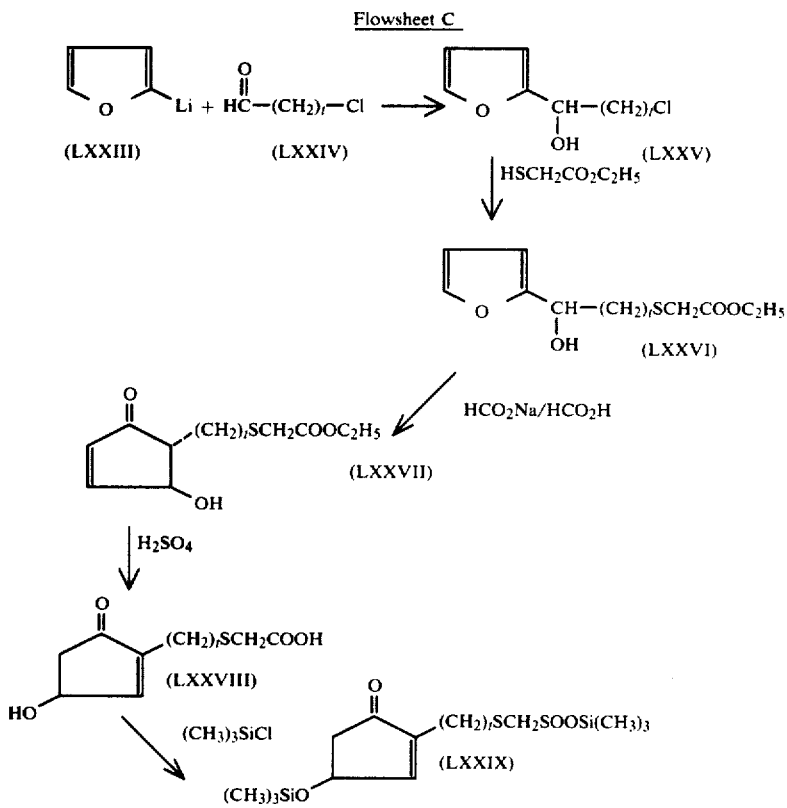

Flowsheet C

The ring system of certain of the novel compounds of this invention allow them to be characterized as follows:

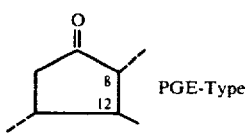

The novel compounds of this invention possess the pharmacological activity described below as associated with the appropriate above-described prostaglandin type.

The known PGE compounds are all potent in causing multiple biological responses even at low doses. For example, $PGE_1$ and $PGE_2$ are extremely potent in causing vasodepression and smooth muscle stimulation, and also are potent as anti-lipolytic agents. Moreover, for many applications, these known prostaglandins have an inconveniently short duration of biological activity. In striking contrast, the novel prostaglandin analogs of this invention are substantially more specific with regard to potency in causing prostaglandin-like biological responses, and/or having a substantially longer duration of biological activity. Therefore, each of these novel prostaglandin analogs is surprisingly and unexpectedly tivity, fewer and smaller doses of the novel prostaglandin analog can frequently be used to attain the desired result.

The 11-deoxy-PGE compounds are additionally selective in that they are at most relatively very weak stimulants of smooth muscle. The 11-deoxy PGE compounds have a further advantage in that they are much more stable and have a longer "shelf-life" than the corresponding 11-hydroxy derivatives as described more fully hereinbelow.

Another advantage of the novel compounds of this invention, compared with the known prostaglandins, is that these novel compounds are administered effectively, orally, sublingually, intravaginally, bucally, or rectally, in addition to the usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

$PGE_1$, $PGE_2$, $PGE_3$, and dihydro-$PGE_1$ and their esters and pharmacologically acceptable salts, are extremely potent in causing various biological responses.

For that reason, these compounds are useful for pharmacological purposes. See, for example, Bergstrom, et al., Pharmacol. Rev., 20, 1 (1968), and references cited therein. A few of those biological responses are systemic arterial blood pressure lowering in the case of the PGE compounds as measured, for example, in anesthetized (phenobarbital sodium) pentolinium-treated rats with indwelling aortic and right heart cannulas; stimulation of smooth muscle as shown, for example by tests on strips or guinea pig ileum, rabbit duodenum, or gerbil colon; potentiation of other smooth muscle stimulants; antilipolytic activity as shown by antagonism of epineephrine-induced mobilization of free fatty acids or inhibition of the spontaneous release of glycerol from isolated rat fat pads; inhibition of gastric secretion in the case of the PGE compounds as shown in dogs with secretion stimulated by food or histamine infusion; activity on the central nervous system; decrease of blood platelet adhesiveness in the case of PGE, as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the PGE compounds, stimulation of epiermal proliferation and keratinization as shown when applied in culture to embryonic chick and rat skin segments.

Because of these biological responses, these known prostaglandins are useful to study, prevent, control, or alleviate a wide variety of disease and undesirable physiological conditions in birds and mammals, including humans, useful domestic animals, pets, and zoological specimens, and in laboratory animals, for example, mice, rats, rabbits, and monkeys.

For example, these compounds, and especially the PGE compounds, are useful in mammals, including man, as nasal decongestants. For this purpose, the compounds are used in a dose range of about 10 μg to about 10 mg per ml of a pharmacologically suitable liquid vehicle or as an aerosol spray, both for typical application.

The PGE compounds are useful in mammals, including man and certain useful animals, e.g., dogs and pigs, to reduce and control excessive gastric secretion, thereby reducing or avoiding gastric erosion or gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 μg to about 500 μg per kg of body weight per minute, or in a total daily dose by injection or infusion in the range about 0.1 to about 20 mg per kg of body weight per day, the exact dose depending on the age, weight, and condition of the patient or animal, and on the frequency and route of administration. These compounds may also be useful in conjunction with various non-steroidal anti-inflammatory agents, such as aspirin, phenylbutazone, indomethacin and the like, to minimize the well-known ulcerogenic effects of the latter.

The $PGE_1$ compounds are useful whenever it is desired to inhibit platelet aggregation, to reduce the adhesive character of platelets, and to remove or prevent the formation of thrombi in mammals, including man, rabbits, and rats. For example, these compounds are useful in treatment and prevention of myocardial infarcts, to treat and prevent post-operative thrombosis. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range of about 0.005 to about 20 mg per kg of body weight per day are used, the exact dose depending on the age, weight, and condition of the patient or animal, and on the frequency and route of administration.

11α-Hydroxy-PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore $PGE_2$, for example, is useful in place of or in combination with less than usual amounts of these known smooth muscle stimulators, for example, to relieve the symptoms of paralytic ileus, or to control or prevent uterine bleeding after abortion or delivery, to aid in expulsion of the placenta, and during the puerperium. For the latter purpose, the PGE compound is administered by intravenous infusion immediately after abortion or delivery at a dose in the range about 0.01 to about 50 μg per kg of body weight per minute until the desired effect is obtained. Subsequent doses are given by intravenous, subcutaneous, or intramuscular injection or infusion during puerperium in the range of 0.01 to 2 mg per kg of body weight per day, the exact dose depending on the age, weight, and condition of the patient or animal.

The PGE compounds are useful as hypotensive agents to reduce blood pressure in mammals including man. For this purpose, the compounds are administered by intravenous infusion at the rate about 0.01 to about 50 μg per kg of body weight per minute, or in a single or multiple doses of about 25 to 2500 μg per kg of body weight total per day.

The PGE compounds are useful in place of oxytoxin to induce labor in pregnant female animals, including man, cows, sheep, pigs, at or near term or in pregnant animals with intrauterine death of the fetus from about 20 weeks to term. For this purpose, the compound is infused intravenously at a dose 0.01 to 50 μg per kg of body weight per minute until or near the termination of the second stage of labor, i.e., expulsion of the fetus. These compounds are especially useful when the female is one or more weeks postmature and natural labor has not started, or 12 to 60 hours after the membranes have ruptured and natural labor has not yet started.

The PGE compounds are useful for controlling the reproductive cycle in ovulating female mammals, including humans and other animals. For that purpose, a PGE compound is administered systematically at a dose level in the range of 0.01 mg to about 50 mg per kg of body weight, advantageously during a span of time starting approximately at the time of ovulation and ending approximately at the time of menses or just prior to menses. Additionally, expulsion or an embryo or fetus is accomplished by similar administration of the compound during the first third or the second third of the normal mammalian gestation period. Accordingly they are useful as abortifacients. They are also useful for induction of menses during approximately the first two weeks of a missed menstrual period and accordingly are useful as contraceptive anti-fertility agents.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate a wet dressing for topical application to second and/or third degree burns of skin area 5 to 25 square centimeters would advantageously involve use of an isotonic aqueous solution containing one to 500 μg/ml of the PGB compound or several times that concentration of the PGE compound. Especially for topical use, these prostaglandins are useful in combination with antibiotics, for example, gentamycin, neomycin, polymyxin B, bacitracin, spectinomycin, and oxytetracycline, with other antibacterials, for example, mafenide hydrochloride, sulfadiazine, furazolium chloride, and nitrofurazone, and with corticoid steroids, for example hydrocortisone, prednisolone, methylprednisolone, and fluprednisolone, each of those being used in the combination at the usual concentration suitable for its use alone.

The novel compounds of this invention induce the biological responses described hereinabove as associated with its particular prostaglandin type. These novel compounds are accordingly useful for the above-described corresponding purposes in the same manner as described above.

The novel PGE compounds of this invention are also useful as bronchodilators for the treatment of asthma and chronic bronchitis; as such they may be conveniently administered by inhalation of aerosol sprays prepared in a dose range of about 10 μg to about 10 mg per ml of a pharmacologically suitable liquid vehicle.

These derivatives described hereinabove are also more selective in their biological action and generally induce a more prolonged effect than the corresponding natural prostaglandins. These preparations are novel, completely unanticipated and provide distinct and important advantages.

In addition, certain of the novel compounds of this invention are useful for the preparation of other novel compounds of this invention.

It is well known that platelet aggregation inhibitors may be useful as anti-thrombotic drugs. Inhibition of platelet aggregation can be conveniently measured in vitro by monitoring changes in optical density and/or light transmission in platelet rich plasma upon addition of suitable aggregating agents such as adenosine diphosphate, epinephrine, thrombin or collagen. Alternatively, platelet aggregation can be measured in vitro using platelet rich plasma obtained at various time intervales from animals give inhibitors by an oral or parenteral route.

The compounds of the present invention exhibit the ability to inhibit platelet aggregation in vitro when tested by the following procedure.

Human protein rich plasma is incubated with modified Tyrode's solution in a proportion of 40–50% human protein rich plasma. The test compounds are added at varying concentrations and after 5 minutes incubation, an aggregating agent such as adenosine diphosphate or collagen is added. The change in optical density (light transmission) is monitored by eye and inhibition is recorded as a (−) or lack of inhibition is recorded as a (+). Test compounds are considered active if they inhibit adenosine diphosphate or collagen induced aggregation at a concentration of 25 mcq/ml or less within 5–10 minutes. The results of this test on representative compounds of this invention appear in Table A.

TABLE A

| | Inhibition of Platelet Aggregation - In Vitro | | | | | | | |
|---|---|---|---|---|---|---|---|---|
| | Adenosine Diphosphate Drug Concentration μg/ml | | | | Collagen Drug Concentration μg/ml | | | |
| Compound | 250 | 25 | 2.5 | 0.25 | 250 | 25 | 2.5 | 0.25 |
| nat(and ent)-15-Hydroxy-9-oxo-15,16-tetramethylene-17,18,19,20-tetranor-13-trans-prostenoic acid | (−) | (−) | (+) | (+) | (−) | (−) | (+) | (+) |
| nat(and ent)-15-Hydroxy-9-oxo-15,16-tetramethylene-17,18,19,20-tetranor-13-trans,5-cis,10-prostatrienoic acid | (−) | (+) | | | (−) | (+) | | |
| nat(and ent)-11α,15-dihydroxy-9-oxo-15,16-tetramethylene-17,18,19,20-tetranor-5-cis,13-trans-prostadienoic acid | (−) | (−) | (−) | (+) | (−) | (−) | (−) | (+) |
| nat-15S,16R(and ent-15R,16S)-11α,15-Dihydroxy-9-oxo-15,16-trimethylene-13-trans-5-cis-prostadienoic acid and nat-15R,16S(and ent-15S,16R)-11α,15-Dihydroxy-9-oxo-15,16-trimethylene-13-trans-5-cis-prostadienoic acid | (−) | (+) | | | (+) | | | |
| nat(and ent)-11α,15-Dihydroxy-9-oxo-15,16-tetramethylene-17,18,19,20,-tetranor-13-trans-prostenoic acid | (−) | (−) | (−) | (+) | (−) | (−) | (−) | (+) |
| nat(and ent)-9-oxo-15,16-Tetramethylene-17,18,19,20-tetranor-15,13-trans-prostadienoic acid | (−) | (−) | | | (−) | (−) | | |

(−) = Inhibition
(+) = No inhibition

Recent studies have shown that prostaglandins E₂ are formed from arachidonic acid during platelet aggregation produced by various agents. It has also been shown that cycloendoperoxides formed during the conversion of arachidonic acid to $PGE_2$ and $PGF_{2\alpha}$ may be more important as regulators of aggregation. $PGE_1$, as well as other non-steroidal anti-inflammatory drugs which inhibit prostaglandin synthetase, are effective inhibitors of platelet aggregation. Studies with intravenous arachidonate in rabbits or intra-arterially in rats have shown that in vivo administration of arachidonate is also correlated with platelet aggregation in the microvasculature of the lung and the brain. Thus, prostaglandin analogs of PGE$_2$ or the cycloendoperoxides, as well as drugs that inhibit the cyclooxygenase enzyme, are therefore antiplatelet drugs and anti-thrombotic drugs.

The compounds of the present invention inhibit respiratory depression produced by arachidonate in mice when tested by the following procedure.

Swiss, male, albino mice, weighing about 20 g, are placed in control and drug groups, each with 4–6 mice and fasted. The drug mice are dosed with 50, 25, 10, or 1 mg/kg of a test compound suspended in volumes of 0.5, 0.25, or 0.10 ml of 2% starch solution. Control animals receive starch solution alone. After 2 hours all the mice are challenged with an intravenous dose of 50 mg/kg of sodium arachidonate in a volume of 0.2 ml, by tail vein. The onset of effect and duration of respiratory depression and recovery or death is quantitated. The percent inhibition of respiratory depression is computed from the mean of the drug group and the mean of the control group. Compounds giving 30% or more inhibition at 25 mg/kg or less are considered active. The results of this test on representative compounds of this invention are recorded in Table B.

ing test procedure. This procedure is a modification of the technique described by Pike, et al., Prostaglandins, Nobel Symposium 2, Stockholm, June, 1966, pg. 165.

Male Wistar strain rats (Royal Hart Farms) averaging approximately 250 g in weight are fastened to rat boards in a supine position by means of canvas vests and limb ties. The animals are anesthetized with a 900 mg/kg intraperitoneal dose of urethane. The left carotid artery is cannulated with polyethylene 50 tubing to measure arterial blood pressure and the left external jugular vein is cannulated with polyethylene 50 tubing for drug infusion. The animals are allowed to equilibrate for 15–30 minutes. The test compound is infused in 0.5 ml of saline, over a one minute period, at the indicated dose level, using a Harvard Model 940 infusion pump and a 6 cc syringe at speed 5. Each drug dose is flushed with 0.4 ml of saline. The mean arterial blood pressure is measured before and after drug administration using a Statham model P23Db pressure transducer and a Brush model 260 recorder. The percent depression in mean arterial blood pressure and the duration of at least a 10% depression induced by representative compounds of this invention are recorded in Table C.

TABLE C

| Compound | Hypotensive Activity | | | |
|---|---|---|---|---|
| | Dose mg/kg | No. of Animals | Percent Depression of Mean Arterial Blood Pressure | Duration in Minutes of at Least 10% Depression |
| nat-15S,16R(and ent-15R,16S)-11α,15-Dihydroxy-9-oxo-15,16-trimethylene-13-trans-5-cis-prostadienoic acid and nat-15R,16S(and ent-15S,-16R)-11α,15-Dihydroxy-9-oxo-15,16-trimethylene-13-trans-5-cis-prostadienoic acid | 1.7 | 3 | −47 | >10 |
| nat(and ent)-11α,15-Dihydroxy-9-oxo-15,16-tetramethylene-17,18,19,3,-tetranor-13-trans-prostenoic acid | 2.1 | 2 | −39 | 16 |
| nat(and ent)-15-Hydroxy-9-oxo-15,16-tetramethylene-17,18,19,20-tetranor-13-trans-prostenoic acid | 1.8 | 3 | −9 | 4 |
| nat(and ent)-11α,15-Dihydroxy-9-oxo-15,16-tetramethylene-17,18,19,20-tetranor-5-cis-13-trans-prostadienoic acid | 2.2 | 2 | −31 | 23 |
| nat-15S,16R(and ent-15R,16S)-15-Hydroxy-9-oxo-15,16-trimethylene-13-trans-prostenoic acid and nat-15R,16S(and ent-15S,16R)-15-hydroxy-9-oxo-15,16-trimethylene-13-trans-prostenoic acid | 2.0 | 2 | −38 | 4 |
| Ethyl nat-15S,16R(and ent-15R,16S)-15-hydroxy-9-oxo-15,16-trimethylene-13-trans-prostenoate and Ethyl nat-15R,16S(and ent-15S,16R)-15-hydroxy-9-oxo-15,16-trimethylene-13-trans-prostenoate | 1.9 | 2 | −18 | 7 |
| Ethyl nat-15R,16R(and ent-15S,16S)-15-hydroxy-9-oxo-15,16-trimethylene-13-trans-prostenoate | 4.0 | 2 | −16 | 4 |
| Ethyl nat-15S,16S(and ent-15R,16R)-hydroxy-9-oxo-15,16-trimethylene-13-trans-prostenoate | 1.6 | 2 | −43 | 5 |

TABLE B

| Inhibition of Respiratory Depression - In Vivo | | | |
|---|---|---|---|
| | Percent Inhibition | | |
| Compound | 25 mg/kg | 10 mg/kg | 1 mg/kg |
| nat(and ent)-15-Hydroxy-9-oxo-15,16-tetramethylene-17,18,19,20-tetranor-13-trans-prostenoic acid | | | 33 |
| nat(and ent)-11α,15-Dihydroxy-9-oxo-15,16-tetramethylene-17,18,19,20-tetranor-5-cis,13-trans-prostadienoic acid | 14 | 6 | |
| nat(and ent)-9-oxo-15,16-Tetramethylene-17,18,19,20-tetranor-15,13-trans-prostadienoic acid | 28 | | |

The novel compounds of the present invention are useful as hypotensive agents and their prostaglandin-like hypotensive activity is demonstrated in the following The compounds of this invention are also useful as bronchodilators and accordingly have potential application in the treatment of asthma.

Bronchodilator activity is determined in guinea pigs against bronchospasms elicited by intravenous injections of 5-hydroxytryptamine, histamine or acetylcholine by the Konzett procedure. [See J. Lulling, P. Lievens, F. El Sayed and J. Prignot, Arzeneimittel-Forschung, 18, 995 (1968).] In Table D, bronchodilator activity for representative compounds of this invention against one or more of the three spasmogenic agents is expressed as an $ED_{50}$ determined from the results obtained with three logarithmic cumulative intravenous doses.

TABLE D

| | Bronchodilator Activity | | |
|---|---|---|---|
| | $ED_{50}$, mg/kg | | |
| Compound | 5-Hydroxytryptamine | Histamine | Acetylcholine |
| nat-15S,16R(and ent-15R,16S)-11α,15-Dihydroxy-9-oxo-15,16-trimethylene-13-trans-5-cis-prostadienoic acid and nat-15R,16S(and ent-15S,16R)-11α,15-dihydroxy-9-oxo-15,16-trimethylene-13-trans-5-cis-prostadienoic acid | $576 \times 10^{-9}$ | $648 \times 10^{-9}$ | $>3.2 \times 10^{-6}$ |
| nat(and ent)-11α,15-Dihydroxy-9-oxo-15,16-tetramethylene-17,18,19,20-tetranor-13-trans-prostanoic acid | $57 \times 10^{-6}$ | $7.69 \times 10^{-6}$ | $56.6 \times 10^{-6}$ |
| nat-15S,16S(and ent-15R,16R)-15-hydroxy-9-oxo-15,16-trimethylene-13-trans-prostenoic acid | $112 \times 10^{-6}$ | $25.8 \times 10^{-6}$ | $413 \times 10^{-6}$ |
| nat-15R,16R(and ent-15S,16S)-15-Hydroxy-9-oxo-15,16-trimethylene-13-trans-prostenoic acid | $18 \times 10^{-8}$ | $2.07 \times 10^{-6}$ | $43 \times 10^{-6}$ |
| nat(and ent)-15-Hydroxy-9-oxo-15,16-tetramethylene-17,18,19,20-tetranor-13-trans,5-cis,10-prostatrienoic acid | $>3.2 \times 10^{-3}$ | $632 \times 10^{-6}$ | $>3.2 \times 10^{-3}$ |
| nat(and ent)-11α,15-Dihydroxy-9-oxo-15,16-tetramethylene-17,18,19,20-tetranor-5-cis,13-trans-prostadienoic acid | $58.7 \times 10^{-6}$ | $32.8 \times 10^{-6}$ | $115 \times 10^{-6}$ |
| nat-15S,16R(and ent-15R,16S)-15-Hydroxy-9-oxo-15,16-trimethylene-13-trans-prostenoic acid and nat-15R,16S(and ent-15S,16R)-15-Hydroxy-9-oxo-15,16-trimethylene-13-trans-prostenoic acid | $320 \times 10^{-6}$ | $666 \times 10^{-9}$ | $56.2 \times 10^{-6}$ |
| nat-15S,16R(and ent-15R,16S)-11α,15-Dihydroxy-9-oxo-15,16-trimethylene-13-trans-5-cis-prostadienoic acid and nat-15R,16S(and ent-15S,16R)-11α,15-Dihydroxy-9-oxo-15,16-trimethylene-13-trans-5-cis-prostadienoic acid | $576 \times 10^{-9}$ | $648 \times 10^{-9}$ | $3.2 \times 10^{-6}$ |
| nat(and ent)-11α,15-Dihydroxy-9-oxo-15,16-tetramethylene-17,18,19,20-tetranor-13-trans-prostenoic acid | $57 \times 10^{-6}$ | $7.69 \times 10^{-6}$ | $56.6 \times 10^{-6}$ |
| nat-15S,16S(and ent-15R,16R)-15-Hydroxy-9-oxo-15,16-trimethylene-13-trans-prostenoic acid | $112 \times 10^{-6}$ | $25.8 \times 10^{6}$ | $413 \times 10^{-6}$ |
| nat-15R,16R(and ent-15S,16S)-15-Hydroxy-9-oxo-15,16-trimethylene-13-trans-prostenoic acid | $18 \times 10^{-8}$ | $2.07 \times 10^{-6}$ | $43 \times 10^{-6}$ |

The invention will be described in greater detail in conjunction with the following specific examples.

EXAMPLE 1

Preparation of trans-1-Hydroxy-2-(3-trifluoromethyl)phenoxycyclopentane

A mixture of 88 g of cyclopentene oxide, 150.7 g of 3-trifluoromethylphenol, 5.0 g of sodium hydroxide in 30 ml of water and 4.0 g of methyltricaprylyl ammonium chloride is stirred at 70°-80° C. for 51 hours and at 25° C. for 96 hours. The mixture is then diluted with methylene chloride and poured into water. The organic layer is washed with dilute sodium hydroxide solution and water. The solution is dried over magnesium sulfate. The solvent is removed giving 221.5 g of a liquid which is distilled (bp 110°-113° C. 0.8 mm) giving trans-1-hydroxy-2-(3-trifluoromethyl)phenoxycyclopentane.

EXAMPLE 2

In the manner described above in Example 1 from 4-fluorophenol and cyclopentane epoxide is prepared trans-1-hydroxy-2-(4-fluoro)phenoxycyclopentane.

EXAMPLE 3

In the manner described above in Example 1 from 3-chlorophenol and cyclopentane epoxide is prepared trans-1-hydroxy-2-(3-chloro)phenoxycyclopentane.

EXAMPLE 4

Preparation of 2-(3-Trifluoromethylphenoxy)cyclopentanone

To a suspension of 327.43 g of pyridinium chlorochromate in one liter of methylene chloride is added 220 g of trans-1-hydroxy-2-(3-trifluoromethylphenoxy)cyclopentane in 500 ml of methylene chloride. The mixture is stirred for 2 hours 15 minutes. Another 50 g of the oxidizing agent is added and the mixture is stirred for 4½ hours. The mixture is diluted with ether and decanted from a black residue which is washed with more ether. The combined solutions are filtered through silica gel. The solvent is removed. The residue is dissolved in ether and again filtered through silicagel. The solvent is removed and the residue is distilled (bp 113°-116° C., 1.5 mm) to give 188 g of 2-(3-trifluoromethylphenoxy)cyclopentanone.

EXAMPLE 5

In the manner described above for Example 4 is prepared from the product of Example 2; 2-(4-(fluorophenoxy)cyclopentanone.

EXAMPLE 6

In the manner described above for Example 4 is prepared from the product of Example 3; 2-(3-chlorophenoxy)cyclopentanone.

EXAMPLE 7

Preparation of 1R,2S(and 1S,2R)-1-Ethynyl-1-hydroxy-2-butylcyclopentane and 1R,2R(and 1S,2S)-1-ethynyl-1-hydroxy-2-butylcyclopentane Into 150 ml of dry tetrahydrofuran is bubbled purified acetylene, as a solution of 2.4 M n-butyl magnesium chloride (92 ml) is added dropwise with stirring over a 2 hour period. To the resulting solution of acetylene magnesium chloride is added 21 g of 2-butylcyclopentanone in 50 ml of tetrahydrofuran dropwise over 15 minutes. The solution is stirred for 30 minutes and then is poured into an ice cold solution of saturated ammonium chloride. The mixture is acidifed to pH 5 and extracted with ether. The ether solution is washed with brine and dried over magnesium chloride. The ether is removed and the residue is distilled giving 14.8 g of a colorless liquid. This is chromatographed on a dry column of silica-gel eluting with benzene-ethyl acetate (19:1) to separate isomers giving 1R,2S(and 1S,2R)-1-ethynyl-1-hydroxy-2-butylcyclopentane and 1R,2R(and 1S,2S)-1-ethynyl-1-hydroxy-2-butylcyclopentane.

EXAMPLE 8

Preparation of 1-propargyl-1-hydroxycyclohexane

A stirred suspension of 121.6 g (5.0 mol) of magnesium in 1-1 of anhydrous ether is treated with 0.6 g of mercuric chloride and about 100 mg of iodine. After several minutes, 3 ml of propargyl bromide is added and if no exotherm is noted, a small amount of reacting propargyl bromide and magnesium in either is added. When the reaction begins, a mixture of 5.0 mol of cyclohexanone and 595 g (5.0 mol) of propargyl bromide is added dropwise at a rate that produces vigorous refluxing of the solution. (The propargyl bromide must always be present in some excess otherwise the reaction will stop. If this happens, the addition of about 1 ml of propargyl bromide will restart the reaction.) After about half of the propargy bromide-cyclohexanone mixture has been added, another 500-750 ml of ether is used to dilute the reaction mixture. At the end of the addition, the reaction mixture is refluxed for at least 0.5 hour, cooled and poured into 4 liters of saturated ammonium chloride during good stirring. The ethereal layer is separated and the aqueous layer is washed with ether several times and the combined extract is washed twice with saturated sodium chloride solution and dried over anhydrous magnesium sulfate. Evaporation of the ether yields 583 g (630 g theory) of a dark oil which is distilled giving purified 1-propargyl-1-hydroxycyclohexane.

EXAMPLES 9-27

In the manner of Examples 7 and 8 described above the following acetylenic alcohols listed in Table I were prepared from the acetylenic Grignard reagent and ketone specified.

TABLE I

| Example | Grignard Reagent | Ketone | Acetylenic Alcohol |
|---|---|---|---|
| 9 | acetylene magnesium chloride | cyclohexanone | 1-ethynyl-1-hydroxycyclohexane |
| 10 | acetylene magnesium chloride | cyclopentanone | 1-ethynyl-1-hydroxycyclopentane |
| 11 | acetylene magnesium chloride | cycloheptanone | 1-ethynyl-1-hydroxycycloheptane |
| 12 | acetylene magnesium chloride | 3-propylcyclopentanone | 1R,3S-(and 1S,3R-) 1-ethynyl-1-hydroxy-3-propylcyclopentane |
| 13 | acetylene magnesium chloride | 3-propylcyclopentanone | 1R,3R-(and 1S,3S-)1-ethynyl-1-hydroxy-3-propylcyclopentane |
| 14 | acetylene magnesium chloride | 2-butylcyclohexanone | 1R,2S-(and 1S,2R-) 1-ethynyl-1-hydroxy-2-butylcyclohexane |
| 15 | acetylene magnesium chloride | 2-butylcyclohexanone | 1R,2R-(and 1S,2S-) 1-ethynyl-1-hydroxy-2-butylcyclohexane |
| 16 | acetylene magnesium chloride | 2-(3-trifluoromethylphenoxy)-cyclopentanone | 1R,2S-(and 1S,2R-) 1-ethynyl-1-hydroxy-2-(3-trifluoromethylphenoxy)cyclopentane |
| 17 | acetylene magnesium chloride | 2-(3-trifluoromethylphenoxy)-cyclopentanone | 1R,2R-(and 1S,2S-) 1-ethynyl-1-hydroxy-2-(3-trifluoromethylphenoxy)cyclopentane |
| 18 | acetylene magnesium chloride | 2-(4-fluorophenoxy)cyclopentanone | 1R,2S-(and 1S,2R-) 1-ethynyl-1-hydroxy-2-(4-fluorophenoxy)cyclopentane |
| 19 | acetylene magnesium chloride | 2-(4-fluorophenoxy)cyclopentanone | 1R,2R-(and 1S,2S-) 1-ethynyl-1-hydroxy-2-(4-fluorophenoxy)cyclopentane |
| 20 | acetylene magnesium chloride | 2-(3-chlorophenoxy)cyclopentanone | 1R,2S-(and 1S,2R-) 1-ethynyl-1-hydroxy-2-(3-chlorophenoxy)cyclopentane |
| 21 | acetylene magnesium chloride | 2-(3-chlorophenoxy)cyclopentanone | 1R,2R-(and 1S,2S-) 1-ethynyl-1-hydroxy-2-(3-chlorophenoxy)cyclopentane |
| 22 | acetylene magnesium chloride | 3-methylcyclohexanone | 1R,3S-(and 1S,3R-) 1-ethynyl-1-hydroxy-3-methylcyclohexane |
| 23 | acetylene magnesium chloride | 3-methylcyclohexanone | 1R,3R-(and 1S,3S-) 1-ethynyl-1-hydroxy-3-methylcyclohexane |
| 24 | propargyl magnesium bromide | 2-butylcyclopentanone | 1R,2S-(and 1S,2R-) 1-propargyl-1-hydroxy-2-butycyclopentane |
| 25 | propargyl magnesium bromide | 2-butylcyclopentanone | 1R,2R-(and 1S,2S-) 1-propargyl-1-hydroxy-2-butylcyclopentane |
| 26 | propargyl magnesium bromide | 2-(3-trifluoromethylphenoxy)-cyclopentanone | 1R,2S-(and 1S,2R-) 1-propargyl-1-hydroxy-2-(3-trifluoromethylphenoxy)cyclopentane |
| 26b | propargyl magnesium bromide | 2-(3-trifluoromethylphenoxy)-cyclopentanone | 1R,2S-(and 1S,2R-) 1-propargyl-1-hydroxy-2-(3-trifluoromethylphenoxy)cyclopentane |

EXAMPLE 28a

Preparation of 1R,2S(and 1S,2R)-1-Ethynyl-1-trimethylsilyloxy-2-butylcyclopentane To a solution of 29.4 g of 1R,2S(and 1S,2R)-1-ethynyl-1-hydroxy-2-butylcyclopentane and 30.2 g of imidazole in 180 ml of dimethylformamide is added at 0° C. with stirring 24.1 g of trimethylsilylchloride. The mixture is stirred for 3 hours. The mixture is poured into 700 ml of hexane and washed twice with water and once with brine. The ether solution is dried over magnesium sulfate. The solvent is removed and the residue is distilled (bp 64°-72° C., 0.6 mm) to give 35.8 g of 1R,2S(and 1S,2R)-1-ethynyl-1-trimethylsilyloxy-2-butylcyclopentane.

EXAMPLE 28b

Preparation of 1R,2R(and 1S,2S)-1-Ethynyl-1-trimethylsilyloxy-2-butylcyclopentane To a mixture of 45.0 g of 1R,2R(and 1S,2S)-1-ethynyl-1-hydroxy-2-butylcyclopentane and 46.2 g of imidazole in 255 ml of dimethylformamide at 0° C. under nitrogen is added 36.9 g of trimethylsilylchloride. The mixture is stirred at room temperature for 3 hours and then poured into 700 ml of hexane. Water is added, the organic layer is separated and the water layer is extracted with hexane. The combined hexane solutions are washed twice with water and dried over magnesium sulfate. The solvent is removed and the residue is distilled giving the product as 53 g of a colorless oil.

EXAMPLE 28c

Preparation of 1-Ethynyl-1-trimethylsilyloxycyclohexane

A 194 g portion of imidazole and 158.2 g of 1-ethynylcyclohexan-1-ol are mixed with 500 g of dimethylformamide with cooling in an ice bath. A 152 g portion of trimethylchlorosilane is added with cooling and stirring in about one minute. The mixture is stirred for one hour and allowed to stand overnight. One liter of hexane is added. The lower layer is separated, diluted with water and extracted with hexane. The hexane layers are washed several times with water and then combined and dried over magnesium sulfate. Filtration and then evaporation of the hexane gives 198.5 g of product which is distilled giving 168 g of the desired product.

EXAMPLE 28d

Preparation of 1-Propargyl-1-trimethylsilyloxycyclohexane

To a stirred solution of 55.4 g of 1-(2-propyn-1-yl)cyclohexanol [H. Gutmann, et al., Helv. Chim. Acta, 42, 719 (1959)] and 79 g of imidazole in 240 ml of DMF at 10° C. initially is added 56 ml of chlorodimethylsilane during 10 minutes. The cloudy yellow solution is stirred at room temperature for 26 hours. The resulting mixture is partitioned between 1000 ml of hexane and 400 ml of water at 0°-5° C. The hexane phase is washed successively with 6×200 ml of cold water and 200 ml of brine. The extract is dried over magnesium sulfate, filtered, and evaporated to give 85 g of colorless liquid, i.r. (film): 1240 and 830 cm$^{-1}$ (trimethylsilyloxy group).

EXAMPLE 29a

Preparation of 1R,2S(and 1S,2R)-1-(trans-2-Iodovinyl)-1-trimethylsilyloxy-2-butylcyclopentane To a mixture of 9.2 g of sodium borohydride and 45.8 g of 2-methyl-2-butene in 350 ml of dry tetrahydrofuran at 0° C. with stirring under nitrogen is added, over 20 minutes, 41.1 ml of boron trifluoride etherate. After 3 hours, to this resulting solution of diisoamylborane is added 38.8 g of 1R,2S(and 1S,2R)-1-ethynyl-1-trimethylsilyloxy-2-butylcyclopentane in 40 ml of tetrahydrofuran in 20 minutes. The mixture is stirred 2 hours and then stored at −20° C. overnight. The mixture is allowed to warm to 0° C. and at 0° C. 85 g of dry trimethylamineoxide is added portionwise over 20 mintues. After stirring at 25° C. for one hour, the mixture is filtered through diatomaceous earth. The filtrate is poured simultaneously with a solution of 230 g of iodine in 250 ml of tetrahydrofuran into a stirred, cold solution of 430 g of sodium hydroxide in 1900 ml of water. After stirring for 30 minutes, the organic layer is separated. The aqueous layer is extracted with ether. The combined organic solutions are washed twice with a saturated solution of sodium thiosulfate and once with brine. The solution is dried over magnesium sulfate, the solvent is removed and the residue is dissolved in hexane. The hexane solution is filtered through diatomaceous earth and silica gel. The hexane is removed and the residue is purified by dry column chromatography on silica gel eluting with hexane: 45.35 g of 1R,2S(and 1S,2R)-1-(trans-2-iodovinyl)-1-trimethylsilyloxy-2-butylcyclopentane is obtained.

EXAMPLE 29b

Preparation of 1R,2R(and 1S,2S)-1-(trans-2-Iodovinyl)-1-trimethylsilyloxy-2-butylcyclopentane To a mixture of 12.22 g of sodium borohydride and 60.82 g of 2-methyl-2-butene in 450 ml of tetrahydrofuran under nitrogen at 0° C., is added 54.6 ml of boron trifluoride etherate, dropwise over a 20 minute period. The solution is stirred at 0° C. for 2 hours and then at room temperature for 30 minutes. This solution is cooled to 0° C. and 55.5 g of 1R,2R(and 1S,2S)-1-ethynyl-1-trimethylsilyloxy-2-butylcyclopentane in 50 ml of tetrahydrofuran is added. The mixture is allowed to stand in a cold room overnight. To this mixture at 0° C. is added with stirring 112.8 g of trimethylamine oxide over a 20 minute period. The mixture is stirred at room temperature for 90 minutes and then filtered. To the filtrate is added simultaneously a solution of 565 g of sodium hydroxide in 2000 ml of water and a solution of 300 g of iodine in 300 ml of tetrahydrofuran. The mixture is stirred 30 minutes, the organic layer is separated and the aqueous layer is extracted with ether. The combined organic solutions are washed with saturated sodium thiosulfate solution and with saturated sodium chloride solution. The solution is dried with magnesium sulfate and filtered through a pad of silica gel. The solution is removed giving an orange liquid which is chromatographed on a dry column of silica gel giving 59.5 g of the product as a yellow liquid.

EXAMPLE 30

30, were converted to their corresponding trans-2-tri-n-butylstannyl derivatives (Table II).

TABLE II

| Example | Acetylene of Example | Method of Example | Vinyl Iodide or Vinyl Tin Compound |
|---|---|---|---|
| 31 | 9 | 29 | 1-(trans-2-iodovinyl)-1-trimethylsilyloxy-cyclohexane |
| 32 | 10 | 29 | 1-(trans-2-iodovinyl)-1-trimethylsilyloxy-cyclopentane |
| 33 | 11 | 30 | 1-(trans-2-tri-n-butylstannylvinyl)-1-trimethylsilyloxycycloheptane |
| 34 | 12 | 29 | 1R,3S-(and 1S,3R-) 1-(trans-2-iodovinyl)-1-trimethylsilyloxy-3-propylcyclopentane |
| 36 | 7 | 29 | 1R,2R-(and 1S,2S-) 1-(trans-2-iodovinyl)-1-trimethylsilyloxy-2-butylcyclopentane |
| 37 | 14 | 29 | 1R,2S-(and 1S,2R-) 1-(trans-2-iodovinyl)-1-trimethylsilyloxy-2-butylcyclohexane |
| 38 | 15 | 29 | 1R,2R-(and 1S,2S-) 1-(trans-2-iodovinyl)-1-trimethylsilyloxy-2-butylcyclohexane |
| 39 | 16 | 30 | 1R,2S-(and 1S,2R-) 1-trans-2-tri-n-butylstannylvinyl)-1-trimethylsilyloxy)-2-(3-trifluoromethylphenoxy)cyclopentane |
| 40 | 17 | 30 | 1R,2R-(and 1S,2S-) 1-(trans-2-tri-n-butylstannylvinyl)-1-trimethylsilyloxy-2-(3-trifluoromethylphenoxy)cyclopentane |
| 41 | 18 | 29 | 1R,2S-(and 1S,2R-) 1-(trans-2-iodovinyl)-1-trimethylsilyloxy-2-(4-fluorophenoxy)-cyclopentane |
| 42 | 19 | 29 | 1R,2R-(and 1S,2S-) 1-(trans-2-iodovinyl)-1-trimethylsilyloxy-2-(4-fluorophenoxy)-cyclopentane |
| 43 | 20 | 30 | 1R,2S-(and 1S,2R-) 1-(trans-2-tri-n-butylstannylvinyl)-1-trimethylsilyloxy-2-(3-chlorophenoxy)cyclopentane |
| 44 | 21 | 30 | 1R,2R-(and 1S,2S-) 1-(trans-2-tri-n-butylstannylvinyl)-1-trimethylsilyloxy-2-(3-chlorophenoxy)cyclopentane |
| 45 | 22 | 29 | 1R,3S-(and 1S,3R-) 1-(trans-2-iodovinyl)-1-trimethylsilyloxy-3-methylcyclohexane |
| 46 | 23 | 29 | 1R,3R-(and 1S,3S-) 1-(trans-2-iodovinyl)-1-trimethylsilyloxy-3-methylcyclohexane |
| 47 | 24 | 30 | 1R,2S-(and 1S,2R-) 1-(3-tri-n-butylstannyl-2-trans-propenyl)-1-trimethylsilyloxy-2-butylcyclopentane |
| 48 | 25 | 30 | 1R,2R-(and 1S,2S-) 1-(3-tri-n-butylstannyl-2-trans-propenyl)-1-trimethylsilyloxy-2-butylcyclopentane |
| 49 | 26 | 30 | 1R,2S-(and 1S,2R-) 1-(3-tri-n-butylstannyl-2-trans-propenyl)-1-trimethylsilyloxy-2-(3-trifluoromethylphenoxy)cyclopentane |
| 50 | 27 | 30 | 1R,2R-(and 1S,2S-) 1-(3-tri-n-butylstannyl-2-trans-propenyl)-1-trimethylsilyloxy-2-(3-trifluoromethylphenoxy)cyclopentane |

Preparation of 1-(3-Tri-n-butylstannyl-2-trans-propenyl)-1-trimethylsilyloxycyclohexane To a stirred mixture of 31.5 g of 1-propargyl-1-trimethylsilyloxycyclohexane and 150 mg of azobisisobutyronitrile is added 41 ml of tri-n-butyltin hydride. The stirred mixture is heated to about 80° C. The initial exothermic reaction is moderated, and the temperature is subsequently maintained at 130°–135° C. for one hour.

The product is distilled to afford 56 g of colorless liquid, bp 150°–160° C. (0.15–0.3 mm), pmr (CDCl$_3$): 6.0 (multiplet, vinyl protons).

EXAMPLES 31-50

Using the procedure outlined above for Examples 28a, b, c and d, the acetylenic alcohols listed in Table II are converted to their corresponding acetylenic trimethylsilyloxy derivatives; these in turn using the procedure outlined above for Examples 29a and 29b, were converted to their corresponding trans-2-iodovinyl derivatives or using the procedure out above for Example 30, were converted to their corresponding trans-2-tri-n-butylstannyl derivatives (Table II).

EXAMPLE 51

Preparation of 2-(6-Carbotrimethylsilyloxyhex-2-cis-enyl)-4-trimethylsilyloxycyclopent-2-en-1-one To a solution of 1.0 g of 2-(6-carboxyhex-2-cis-enyl)-4-hydroxycyclopent-2-en-1-one in 12.5 ml of dry pyridine at 15° C. under argon is added with stirring 3.3 ml of hexamethyldisilazane (HMDS) followed by dropwise addition of 1.6 ml of trimethylchlorosilane (TMCS). The resulting mixture is stirred at ambient temperature for one hour then taken to dryness (vac. pump). The residue is taken up in hexanes and filtered thru Celite. Evaporation of the mother liquor followed by two evaporations with toluene furnished 1.5 g (96%) of pure 2-(6-carbotrimethylsilyloxyhex-2-cis-enyl)-4-trimethylsilyloxycyclopent-2-en-1-one.

EXAMPLE 52

Preparation of 2-(6-Carbotrimethylsilyloxyhexyl)-4-trimethylsilyloxycyclopent-2-en-1-one To a solution of 1.0 g of 2-(6-carboxyhexyl)-4-hydroxycyclopent-2-en-1-one in 12.5 ml of dry pyridine at 15° C. under argon, is added with stirring 3.3 ml of hexamethyldisilazane followed by dropwise addition of 1.6 ml of trimethylchlorosilane. The resulting mixture is stirred at ambient temperature for one hour and then taken to dryness. The residue is taken up in hexane and filtered through diatomaceous earth. Evaporation of the mother liquor followed by two evaporations with toluene gives pure product.

EXAMPLE 53

Preparation of 2-(6 carbomethoxyhexyl)-4(R)-trimethylsilyloxycyclopent-2-en-1-one To a solution of 1.0 g of 2-(6-carbomethylhexyl)-4(R)-hydroxycyclopent-2-en-1-one [R. Pappo, et al., Tetrahedron Letters, 943 (1973)] in 12.5 ml of dry pyridine at 15° under argon was added with stirring 3.3 ml (24 mmoles) of hexamethyldisilazane (HMDS) followed by dropwise addition of 1.6 ml (20.5 mmoles) of trimethylchlorosilane (TMCS). The resulting mixture was stirred at ambient temperature for 1 hour then taken to dryness (vac. pump). The residue is taken up in hexanes and filtered thru Celite. Evaporation of the mother liquor followed by two evaporations with toluene furnished 2-(6-carbomethoxyhexyl)-4(R)-trimethylsilyloxycyclopent-2-en-1-one.

EXAMPLE 54

Preparation of 2-(6-carbomethoxyhexyl)-4(S)-trimethylsilyloxycyclopent-2-en-1-one In the manner described in Example 239, treatment of 2-(6-carbomethoxyhexyl)-4(S)-hydroxycyclopent-2-en-1-one [R. Pappo, et al., Tetrahedron Letters, 943 (1973)] with hexamethyldisilazane and trimethylsilylchloride gives the subject product.

EXAMPLE 55

Preparation of 5-chloro-1-(2-furyl)-1-pentanol

To a stirred suspension of 2-furyllithium (prepared from 0.53 moles of n-butyllithium and 39.5 g of furan by the procedure of J. Org. Chem., 27, 1216 (1962)) in 350 ml of ether and ca. 200 ml of hexane at −78° is added a solution of 57.9 g of 5-chloropentanol (Chem. Abstr., 59, 7579F (1963)) in 80 ml of ether during 25 minutes. The mixture is warmed to 0° during 20 minutes, stirred at 0° for 15 minutes, and treated with 140 ml of saturated ammonium chloride. The ether phase is washed with water and brine, dried over magnesium sulfate and potassium carbonate mixture, and concentrated to give a liquid, pmr spectrum (CDCl$_3$): δ3.59 (triplet, C$\underline{H}_2$Cl$_2$) and 4.70 (triplet, CH$_2$C$\underline{H}$OH).

EXAMPLE 56

Preparation of 5-(carbethoxymethylthio)-1-(2-furyl)-1-pentanol

To a stirred, refluxing mixture of 76 g of ethyl mercaptoacetate, 79.5 g of 5-chloro-1-(2-furyl)-1-pentanol (Example), and 10 ml of 1.5 M sodium ethoxide in ethanol is added an additionan 300 ml of 1.5 M sodium ethoxide during 15 minutes. The resulting mixture is stirred at reflux for 3 hours, cooled, and concentrated to remove most of the ethanol. The residue is partitioned with ether and water. The ether phase is washed with brine and dried over potassium carbonate. The solution is concentrated, diluted with xylene, and again concentrated to give an oil, pmr spectrum (CDCl$_3$): δ3.24 (singlet, —S—CH$_2$CO$_2$C$_2$H$_5$) and 4.70 (triplet, CH$_2$CHOH).

EXAMPLE 57

Preparation of 2-(6-carboxy-5-thiahexyl)-4-hydroxycyclopent-2-en-1-one

A stirred solution of 125 g of 5-(carbethoxymethylthio)-1-(2-furyl)-1-pentanol (Example), 22.4 g of sodium formate, 250 ml of formic acid, and 400 mg of hydroquinone in 2000 ml of dioxane and 1330 ml of water is refluxed for 20 hours.

The solution, containing crude 3-hydroxy-2-[4-(carbethoxymethylthio)butyl]cyclopent-4-en-1-one, is cooled and treated during 10 minutes with 75 ml of sulfuric acid (d = 1.84) with stirring. The stirred solution is refluxed for 16 hours, cooled, saturated with sodium chloride, and extracted with ethyl acetate. The extract is washed with brine, dried over magnesium sulfate, and concentrated. The residue is subjected to chromatography on silica gel with chloroform progressively enriched in ether, ether, and ether progressively enriched in acetone to afford the subject compound as an oil, pmr spectrum (CDCl$_3$): δ3.24 (singlet, —S—CH$_2$—CO$_2$C$_2$H$_5$), 5.0 (broad singlet —CHOH—).

EXAMPLE 58

Preparation of 2-(6-carbotrimethylsilyloxy-5-thiahexyl)-4-trimethylsiloxycyclopent-2-en-1-one To a stirred solution of 28.4 g of 4-hydroxy-2-[4-(carboxymethylthio)butyl]cyclopent-2-en-1-one (Example) and 76 ml of hexamethyldisilazane in 330 ml of pyridine at 5° is added 38 ml of chlorotrimethylsilane during 5 minutes. The mixture is stirred at ambient temperature for 3.5 hours, at 45° for 5 minutes, and then evaporated to remove solvent. The residue is stirred with 1000 ml of petroleum ether and filtered. The filtrate is treated with charcoal and filtered; this filtrate is concentrated with the aid of toluene to give a liquid, pmr spectrum (CDCl$_3$): δ0.18 (singlet, trimethylsiloxy group) and 0.28 (singlet, trimethylsiloxycarbonyl group).

EXAMPLE 59

Preparation of 4-chloro-1-(2-furyl)-1-butanol

To a stirred suspension of 2-furyllithium (prepared from 0.53 moles of n-butyllithium and 39.5 g of furan by the procedure of J. Org. Chem., 27, 1216 (1962)) in 350 ml of ether and ca. 200 ml of hexane at −78° is added a solution of 57.9 g of 4-chlorobutanol (Chem. Abstr., 59, 7579F (1963)) in 80 ml of ether during 25 minutes. The mixture is warmed to 0° during 20 minutes, stirred at 0° for 15 minutes, and treated with 140 ml of saturated ammonium chloride. The ether phase is washed with water and brine, dried over magnesium sulfate and potassium carbonate mixture, and concentrated to give a liquid, pmr spectrum (CDCl$_3$): δ3.59 (triplet, CH$_2$Cl) and 4.70 (triplet, CH$_2$CHOH).

EXAMPLE 60

Preparation of 4-carbethoxymethylthio)-1-(2-furyl)-1-butanol

To a stirred, refluxing mixture of 76 g of ethyl mercaptoacetate, 79.5 g of 4-chloro-1-(2-furyl)-1-butanol (Example), and 10 ml of 1.5 M sodium ethoxide in ethanol is added an additional 300 ml of 1.5 M sodium ethoxide during 15 minutes. The resulting mixture is stirred at reflux for 3 hours, cooled, and concentrated to remove most of the ethanol. The residue is partitioned with ether and water. The ether phase is washed with brine and dried over potassium carbonate. The solution is concentrated, diluted with xylene, and again concentrated to give an oil, pmr spectrum ($CDCl_3$): $\delta 3.24$ (singlet, $-S-CH_2-CO_2C_2H_5$) and 4.70 (triplet, $CH_2CHOH$).

EXAMPLE 61

Preparation of 2-(5-carboxy-4-thiapentyl)-4-hydroxycyclopent-2-en-1-one

A stirred solution of 125 g of 4-(carbethoxymethylthio)-1-(2-furyl)-1-butanol (Example), 22.4 g of sodium formate, 250 ml of formic acid, and 400 mg of hydroquinone in 2000 ml of dioxane and 1330 ml of water is refluxed for 20 hours.

The solution, containing crude 3-hydroxy-2-[3-(carbethoxymethylthio)propyl]cyclopent-4-en-1-one, is cooled and treated during 10 minutes with 75 ml of sulfuric acid (d=1.84) with stirring. The stirred solution is refluxed for 16 hours, cooled, saturated with sodium chloride, and extracted with ethyl acetate. The extract is washed with brine, dried over magnesium sulfate, and concentrated. The residue is subjected to chromatography on silica gel with chloroform progressively enriched in ether, ether, and ether progressively enriched in acetone to afford the subject compound as an oil.

EXAMPLE 62

Preparation of 2-(5-carbotrimethylsilyloxy-4-thiapentyl)-4-trimethylsiloxycyclopent-2-en-1-one To a stirred solution of 28.4 g of 4-hydroxy-2-[4-(carboxymethylthio)butyl]cyclopent-2-en-1-one (Example) and 76 ml of hexamethyldisilazane in 330 ml of pyridine at 5° is added 38 ml of chlorotrimethylsilane during 5 minutes. The mixture is stirred at ambient temperature for 3.5 hours, at 45° for 5 minutes, and then evaporated to remove solvent. The residue is slurried with 1000 ml of petroleum ether and filtered. The filtrate is treated with charcoal and filtered; this filtrate is concentrated with the aid of toluene to give a liquid, pmr spectrum ($CDCl_3$): $\delta 0.18$ (singlet, trimethylsiloxy group) and 0.28 (singlet, trimethylsiloxycarbonyl group).

EXAMPLE 63

Preparation of nat(and ent)-11α,15-Dihydroxy-9-oxo-15,16-tetramethylene-17,18,19,20-tetranor-5-cis,13-trans-prostadienoic Acid A 6.48 ml solution of 2.3 M n-butyllithium in hexane is added, at 0° C. under nitrogen, to a solution of 1.64 g of thiophenol in 45 ml of ether. After one hour at 0° C. a solution of 5.85 g of tri-n-butylphosphine-cooper complex in 140 ml of ether is added and the mixture is stored in a freezer overnight. To a solution of 4.54 g or 1-(trans-2-iodovinyl)-1-trimethylsilyloxycyclohexane in 8 ml of toluene at −40° C. under nitrogen is added, with stirring, 35 ml of a solution of t-butyllithium. After 90 minutes a few ml of ether is added and the mixture is stirred at room temperature for 15 minutes. This solution is recooled to −78° C. and the copper solution is cooled to −78° C. and transferred to the vinyl lithium solution in a steady stream. The solution is stirred at −78° C. for 35 minutes and a solution of 5.0 g of 2-(6-carbotrimethylsilyloxyhex-2-cis-enyl)-4-trimethylsilyloxycyclopent-2-en-1-one (Ex. 51) in 10 ml of ether is added. The mixture is placed in a bath at −45° C., stirred for 3 hours and allowed to warm to −20° C. over 15 minutes. A solution of 2.0 g of acetic acid in 5 ml of ether is added after recooling to −40° C. Saturated $NH_4Cl$ solution is added followed by a small amount of dilute HCl. The mixture is poured into ether. The aqueous layer is extracted with ether. The combined ether solutions are washed with dilute HCl, twice with water and then with saturated NaCl. The ether is dried over $MgSO_4$ and the solvent is removed giving a yellow oil. This is stirred in 50 ml of acetic acid:tetrahydrofuran:water (4:2:1) for 45 minutes and then poured into water. The solution is extracted with ether and the ether solution is washed with water twice and once with brine. The solution is dried over magnesium sulfate and the solvent is removed. The residue is chromatographed on a dry column of silica gel eluting with ethyl acetate containing 1% acetic acid to give 2.15 g of nat(and ent)-11α,15-dihydroxy-9-oxo-15,16-tetramethylene-17,18,19,20-tetranor-5-cis,13-trans-prostadienoic acid.

EXAMPLE 64

Preparation of nat(and ent)-11α,15-Dihydroxy-9-oxo-15,16-tetramethylene-17,18,19,20-tetranor-13-trans-prostenoic Acid To a solution of 1.01 g of thiophenol in 30 ml of ether under nitrogen at 0° C., is added with stirring, 4.0 ml of 2.3 M n-butyllithium. The mixture is stirred for one hour and then a solution of 3.61 g of copper tri-n-butyl phosphine complex in 85 ml of ether is added.

To 2.98 g of 1-(2-trans-iodovinyl)-1-trimethylsilyloxycyclohexane in 8 ml of toluene at −45° C., under nitrogen, is added with stirring 23 ml of 0.8 M t-butyllithium. Stirring and cooling are continued for 75 minutes. The cooling bath is removed and the solution is stirred for 10 minutes. A 5 ml portion of ether is added and the solution is cooled to −78° C. The copper solution is cooled to −78° C. and then added to the vinyl lithium solution via a double needle. After 30 minutes, a solution of 3.4 g of 1-(6-carbotrimethylsilyloxyhexyl)-4-trimethylsilyloxycyclopent-2-en-1-one in ether is added. The solution is then placed in a dry ice-acetonitrile bath at −45° C. to −50° C. and stirred for 3 hours. The solution is allowed to warm to −20° C. over 20 minutes and stirred at −20° C. for 10 minutes. To this solution is added 5 ml of acetic acid in 5 ml of ether followed by 0.5 M hydrochloric acid. The solution is poured into water and extracted with ether. The ether solution is washed with water and dried with magnesium sulfate. The solvent is removed followed by removal of most of the thiophenol. The residue is dissolved in 100 ml of a mixture of acetic acid, tetrahydrofuran and water and stirred for one hour. The mixture is poured into water and extracted with ether. The ether extract is washed several times with water and dried with magnesium sulfate. The ether is removed leaving a yellow oil. the oil is chromatographed on a dry silica gel column eluting eith ether:ethyl acetate 1:1. The product is isolated as a light green-yellow oil which solidifies on drying to give an off-white solid.

EXAMPLE 65

Preparation of nat(and ent)-11α,16-Dihydroxy-9-oxo-16,17-tetramethylene-18,19,20-trinor-5-cis,13-trans-prostadienoic Acid A solution of 10.3 g of 1-(3-tri-n-butylstannyl-2-trans-propenyl)-1-trimethylsilyloxycyclohexane (Ex. 30) in 7 ml of tetrahydrofuran is cooled in a dry ice-acetone bath under nitrogen and treated with 8.6 ml of 2.5 M n-butyllithium in hexane during 10 minutes. The resulting solution is stirred at −40° C. for one hour, then at −20° C. to −30° C. for another hour, recooled to −78° C., and treated during 10 minutes with the solution of 2.68 g of copper pentyne, 7.87 ml of hexamethylphosphorus triamide and 19 ml of tetrahydrofuran. The resulting solution is stirred at −70° C. to −50° C. for one hour, recooled to −78° C., and treated with a solution of 5.8 g of 2-(6-carbotrimethylsilyloxyhex-2-cis-enyl)-4-trimethylsilyloxycyclopent-2-en-1-one (Ex. 51) in 12 ml of tetrahydrofuran during 10 minutes. The mixture is then stirred at −40° C. to −50° C. for 40 minutes, then at −20° C. to −25° C. for 25 minutes, recooled to −40° C., and poured into 500 ml of cold, saturated ammonium chloride solution and 300 ml of ether. To the resulting mixture is added 8 ml of glacial acetic acid and it is extracted with ether. The combined ether extract is washed with water, diluted hydrochloric acid, filtered through Celite and washed again with water and saturated sodium chloride solution. Evaporation of the solvents at reduced pressure gives 15.2 g of oil. A solution of this crude oil in 175 ml of glacial acetic acid:tetrahydrofuran:water (4:2:1) is stirred at room temperature under nitrogen for 50 minutes. To the mixture is added 150 ml of toluene and concentrated at reduced pressure. The crude product obtained is purified by chromatography on silica gel to give nat(and ent)-11α,16-dihydroxy-9-oxo-16,17-tetramethylene-18,19,20-trinor-5-cis,13-trans-prostadienoic acid.

EXAMPLE 66

Preparation of nat-15S,16R(and ent-15R,16S) and nat-15R,16S-(and ent-15S,16R)-11α,15-Dihydroxy-9-oxo-15,16-trimethylene-13-trans-5-cis-prostadienoic Acid To a solution of 1.44 g of thiophenol in 40 ml of ether under nitrogen at 0° C. is added with stirring, 5.65 ml of 2.3 M n-butyllithium. After one hour of stirring at 0° C. a solution of bis tri-n-butylphosphine copper iodide complex in 100 ml of ether is added and the solution is stored overnight in a freezer.

To 4.76 g of 1R,2S(and 1S,2R)-1-(trans-2-iodovinyl)-1-trimethylsilyloxy-2-butylcyclopentone in 10 ml of toluene under nitrogen at −45° C., is added with stirring, 32.5 ml of of 0.8 M t-butyllithium. After stirring for 90 minutes at −45° C. the solution is removed from the cooling bath and stirred 15 minutes. The solution is cooled to −78° C. The copper solution is cooled to −78° C. and then added to the vinyl lithium solution. After 30 minutes a solution of 4.4 g of 1-(6-carbotrimethylsilyloxyhex-2-cis-enyl)-4-trimethylsilyloxycyclopent-2-en-1-one in 2- ml of ether is added. The solution is stirred at −45° C. for 3 hours and then allowed to warm to −20° C. over a 30 minute period. The solution is stirred at −20° C. for 15 minutes and then a solution of 2.5 ml of acetic acid in 15 ml of ether is added followed by dilute hydrochloric acid. The mixture is extracted with ether. The ether extract is washed with saturated sodium chloride solution and dried with magnesium sulfate. The solvent is removed giving a yellow oil. This oil is stirred in 70 ml of acetic acid:tetrahydrofuran:water (4:2:1) for one hour, poured into water and extracted with ether. The extract is dried with magnesium sulfate and the ether is removed. The residue is chromatographed on a dry column of silica gel, eluting with ether to give the separated isomers.

EXAMPLES 68–192

In the manner described hereinabove for Examples 63–66, the 9-oxo-prostaglandins shown in Table III are prepared from the indicated vinyl iodide or vinyl tin compounds and the indicated cyclopent-2-en-1-ones, these were first converted to their corresponding bis-trimethylsilyloxy derivatives as described hereinabove for Examples 51 and 52. In those cases where two diastereoisomers are formed in the conjugate-addition, only one of the diastereoisomers is listed in Table III. It should be understood that the other diastereoisomer is also formed which in its nat and ent forms has an opposite (mirror image) configuration at the assymmetric carbon atoms on the -chain (the chain containing $C_{13}$ . . . $C_{14}$ etc.) to that of the respective nat and ent forms of the listed diastereoisomer; both of these diastereoisomers are claimed in this invention as well as their component enantiomers.

TABLE III

| Example | Vinyl Iodide or Vinyl Tin of Example | Cyclopent-2-en-1-one | Product 9-oxo-prostaglandin and its diastereoisomer and ethyl ester where applicable (see hereinabove) |
|---|---|---|---|
| 68 | 29a | 2-(6-carboxyhexyl)-4-hydroxycyclopent-2-en-1-one | nat-15S,16R-(and ent-15R,16S)-11α,-15-dihydroxy-9-oxo-15,16-trimethylene-13-trans-prostenoic acid |
| 69 | 36 | 2-(6-carboxyhexyl)-4-hydroxycyclopent-2-en-1-one | nat-15S,16S-(and ent-15R,16R)-11α,-15-dihydroxy-9-oxo-15,16-trimethylene-13-trans-prostenoic acid |
| 70 | 31 | 2-(6-carboxyhexyl)-4-hydroxycyclopent-2-en-1-one | nat-(and ent)-11α,15-dihydroxy-9-oxo-15,16-tetramethylene-17,18,19,-20-tetranor-13-trans-prostenoic acid |
| 71 | 32 | 2-(6-carboxyhexyl)-4-hydroxycyclopent-2-en-1-one | nat-(and ent)-11α,15-dihydroxy-9-oxo-15,16-trimethylene-17,18,19,20-tetranor-13-trans-prostenoic acid |
| 72 | 33 | 2-(6-carboxyhexyl)-4-hydroxycyclopent-2-en-1-one | nat-(and ent)-11α,15-dihydroxy-15,-16-pentamethylene-17,18,19,20-tetranor-13-trans-prostenoic acid |
| 73 | 34 | 2-(6-carboxyhexyl)-4-hy- | nat-15S,17R-(and ent-15R,17S)-11α,- |

TABLE III-continued

| Example | Vinyl Iodide or Vinyl Tin of Example | Cyclopent-2-en-1-one | Product 9-oxo-prostaglandin and its diastereoisomer and ethyl ester where applicable (see hereinabove) |
|---|---|---|---|
| | | droxycyclopent-2-en-1-one | 15-dihydroxy-9-oxo-15,17-dimethylene-13-trans-prostenoic acid |
| 74 | 35 | 2-(6-carboxyhexyl)-4-hydroxycyclopent-2-en-1-one | nat-15S,17S-(and ent-15R,17R)-11α,15-dihydroxy-9-oxo-15,17-dimethylene-13-trans-prostenoic acid |
| 75 | 37 | 2-(6-carboxyhexyl)-4-hydroxycyclopent-2-en-1-one | nat-15S,16R-(and ent-15R,16S)-11α,15-dihydroxy-9-oxo-15,16-tetramethylene-13-trans-prostenoic acid |
| 76 | 38 | 2-(6-carboxyhexyl)-4-hydroxycyclopent-2-en-1-one | nat-15S,16S-(and ent-15R,16R)-11α,15-dihydroxy-9-oxo-15,16-tetramethylene-13-trans-prostenoic acid |
| 77 | 39 | 2-(6-carboxyhexyl)-4-hydroxycyclopent-2-en-1-one | nat-15R,16S-(and ent-15S,16R)-11α,15-dihydroxy-9-oxo-15,16-trimethylene-16-(3-trifluoromethylphenoxy)-17,18,19,20-tetranor-13-trans-prostenoic acid |
| 78 | 40 | 2-(6-carboxyhexyl)-4-hydroxycyclopent-2-en-1-one | nat-15R,16R-(and ent-15S,16S)-11α,15-dihydroxy-9-oxo-15,16-trimethylene-16-16-(3-trifluoromethylphenoxy)-17,18,19,20-tetranor-13-trans-prostenoic acid |
| 79 | 30 | 2-(6-carboxyhexyl)-4-hydroxycyclopent-2-en-1-one | nat-(and ent)-11α,16-dihydroxy-9-oxo-16,17-tetramethylene-18,19,20-trinor-13-trans-prostenoic acid |
| 80 | 41 | 2-(6-carboxyhexyl)-4-hydroxycyclopent-2-en-1-one | nat-15R,16S-(and ent-15S,16R)-11α,15-dihydroxy-9-oxo-15,16-trimethylene-16-(4-fluorophenoxy)-17,18,19,20-tetranor-13-trans-prostenoic acid |
| 81 | 42 | 2-(6-carboxyhexyl)-4-hydroxycyclopent-2-en-1-one | nat-15R,16R-(and ent-15S,16S)-11α,15-dihydroxy-9-oxo-15,16-trimethylene-16-(4-fluorophenoxy)-17,18,19,20-tetranor-13-trans-prostenoic acid |
| 82 | 43 | 2-(6-carboxyhexyl)-4-hydroxycyclopent-2-en-1-one | nat-15R,16S-(and ent-15S,16R)-11α,15-dihydroxy-9-oxo-15,16-trimethylene-16-(3-chlorophenoxy)-17,18,19,20-tetranor-13-trans-prostenoic acid |
| 83 | 44 | 2-(6-carboxyhexyl)-4-hydroxycyclopent-2-en-1-one | nat-15R,16R-(and ent-15S,16S)-11α,15-dihydroxy-9-oxo-15,16-trimethylene-16-(3-chlorophenoxy)-17,18,19,20-tetranor-13-trans-prostenoic acid |
| 84 | 45 | 2-(6-carboxyhexyl)-4-hydroxycyclopent-2-en-1-one | nat-15S,17R-(and ent-15R,17S)-11α,15-dihydroxy-9-oxo-15,17-trimethylene-19,20-dinor-13-trans-prostenoic acid |
| 85 | 46 | 2-(6-carboxyhexyl)-4-hydroxycyclopent-2-en-1-one | nat-15S,17S-(and ent-15R,17R)-11α,15-dihydroxy-9-oxo-15,17-trimethylene-19,20-dinor-13-trans-prostenoic acid |
| 86 | 47 | 2-(6-carboxyhexyl)-4-hydroxycyclopent-2-en-1-one | nat-16R,17S-(and ent-16S,17R)-11α,16-dihydroxy-9-oxo-16,17-trimethylene-20-methyl-13-trans-prostenoic acid |
| 87 | 48 | 2-(6-carboxyhexyl)-4-hydroxycyclopent-2-en-1-one | nat-16R,17R-(and ent-16S,17/)-11α,16-dihydroxy-9-oxo-16,17-trimethylene-20-methyl-13-tans-prostenoic acid |
| 88 | 49 | 2-(6-carboxyhexyl)-4-hydroxycyclopent-2-en-1-one | nat-16R,17S-(and ent-16S,17R)-11α,16-dihydroxy-9-oxo-16,17-trimethylene-17-(3-trifluoromethylphenoxy)-18,19,20-trinor-13-trans-prostenoic acid |
| 89 | 50 | 2-(6-carboxyhexyl)-4-hydroxycyclopent-2-en-1-one | nat-16R,17R-(and ent-16S,17S)-11α,16-dihydroxy-9-oxo-16,17-trimethylene-17-(3-trifluormethylphenoxy)-18,19,20-trinor-13-trans-prostenoic acid |
| 90 | 29a | 2-(5-carboxypentyl)-4-hydroxycyclopent-2-en-1-one | nat-15S,16R-(and ent-15R,16S)-11α,15-dihydroxy-9-oxo-15,16-trimethylene-2-nor-13-trans-prostenoic acid |
| 91 | 36 | 2-(5-carboxypentyl)-4-hydroxycyclopent-2-en-1-one | nat-15S,16S-(and ent-15R,16R)-11α,15-dihydroxy-9-oxo-15,16-trimethylene-2-nor-13-trans-prostenoic acid |
| 92 | 31 | 2-(5-carboxypentyl)-4-hydroxycyclopent-2-en-1-one | nat-(and ent)-11α,15-dihydroxy-9-oxo-15,16-tetramethylene-2,17,18-19,20-pentanor-13-trans-prostenoic acid |
| 93 | 32 | 2-(5-carboxypentyl)-4-hydroxycyclopent-2-en-1-one | nat-(and ent)-11α,15-dihydroxy-9-oxo-15,16-trimethylene-2,17,18,-19,20-pentanor-13-trans-prostenoic |

TABLE III-continued

| Example | Vinyl Iodide or Vinyl Tin of Example | Cyclopent-2-en-1-one | Product 9-oxo-prostaglandin and its diastereoisomer and ethyl ester where applicable (see hereinabove) |
|---|---|---|---|
| 94 | 33 | 2-(5-carboxypentyl)-4-hydroxycyclopent-2-en-1-one | nat-(and ent)-11α,15-dihydroxy-9-oxo-15,16-pentamethylene-2,17,18-19,20-pentanor-13-trans-prostenoic acid |
| 95 | 34 | 2-(5-carboxypentyl)-4-hydroxycyclopent-2-en-1-one | nat-15S,17R-(and ent-15R,17S)-11α,15-dihydroxy-9-oxo-15,17-dimethylene-2-nor-13-trans-prostenoic acid |
| 96 | 35 | 2-(5-carboxypentyl)-4-hydroxycyclopent-2-en-1-one | nat-15S,17S-(and ent-15R,17R)-11α,15-dihydroxy-9-oxo-15,17-dimethylene-2-nor-13-trans-prostenoic acid |
| 97 | 39 | 2-(5-carboxypentyl)-4-hydroxycyclopent-2-en-1-one | nat-15R,16S-(and ent-15S,16R)-11α,15-dihydroxy-9-oxo-15,16-trimethylene-16-(3-trifluormethylphenoxy)-2,17,18,19,20-pentanor-13-trans-prostenoic acid |
| 98 | 40 | 2-(5-carboxypentyl)-4-hydroxcylopent-2-en-1-one | nat-15R,16R-(and ent-15S,16S)-11α,15-dihydroxy-9-oxo-15,16-trimethylene-16-(3-trifluormethylphenoxy)-2,17,18,19,20-pentanor-13-trans-prostenoic acid |
| 99 | 29a | 2-(7-carboxyheptyl)-4-hydroxycyclopent-2-en-1-one | nat-15S,16R-(and ent-15R,16S)-11α,15-dihydroxy-9-oxo-15,16,-trimethylene-1-homo-13-trans-prostenoic acid |
| 100 | 36 | 2-(7-carboxyheptyl)-4-hydroxycyclopent-2-en-1-one | nat-15S,16S-(and ent-15R,16R)-11α,15-dihydroxy-9-oxo-15,16-trimethylene-1-homo-13-trans-prostenoic acid |
| 101 | 31 | 2-(7-carboxyheptyl)-4-hydroxycyclopent-2-en-1-one | nat-(and ent)-11α,15-dihydroxy-9-oxo-15,16-tetramethylene-17,18,19,20-tetranor-1-trans-13-trans-prostenoic acid |
| 102 | 37 | 2-(7-carboxyheptyl)-4-hydroxycyclopent-2-en-1-one | nat-15S,16R-(and ent-15R,16S)-11α,15-dihydroxy-9-oxo-15,16-tetramethylene-1-homo-13-trans-prostenoic acid |
| 103 | 38 | 2-(7-carboxyheptyl)-4-hydroxycyclopent-2-1-one | nat-15S,16S-(and ent-15R,16R)-11α,15-dihydroxy-9-oxo-15,16-tetramethylene-1-homo-13-trans-prostenoic acid |
| 104 | 41 | 2-(7-carboxyheptyl)-4-hydroxcylopent-2-en-1-one | nat-15R,16S-(and ent-15S,16R)-11α,15-dihydroxy-9-oxo-15,16-trimethylene-16-(4-fluorophenoxy)-1-homo-17,18,19,20-tetranor-13-trans-prostenoic acid |
| 105 | 42 | 2(7-carboxyheptyl)-4-hydroxycyclopent-2-en-1-one | nat-15R,16R-(and ent-15S,16S)-11α,15-dihydroxy-9-oxo-15,16-trimethylene-16-(4-fluorophenoxy)-1-homo-17,18,19,20-tetranor-13-trans-prostenoic acid |
| 106 | 45 | 2-(8-carboxyoctyl)-4-hydroxycyclopent-2-en-1-one | nat-15 S,17R-(and ent-15R,17S)-11α,15-dihydroxy-9-oxo-15,17-trimethylene-19,20-dinor-1a,1b-dihomo-13-trans-prostenoic acid |
| 107 | 46 | 2-(8-carboxyoctyl)-4-hydroxycyclopent-2-en-1-one | nat-15S,17S-(and ent-15R,17R)-11α,15-dihydroxy-9-oxo-15,17-trimethylene-19,20-dinor-1a,1b-dihomo-13-trans-prostenoic acid |
| 108 | 47 | 2-(8-carboxyoctyl)-4-hydroxycyclopent-2-en-1-one | nat-16R,17S-(and ent-16S,17R)-11α,16-dihydroxy-9-oxo-16,17-trimethylene-20-methyl-1a,1b-dihomo-13-trans-prostenoic acid |
| 109 | 48 | 2-(8-carboxyoctyl)-4-hydroxycyclopent-2-en-1-one | nat-16R,17R-(and ent-16S,17S)-11α,16-dihydroxy-9-oxo-16,17-trimethylene-20-methyl-1a,1b-dihomo-13-trans-prostenoic acid |
| 110 | 49 | 2-(8-carboxyoctyl)-4-hydroxycyclopent-2-en-1-one | nat-16R,17S-(and ent-16S,17R)-11α,16-dihydroxy-9-oxo-16,17-trimethylene-17-(3-trifluoromethylphenoxy)-18,19,20-trinor-1a,1b-dihomo-13-trans-prostenoic acid |
| 111 | 50 | 2-(8-carboxyoctyl)-4-hydroxycyclopent-2-en-1-one | nat-16R,17R-(and ent-16S,17S)-11α,16-dihydroxy-9-oxo-16,17-trimethylene-17-(3-trifluoromethylphenoxy)-18,19,20-trinor-1a,1b-dihomo-13-trans-prostenoic acid |
| 112 | 29a | 2-(6-carboxyhex-2-cis-enyl)-4-hydroxycyclopent-2-en-1-one | nat-15S,16R-(and ent-15R,16S)-11α,15-dihydroxy-9-oxo-15,16-trimethylene-13-trans-5-cis-prostadienoic acid |
| 113 | 36 | 2-(6-carboxyhex-2-cis-enyl)-4-hydroxycyclo- | nat-15S,16S-(and ent-15R,16R)-11α,15-dihydroxy-9-oxo-15,16-trimethy- |

TABLE III-continued

| Example | Vinyl Iodide or Vinyl Tin of Example | Cyclopent-2-en-1-one | Product 9-oxo-prostaglandin and its diastereoisomer and ethyl ester where applicable (see hereinabove) |
|---|---|---|---|
| | | pent-2-en-1-one | lene-13-trans-5-cis-prostadienoic acid |
| 114 | 32 | 2-(6-carboxyhex-2-cis-enyl)-4-hydroxycyclopent-2-en-1-one | nat-(and ent)-11α,-15-dihydroxy-9-oxo-15,16-trimethylene-17,18,19,-20-tetranor-13-trans-5-cis-prostadienoic acid |
| 115 | 33 | 2-(6-carboxyhex-2-cis-enyl)-4-hdyroxycyclopent-2-en-1-one | nat-(and ent)-11α,15-dihydroxy-9-oxo-15,16-pentamethylene-17,18,-19,20 -tetranor-13-trans-5-cis-prostadienoic acid |
| 116 | 34 | 2-(6-carboxyhex-2-cis-enyl)-4-hydroxycyclopent-2-en-1-one | nat-15S,17R-(and ent-15R,17S)-11α,-15-dihydroxy-9-oxo-15,17-dimethylene-13-trans-5-cis-prostadienoic acid |
| 117 | 35 | 2-(6-carboxyhex-2-cis-enyl)-4-hydroxycyclopent-2-en-1-one | nat-15S,17S-(and ent-15R,17R)-11α,-15-dihydroxy-9-oxo-15,17-dimethylene-13-trans-5-cis-prostadienoic acid |
| 118 | 37 | 2-(6-carboxyhex-2-cis-enyl)-4-hydroxycyclopent-2-en-1-one | nat-15S,16R-(and ent-15R,16S)-11α,-15-dihydroxy-9-oxo-15,16-tetramethylene-13-trans-5-cis-prostadienoic acid |
| 119 | 38 | 2-(6-carboxyhex-2-cis-enyl)-4-hydroxycyclopent-2-en-1-one | nat-15S,16S-(and ent-15R,16R)-11α,-15-dihydroxy-9-oxo-15,16-ttramethylene-13-trans-5-cis-prostadienoic acid |
| 120 | 39 | 2-(6-carboxyhex-2-cis-enyl)-4-hydroxycyclopent-2-en-1-one | nat-15R,16S-(and ent-15S,16R)-11α,-15-dihydroxy-9-oxo-15,16-trimethylene-16-(3-triluoromethylphenoxy)-17,18,19,20-tetranor-13-trans-5-cis-prostadienoic acid |
| 121 | 40 | 2-(6-carboxyhex-2-cis-enyl)-4-hydroxycyclopent-2-en-1-one | nat-15R,16R-(and ent-15S,16S)-11α,-15-dihydroxy-9-oxo-15,16-trimethylene-16-(3-trifluoromethylphenoxy)-17,18,19,20-tetranor-13-trans-5-cis-prostadienoic acid |
| 122 | 41 | 2-(6-carboxyhex-2-cis-enyl)-4-hydroxycycloent-2-en-1-one | nat-15R,16S(and ent-15S,16R)-11α,-15-dihydroxy-9-oxo-15,16-trimethylene-16-(4-fluorophenoxy)-17,18,19,-20-tetranor-13-trans-5-cis-prostadienoic acid |
| 123 | 42 | 2-(6-carboxyhex-2-cis-enyl)-4-hydroxycyclopent-2-en-1-one | nat-15R,16R-(and ent-15S,16S)-11α,-15-dihydroxy-9-oxo-15,16-trimethyl-lene-16-(4-fluorophenoxy)-17,18,19,-20-tetranor-13-trans-5-cis-prostadienoic acid |
| 124 | 43 | 2-(6-carboxyhex-2-cis-enyl)-4-hydroxycyclopent-2-en-1-one | nat-15R,16S-(and ent-15S,16R)-11α,-15-dihydroxy-9-oxo-15,16-trimethylene-16-(3-chlorophenoxy)-17,18,-19,20-tetranor-13-trans-5-cis-prostadienoic acid |
| 125 | 44 | 2-(6-carboxyhex-2-cis-enyl)-4-hydroxycyclopent-2-en-1-one | nat-15R,16R-(and ent-15S,16S)-11α,-15-dihydroxy-9-oxo-15,16-trimethylene-16-(3-chlorophenoxy)-17,18,-19,20-tetranor-13-trans-5-cis-prostadienoic acid |
| 126 | 45 | 2-(6-carboxyhex-2-cis-enyl)-4-hydroxycyclopent-2-en-1-one | nat-15S,17R-(and ent-15R,17S)-11α,-15-dihydroxy-9-oxo-15,17-trimethylene-19,20-dinor-13-trans-5-cis-prostadienoic acid |
| 127 | 46 | 2-(6-carboxyhex-2-cis-enyl)-4-hydroxycyclopent-2-en-1-one | nat-15S,17S-(and ent-15R,17R)-11α,-15-dihydroxy-9-oxo-15,17 -trimethylene-19,20 -dinor-13-trans-5-cis-prostadienoic acid |
| 128 | 47 | 2-(6-carboxyhex-2-cis-enyl)-4-hydroxycyclopent-2-en-1-one | nat-16R,17S-(and ent-16S,17R)-11α,-16-dihydroxy-9-oxo-16,17-trimethylene-20-methyl-13-trans-5-cis-prostadienoic acid |
| 129 | 48 | 2-(6-carboxyhex-2-cis-enyl)-4-hydroxycyclopent-2-en-1-one | nat-16R,17R-(and ent-16S,17S)-11α,-16-dihydroxy-9-oxo-16,17-trimethylene-20-methyl-13-trans-5-cis-prostadienoic acid |
| 130 | 49 | 2-(6-carboxyhex-2-cis-enyl)-4-hydroxycyclopent-2-en-1-one | nat-16R,17S-(and ent-16S,17R)-11α,-16-dihydroxy-9-oxo-16,17-trimethylene-17-(3-trifluoromethylphenoxy)-18,19,20-trinor-13-trans-5-cis prostadienoic acid |
| 131 | 50 | 2-(6-carboxyhex-2-cis-enyl)-4-hydroxycylo- | nat-16R,17R-(and ent-16S,17S)-11α,-16-dihydroxy-9-oxo-16,17-trimethy- |

TABLE III-continued

| Example | Vinyl Iodide or Vinyl Tin of Example | Cyclopent-2-en-1-one | Product 9-oxo-prostaglandin and its diastereoisomer and ethyl ester where applicable (see hereinabove) |
|---|---|---|---|
| | | pent-2-en-1-one | lene-17-(3-trifluoromethylphenoxy)-18,19,20-trinor-13-trans-5-cis-prostadienoic acid |
| 132 | 29a | 2-(8-carboxyoct-2-cis-enyl)-4-hydroxycylco-pent-2-en-1-one | nat-15S,16R-(and ent-15R,16S)-11α,-15dihydroxy-9-oxo-15,16-trimethy-lene-1a,1b-dihomo-13-trans-5-cis-prostadienoic acid |
| 133 | 36 | 2-(8-carboxyoct-2-cis-enyl)-4-hydroxycyclo-pent-2-en-1-one | nat-15S,16S-(and ent-15R,16R)-11α,-15-dihydroxy-9-oxo-15,16-trimethy-lene-1a,1b-dihomo-13-trans-5-cis-prostadienoic acid |
| 134 | 31 | 2-(8-carboxyoct-2-cis-enyl)-4-hydroxycyclo-pent-2-en-1-one | nat-(and ent)-11α,15-dihydroxy-9-oxo-15,16-tetramethylene-1a,1b-di-homo-17,18,19,20-tetranor-13-trans-5-cis-prostadienoic acid |
| 135 | 37 | 2-(8-carboxyoct-2-cis-enyl)-4-hydoxycyclo-pent-2-en-1-one | nat-15S,16R-(and ent-15R,16S)-11α,-15-dihydroxy-9-oxo-15,16-tetramethy-lene-1a,1b-dihomo-13-trans-5-cis-prostadienoic acid |
| 136 | 38 | 2-(8-carboxyoct-2-cis-enyl)-4-hydroxycyclo-pent-2-en-1-one | nat-15S,16S-(and ent-15R,16R)-11α,-15-hydroxy-9-oxo-15,16-tetramethy-lene-1a,1b-dihomo-13-cis-trans-5-cis-prostadienoic acid |
| 137 | 39 | 2-(8-carboxyoct-2-cis-enyl)-4-hydroxycyclo-pent-2-en-1-one | nat-15R,16S-(and ent-15S,16R)-11α,-15-dihydroxy-9-oxo-15,16-trimethyl-lene-16-(3-trifluoromethylphenoxy)-1a,1b-dihomo-17,18,19,20-tetranor-13-trans-5-cis-prostadienoic acid |
| 138 | 40 | 2-(8-carboxyoct-2-cis-enyl)-4-hydroxycyclo-pent-2-en-1-one | nat-15R,16R-(and ent-15S,16S)-11α, -15-dihydroxy-9-oxo-15,16-trimethyl-lene-16-(3-trifluoromethylphenoxy)-1a,1b-dihomo-17,18,19,20-tetranor-13-trans-5-cis-prostadienoic acid |
| 139 | 29a | 2-(6-carboxy-5-oxa-hex-yl)-4-hydroxycyclopent-2-en-1-one | nat-15S,16R-(and ent-15R,16S)-11α,-15-dihydroxy-3-oxo-9-oxo-15,16-tri-methylene-13-trans-prostenoic acid |
| 140 | 36 | 2-(6-carboxy-5-oxa-hex-yl)-4-hydroxycyclopent-2-en-1-one | nat-15S,16S-(and ent-15R,16R)-11α,-15-dihydroxy-3-oxa-9-oxo-15,16-tri-methylene-13-trans-prostenoic acid |
| 141 | 31 | 2-(6-carboxy-5-oxa-hex-yl)-4-hydroxycyclopent-2-en-1-one | nat-(and ent)-11α,15-dihydroxy-3-oxa-9-oxo-15,16-tetrametylene-17,18,19,20-tetranor-13-trans-prostenoic acid |
| 142 | 43 | 2-(6-carboxy-4-methyl-hex-2-cis-enyl)-4-hydroxy-cyclopent-2-en-1-one | nat-15R,16S-(and ent-15S,16 R)-11α,-15-dihydroxy-4-methyl-9-oxo-15,16-trimethylene-16-(3-chlorophenoxy)-17,18,19,20-tetranor-13-trans-prostenoic acid |
| 143 | 44 | 2-(6-carboxy-4-methyl-hex-2-cis-enyl)-4-hydroxy-cyclopent-2-en-1-one | nat-15R,16R-(and ent-15S,16S)-11α,-15-dihydroxy-4-methyl-9-oxo-15,16-trimethylene-16-(3-chlorophenoxy)-17,18,19,20-tetranor-13-trans-prostenoic acid |
| 144 | 45 | 2-(6-carboxy-4-methyl-hex-2-cis-enyl)-4-hydroxy-cyclopent-2-en-1-one | nat-15S,17R-(and ent-15R,17S)-11α,-15-dihydroxy-4-methyl-9-oxo-15,17-trimethylene-19,20-dinor-13-trans-prostenoic acid |
| 145 | 46 | 2-(6-carboxy-4-methyl-hex-2-cis-enyl)-4-hydroxy-cyclopent-2-en-1-one | nat-15S,17S-(and ent-15R,17R)-11α,-15-dihydroxy-4-methyl-9-oxo-15,17-trimethylene-19,20-dinor-13-trans-prostenoic acid |
| 146 | 47 | 2-(6-carboxy-4-methyl-hex-2-cis-enyl)-4-hydroxy-cyclopent-2-en-1-one | nat-16R,17S-(and ent-16S,17R)-11α,-16-dihydroxy-4-methyl-9-oxo-16,17-trimethylene-20-methyl-13-trans-prostenoic acid |
| 147 | 48 | 2-(6-carboxy-4-ethylhex-2-cis-enyl)-4-hydroxy-cyclopent-2-en-1-one | nat-16R,17R-(and ent-16S,17S)-11α,-16-dihydroxy-4-ethyl-9-oxo-16,17-trimethylene-20-methyl-13-trans-prostenic acid |
| 148 | 49 | 2-(6-carboxy-1 ethylhex-2-cis-enyl)-4-hydroxy-cyclopent-2-en-1-one | nat-16R,17S-(and ent-16S,17R)-11α,-16-dihydroxy-4-ethyl-9-oxo-15,17-trimethylene-17-(3-trifluoromethyl)-phenoxy)-18,19,20-trinor-3-trans-prostenoic acid |
| 149 | 50 | 2-(6-carboxy-4-ethylhex-2-cis-enyl)-4-hydroxy-cyclopent-2-en-1-one | nat-16R,17R-(and ent-16S,17S)-11α,-16-dihydroxy-4-ethyl-9-oxo-15,17-trimethylene-1-(3-trifluoromethyl-phenoxy)-18,19,20-trinor-13-trans- |

TABLE III-continued

| Example | Vinyl Iodide or Vinyl Tin of Example | Cyclopent-2-en-1-one | Product 9-oxo-prostaglandin and its diastereoisomer and ethyl ester where applicable (see hereinabove) |
| --- | --- | --- | --- |
|  |  |  | prostenoic acid |

EXAMPLES 150-167

In the manner of Examples 63, 64, 65 and 66, the 9-oxo-11α-hydroxy prostaglandin methyl esters listed in Table IV are prepared from the indicated cyclopent-2-en-1-one and vinyl iodide or vinyl tin compound.

In those cases where two diastereoisomers are formed in the conjugate-addition both are obtained in an optically active form and only one of the diastereoisomers is listed in Table IV. It should be understood that the other diastereoisomer is also formed which in its nat or ent forms has an opposite (mirror image) configuration at the assymmetric carbon atoms on the β-chain (the chain containing $C_{13}$-$C_{14}$... etc.) to that of the respective nat or ent forms of the listed diastereoisomer; both of these diastereoisomers are claimed in this invention.

EXAMPLES 168-179

In the manner of Examples 63 to 66, the 9-oxo-11α-hydroxy-3-thia prostaglandins listed herein below in Table IV are prepared from the indicated cyclopent-2-en-1-one and vinyl iodide or vinyl tin compound. Both diastereoisomers are formed although only one is listed in the Table.

TABLE IV

| Example | Vinyl Iodide or Vinyl Tin of Example | Cyclopent-2-en-1-one | Product optically active 9-oxo-prostaglandin and its optically active diastereoisomer |
| --- | --- | --- | --- |
| 150 | 29a | 2-(6-carbomethoxyhexyl)-4(S)-trimethylsilyloxy-cyclopent-2-en-1-one | nat-methyl-15S,16R-11α,15-dihydroxy-9-oxo-15,16-trimethylene-13-trans-prostenoate |
| 151 | 36 | 2-(6-carbomethoxyhexyl)-4(S)-trimethylsilyloxy-cyclopent-2-en-1-one | nat-methyl-15S,16S-11α,15-dihydroxy-9-oxo-15,16-trimethylene-13-trans-prostenoate |
| 152 | 31 | 2-(6-carbomethoxyhexyl)-4(S)-trimethylsilyloxy-cyclopent-2-en-1-one | nat-methyl-11α,15-dihydroxy-9-oxo-15,16-tetramethylene-17,18,19,20-tetranor-13-trans-prostenoate |
| 153 | 30 | 2-(6-carbomethoxyhexyl)-4(S)-trimethylsilyloxy-cyclopent-2-en-1-one | nat-methyl-11α,16-dihydroxy-9-oxo-16,17-tetramethylene-18,19,20-trinor-13-trans-prostenoate |
| 154 | 39 | 2-(6-carbomethoxyhexyl)-4(S)-trimethylsilyloxy-cyclopent-2-en-1-one | nat-methyl-15R,16S-11α,15-dihydroxy-9-oxo-15,16-trimethylene-16-(3-trifluoromethylphenoxy)-17,18,19,20-tetranor-13-trans-prostenoate |
| 155 | 40 | 2-(6-carbomethoxyhexyl)-4(S)-trimethylsilyloxy-cyclopent-2-en-1-one | nat-methyl-15R,16R-11α,15-dihydroxy-9-oxo-15,16-trimethylene-16-(3-trifluoromethylphenoxy)-17,18,19,20-tetranor-13-trans-prostenoate |
| 156 | 29a | 2-(6-carbomethoxyhexyl)-4(R)-trimethylsilyloxy-cyclopent-2-en-1-one | ent-methyl-15R,16S-11α,15-dihydroxy-9-oxo-15,16-trimethylene-13-trans-prostenoate |
| 157 | 36 | 2-(6-carbomethoxyhexyl)-4(R)-trimethylsilyloxy-cyclopent-2-en-1-one | ent-methyl-15R,16R-11α,15-dihydroxy-9-oxo-15,16-trimethylene-13-trans-prostenoate |
| 158 | 31 | 2-(6-carbomethoxyhexyl)-4(R)-trimethylsilyloxy-cyclopent-2-en-1-one | ent-methyl-11α,15-dihydroxy-9-oxo-15,16-tetramethylene-17,18,19,20-tetranor-13-trans-prostenoate |
| 159 | 30 | 2-(6-carbomethoxyhexyl)-4(R)-trimethylsilyloxy-cyclopent-2-en-1-one | ent-methyl-11α,16-dihydroxy-9-oxo-16,17-tetramethylene-18,19,20-trinor-13-trans-prostenoate |
| 160 | 39 | 2-(6-carbomethoxyhexyl)-4(R)-trimethylsilyloxy-cyclopent-2-en-1-one | ent-methyl-15S,16R-11α,15-dihydroxy-9-oxo-15,16-trimethylene-16-(3-trifluoromethylphenoxy)-17,18,19,20-tetranor-13-trans-prostenoate |
| 161 | 40 | 2-(6-carbomethoxyhexyl)-4(R)-trimethylsilyloxy-cyclopent-2-en-1-one | ent-methyl-15S,16S-11α,15-dihydroxy-9-oxo-15,16-trimethylene-16-(3-trifluoromethylphenoxy)-17,18,19,20-tetranor-13-trans-prostenoate |
| 162 | 29a | 2-(6-carbomethoxyhex-2-cis-enyl)-4(S)-trimethyl-silyloxycyclopent-2-en-1-one | nat-methyl-15S,16R-11α,15-dihydroxy-9-oxo-15,16-trimethylene-13-trans-5-cis-prostenoate |
| 163 | 36 | 2-(6-carbomethoxyhex-2-cis-enyl)-4(S)-trimethyl-silyloxycyclopent-2-en-1-one | nat-methyl-15S,16S-11α,15-dihydroxy-9-oxo-15,16-trimethylene-13-trans-5-cis-prostadienoate |
| 164 | 31 | 2-(6-carbomethoxyhex-2-cis-enyl)-4(S)-trimethyl-silyloxycyclopent-2-en-1-one | nat-methyl-11α,15-dihydroxy-9-oxo-15,16-tetramethylene-17,18,19,20-tetranor-13-trans-5-cis-prostadienoate |
| 165 | 30 | 2-(6-carbomethoxyhex-2-cis-enyl)-4-(S)-trimethyl-silyloxycyclopent-2-en-1- | nat-methyl-11α,16-dihydroxy-9-oxo-16,17-tetramethylene-18,19,20-trinor-13-trans-5-cis-prostadienoate |

TABLE IV-continued

| Example | Vinyl Iodide or Vinyl Tin of Example | Cyclopent-2-en-1-one | Product optically active 9-oxo-prostaglandin and its optically active diastereoisomer |
|---|---|---|---|
| 166 | 39 | 2-(6-carbomethoxyhex-3-cis-enyl)-4(S)-trimethylsilyloxycyclopent-2-en-1-one | nat-methyl-15R,16S-11α,15-dihydroxy-9-oxo-15,16-trimethylene-16-(3-trifluoromethylphenoxy)-17,18,19,20-tetranor-13-trans-5-cis-prostadienoate |
| 167 | 40 | 2-(6-carbomethoxyhex-2-cis-enyl)-4(S)-trimethylsilyloxycyclopent-2-en-1-one | nat-methyl-15R,16R-11α,15-dihydroxy-9-oxo-15,16-trimethylene-16-(3-trifluoromethylphenoxy)-17,18,19,20-tetranor-13-trans-5-cis-prostadienoate |
| 168 | 31 | 2-(6-carbotrimethylsilyloxy-5-thiahexyl)-4-trimethylsilyloxycyclopent-2-en-1-one | nat-(and ent)-11α,15-dihydroxy-3-thia-9-oxo-15,16-trimethylene-17,18,19,20-tetranor-13-trans-prostenoic acid |
| 169 | 29a | 2-(6-carbotrimethylsilyloxy-5-thiahexyl)-4-trimethylsilyloxycyclopent-2-en-1-one | nat-15S,16R(and ent-15R,16S)-11α,15-dihydroxy-3-thia-9-oxo-15,16-trimethylene-13-trans-prostenoic acid |
| 170 | 36 | 2-(6-carbotrimethylsilyloxy-5-thiahexyl)-4-trimethylsilyloxycyclopent-2-en-1-one | nat-15S,16S-(and ent-15R,16R)-11α,15-dihydroxy-3-thia-9-oxo-15,16-trimethylene-13-trans-prostenoic acid |
| 171 | 30 | 2-(6-carbotrimethylsilyloxy-5-thiahexyl)-4-trimethylsilyloxycyclopent-2-en-1-one | nat-(and ent)-11α,16-dihydroxy-3-thia-9-oxo-16,17-tetramethylene-18,19,20-trinor-13-trans-prostenoic acid |
| 172 | 39 | 2-(6-carbotrimethylsilyloxy-5-thiahexyl)-4-trimethylsilyloxycyclopent-2-en-1-one | nat-15R,16S-(and ent-15S,16R)-11α,15-dihydroxy-3-thia-9-oxo-15,16-trimethylene-16-(3-trifluoromethylphenoxy)-17,18,19,20-tetranor-13-trans-prostenoic acid |
| 173 | 40 | 2-(6-carbotrimethylsilyloxy-5-thiahexyl)-4-trimethylsilyloxycyclopent-2-en-1-one | nat-15R,16R-(and ent-15S,16S)-11α,15-dihydroxy-3-thia-9-oxo-15,16-trimethylene-16-(3-trifluoromethylphenoxy)-17,18,19,20-tetranor-13-trans-prostenoic acid |
| 174 | 31 | 2-(5-carbotrimethylsilyloxy-4-thiapentyl)-4-trimethylsilyloxycyclopent-2-en-1-one | nat-(and ent)-11α,15-dihydroxy-3-thia-9-oxo-15,16-tetramethylene-4,17,18,19,20-pentanor-13-trans-prostenoic acid |
| 175 | 29a | 2-(5-carbotrimethylsilyloxy-4-thiapentyl)-4-trimethylsilyloxycyclopent-2-en-1-one | nat-15S,16R-(and ent-15R,16S)-11α,15-dihydroxy-3-thia-9-oxo-15,16-trimethylene-4-nor-13-trans-prostenoic acid |
| 176 | 36 | 2-(5-carbotrimethylsilyloxy-4-thiapentyl)-4-trimethylsilyloxycyclopent-2-en-1-one | nat-15S,16S-(and ent-15R,16R)-11α,15-dihydroxy-3-thia-9-oxo-15,16-trimethylene-4-nor-13-trans-prostenoic acid |
| 177 | 30 | 2-(5-carbotrimethylsilyloxy-4-thiapentyl)-4-trimethylsilyloxycyclopent-2-en-1-one | nat-(and ent)-11α,16-dihydroxy-3-thia-9-oxo-16,17-tetramethylene-4,18,19,20-tetranor-13-trans-prostenoic acid |
| 178 | 39 | 2-(5-carbotrimethylsilyloxy-4-thiapentyl)-4-trimethylsilyloxycyclopent-2-en-1-one | nat-15R,16S-(and ent-15S,16R)-11α,15-dihydroxy-3-thia-9-oxo-15,16-trimethylene-16-(3-trifluoromethylphenoxy)-4,17,18,19,20-pentanor-13-trans-prostenoic acid |
| 179 | 40 | 2-(5-carbotrimethylsilyloxy-4-thiapentyl)-4-trimethylsilyloxycyclopent-2-en-1-one | nat-15R,16R-(and ent-15S,16S)-11α,15-dihydroxy-3-thia-9-oxo-15,16-trimethylene-16 (3-trifluoromethylphenoxy)-4,17,18,19,20-pentanor-13-trans-prostenoic acid |

EXAMPLE 180

Preparation of methyl nat(and ent-)-11α,15-dihydroxy-9-oxo-15,16-tetramethylene-17,18,19,20-tetranor-5-cis-13-trans-prostadienoate To an ethereal solution of 0.10 g of nat(and ent)-11α,15-dihydroxy-9-oxo-15,16-tetramethylene-17,18,19,20-tetranor-5-cis-13-trans-prostadienoic acid is added an excess of ethereal diazomethane. After 5 minutes the excess diazomethane and the solvent is blown off with a stream of nitrogen to give the title methyl ester.

EXAMPLES 181-187

In the manner of Example 180 described above, the prostaglandins listed in Table XII are esterified with the indicated diazoalkanes.

TABLE V

| Example | Prostaglandin of Example | Diazoalkane | Product esterified prostaglandin |
|---|---|---|---|
| 181 | 65 | diazomethane | methyl nat-(and ent)-11α,16-dihydroxy-9-oxo-16,17-tetramethylene-18,19,20-trinor-5-cis-13-trans-prostadienoate |
| 182 | 68 | diazoethane | ethyl nat-15S,16R-(and ent-15R,16S)-11α,15-dihydroxy-9-oxo-15,16-trimethylene-13-trans-prostenoate |
| 183 | 69 | 1-diazopropane | n-propyl nat-15S,16S-(and ent-15R,16S)-11α,15-dihydroxy-9-oxo-15,16-trimethylene-13-trans-prostenoate |
| 184 | 64 | diazomethane | methyl-nat-(and ent)-11α,15-dihydroxy-9-oxo-15,16-tetramethylene-17,18,19,20-tetranor-13-trans-prostenoate |
| 185 | 66 | 1-diazohexane | n-hexyl-nat-15S,16R-(and ent-15R,16S)-11α,-15-dihydroxy-9-oxo-15,16-trimethylene-5-cis-13-trans-prostadienoate |
| 186 | 63 | diazomethane | methyl-nat-(and ent)-11,15-dihydroxy-9-oxo-15,16-tetramethylene-17,18,19,20-tetranor-5-cis-13-trans-prostadienoate |
| 187 | 63 | diazoethane | ethyl-nat-(and ent)-11,15-dihydroxy-9-oxo-15,16-tetramethylene-17,18,19,20-tetranor-5-cis-13-trans-prostdienoate. |

EXAMPLE 188

Preparation of nat(and ent)-11α,15-dihydroxy-9-oxo-15,16-tetramethylene-17,18,19,20-tetranor prostanoic acid A solution of nat(and ent)-11α,15-dihydroxy-9-oxo-15,16-tetramethylene-17,18,19,20-tetranor-13-trans-prost noic acid (800 mg) in 50 ml of ethyl acetate is hydrogenated in a Parr apparatus using 500 mg of 5% rhodium-on-carbon. The catalyst is removed by filtration and the filtrate is taken to dryness to furnish the titled product.

EXAMPLES 189-192

Hydrogenation of the prostenoic acids listed in Table VI below in ethyl acetate using a rhodium-on-carbon catalyst in accordance with the method described in Example 198 gives the prostanoic acids of the table.

TABLE VI

| Example | 13-trans-prostenoic acid of Example | Prostanoic Acid |
|---|---|---|
| 189 | 68 | nat-15S,16R-(and ent-15R,16S)-11α,15-dihydroxy-9-oxo-15,16-trimethylene prostanoic acid |
| 190 | 69 | nat-15S,16S-(and ent-15R,16R)-11α,15-dihydroxy-9-oxo-15,16-trimethylene prostanoic acid |
| 191 | 79 | nat-(and ent)-11α,16-dihydroxy-9-oxo-16,17-tetramethylene-18,19,20-trinor prostanoic acid |
| 192 | 196 | nat-15S,16S-(and ent-15R,16R)-15-hydroxy-9-oxo-15,16-trimethylene prostanoic acid |

EXAMPLE 193

Preparation of Ethyl nat-15S,16S(and ent-15R,16R)-15-hydroxy-9-oxo-15,16-trimethylene-13-trans-prostenoate and Ethyl nat-15R,16R(and ent-15S,16S)-15-hydroxy-9-oxo-15,16-trimethylene-13-trans-prostenoate To a solution of 2.42 g of thiophenol in 60 ml of ether is added under nitrogen at 0° C., 9.56 ml of 2.3 M n-butyl lithium. The mixture is stirred for one hour and then a solution of 8.64 g of copper iodide tri-n-butyl phosphine complex in 120 ml of ether is added. To 7.69 g of 1R,2R(and 1S,2S)-1-(trans-2-iodovinyl)-1-trimethylsilyloxy-2-butylcyclopentane in 15 ml of toluene at −45° C. is added 53.75 ml of 0.8 M t-butyl lithium. After stirring under nitrogen for 90 minutes the solution is removed from the cooling bath and stirred for 10 minutes. The solution is recooled to −78° C. and 10 ml of ether is added. The copper solution is cooled to −78° C. and then added via a double needle to the vinyl solution. After 20 minutes, 5.0 g of 2-(6-carboethoxyhexyl)cyclopent-2-en-1-one in 20 ml of ether is added. The mixture is then stirred at −50° C. to −40° C. for 90 minutes and then at 0° C. for 30 minutes. A saturated solution of ammonium chloride is added to the mixture which is then stirred for 10 minutes. The organic layer is separated and the aqueous layer is extracted with ether. The combined ether solutions are washed with dilute HCl followed by saturated aqueous sodium bicarbonate. The solution is dried with magnesium sulfate and the solvent is furan:acetic acid:water (2:4:1). Three drops of concentrated HCl are added and the mixture is stirred at 45° C. for 2 hours and then stored overnight at 0° C. The mixture is poured into water and extracted with ether. The ether solution is washed with water and saturated aqueous sodium bicarbonate and then dried with magnesium sulfate. The ether is removed giving a yellow oil. This oil is chromatographed on a dry column of silica gel eluting with ether-hexane 1:1 giving 1.22 g of ethyl nat-15S,16S(and ent-15R,16R)-15-hydroxy-9-oxo-15,16-trimethylene-13-trans-prostenoate (lower $R_f$) and 0.51 g of ethyl nat-15R,16R( and ent-15S,16S)-15-hydroxy-9-oxo-15,16-trimethylene-13-trans-prostenoate (higher $R_f$) and 0.83 g of a mixture of the two isomers.

EXAMPLE 194

Preparation of Ethyl nat-15S,16R(and ent-15R,16S)-15-hydroxy-9-oxo-15,16-trimethylene-13-trans-prostenoate and Ethyl nat-15R,16S(and ent-15S,16R)-15-hydroxy-9-oxo-15,16-trimethylene-13-trans-prostenoate To a solution of 2.42 g of thiophenol in 60 ml of ether under nitrogen at 0° C. is added 9.56 ml of 2.3 M n-butyl lithium. The mixture is stirred for one hour and then a solution of 8.64 g of copper tri-n-butyl phosphine complex in 120 ml of ether is added. This solution is stored in a freezer. To 7.69 g of 1R,2S(and 1S,2R)-1-(trans-2-iodovinyl)-1-trimethylsilyloxy-2-butylcyclopentane in 15 ml of toluene at −45° C. is added 53.75 ml of t-butyl lithium. After stirring for 90 minutes the solution is removed from the cooling bath, stirred for 15 minutes and then recooled to −78° C. The copper solution is cooled to −78° C. and added to the vinyl lithium solution. After 35 minutes 5.0 g of 2-(6-carboethoxyhexyl)-cyclopent-2-en-1-one in 35 ml of ether is added followed by 35 ml of ether. The mixture is stirred at −45° C. for 90 minutes and then at 0° C. for 30 minutes. Saturated ammonium chloride solution is added. The ether layer is separated and washed with dilute HCl and concentrated sodium bicarbonate. The solution is dried over magnesium sulfate. The solvent is removed giving a yellow liquid. This liquid is dissolved in 150 ml of a 4:2:1 mixture of acetic acid:tetrahydrofuran:water. One drop of concentrated HCl is added and the mixture is stirred for 30 minutes at room temperature and 3.5 hours at 40° C. The solvent is removed giving a mixture of the two racemates titled above. The diastereoisomers can be separated by chromatographic means.

EXAMPLE 195

Preparation of Ethyl nat(and ent)-15-hydroxy-9-oxo-15,16-tetramethylene-17,18,19,20-tetranor-13-trans-prostenoate To a solution of 0.735 g of 1-(trans-2-iodovinyl)-1-trimethylsilyloxycyclohexane in one ml of toluene cooled to −40° C. under argon is added 1.14 ml of 2.04 M n-butyllithium in hexane. This mixture is stirred for 2 hours. A 2 ml portion of ether is added and the mixture is allowed to warm to room temperature producing a clear colorless solution. This solution is recooled to −40° C. and is then treated with 0.90 ml of 2.44 M trimethylaluminum in heptane. The mixture is allowed to warm to room temperature and is then treated with 2 ml of ether. Recooling to −40° C. produces a precipitate. The reaction mixture is then treated with 0.620 g of 2-(6-carbethoxyhexyl)cyclopent-2-en-1-one. The cooling bath is removed, the mixture is allowed to warm to room temperature and stirred overnight. The mixture is poured onto ice and dilute HCl, extracted with ether and the organic phase is washed with water and saturated brine, dried with magnesium sulfate and evaporated giving 1.042 g of a nearly colorless oil. This entire crude oil is dry column chromatographed on 100 g of silica gel packed in a 20"×1¼" column and equilibrated with 10% by weight of 9:1 benzene:ethyl acetate. The column is eluted with 9:1 benzene:ethyl acetate and cut into one inch segments. The product is found along the column at Rf 0.60–0.75 giving 0.460 g of an oil. This oil is dissolved in 10 ml of a 4:2:1 mixture of acetic acid:tetrahydrofuran:water and swirled at room temperature for 3 minutes. The solvent is evaporated under vacuum on a water bath at 37° C. A 10 ml portion of xylene is added and then evaporated giving 0.406 g of ethyl nat-(and ent)-15-hydroxy-9-oxo-15,16-tetramethylene-17,18,19,20-tetranor-13-trans-prostenoate.

EXAMPLE 196

Preparation of nat-15S,16S(and ent-15R,16R)-15-Hydroxy-9-oxo-15,16-trimethylene-13-trans-prostenoic Acid A mixture of 0.9 g of ethyl nat-15S,16S(and ent-15R,16R)-15-hydroxy-9-oxo-15,16-trimethylene-13-trans-prostenoate and 0.32 g of sodium hydroxide in one ml of water and 12 ml of methanol is stirred at room temperature for 3.5 hours. The solution is poured into water and washed with ether. The solution is acidified with HCl and extracted with ether. The ether is removed giving 0.83 g of nat-15S,16S(ent-15R,16R)-15-hydroxy-9-oxo-15,16-trimethylene-13-trans-prostenoic acid.

EXAMPLE 197

Preparation of nat-15R,16R(and ent-15S,16S)-15-Hydroxy-9-oxo-15,16-trimethylene-13-trans-prostenoic Acid A mixture of 0.38 g of ethyl nat-15R,16R(and ent-15S,16S)-15-hydroxy-9-oxo-15,16-trimethylene-13-trans-prostenoate and 0.14 g of sodium hydroxide in 6 ml of methanol is stirred for 3.5 hours. The solution is poured into water and washed with ether. The solution is acidified with hydrochloric acid and extracted with ether. The ether is removed giving 0.35 g of the product as a yellow oil.

EXAMPLE 198

Preparation of nat-15S,16R(and ent-15R,16S) and nat-15R,16S(and ent-15S,16R)-15-Hydroxy-9-oxo-15,16-trimethylene-13-trans-prostenoic Acid To a 3.5 g portion of a mixture of ethyl esters of the title compounds is added 1.26 g of sodium hydroxide in 2.5 ml of water and 50 ml of methanol. The mixture is stirred at room temperature under nitrogen for 4 hours and then poured into water. The solution is washed with ether, acidified with hydrochloric acid and extracted with ether. The ether is dried with magnesium sulfate and activated charcoal and filtered through a pad of silica gel. The solvent is removed giving a yellow oil. The product is purified by dry column chromatography, eluting with ethyl acetate:hexane (2:3) giving 2.41 g of the desired mixed isomers as nearly colorless oil.

EXAMPLE 199

Preparation of nat(and ent)-15-Hydroxy-9-oxo-15,16-tetramethylene-17,18,19,20-tetranor-13-trans-prostenoic Acid A mixture of 5.54 g of the ethyl ester of the title compound and 2.58 g of potassium hydroxide in 100 ml of 1:1 aqueous methanol is stirred under argon at ambient temperature for 22 hours. The solvent is partially evaporated in vacuo and the residue is diluted with water and acidified with HCl. The aqueous phase is extracted with ether and the organic phase is washed with water and saturated brine, dried with magnesium sulfate and evaporated to dryness. The resulting oil is reduced in vacuo overnight to give the desired product as 4.826 g of a nearly colorless oil.

EXAMPLES 200-290

In the manner described hereinabove for Examples 193, 194, and 195, the 0-oxo-prostaglandins shown in Table VII are prepared from the indicated vinyl iodide or vinyl tin compounds and the indicated cyclopent-2-en-1-one. The cyclopent-2-en-1-ones listed in Table VII are used as their ethyl esters. The products of the conjugate addition are ethyl esters which are hydrolyzed as described hereinabove for Examples 196, 197 and 198. Only the acids are listed in Table VII and it is to be understood that both the acid and esters are claimed in this invention. In those cases where two diastereoisomers are formed in the conjugate-addition, only one of the diastereoisomers is listed in Table VII. It should be understood that the other diastereoisomer is also formed which in its nat and ent forms has an opposite (mirror image) configuration at the assymmetric carbon atoms on the $\beta$-chain (the chain containing $C_{13} \ldots C_{14}$ etc.) to that of the respective nat and ent forms of the listed diastereoisomer; both of these diastereoisomers are claimed in this invention as well as their component enantiomers.

TABLE VII

| Example | Vinyl Iodide or Vinyl Tin of Example | Cyclopent-2-en-1-one | Product 9-oxo-prostaglandin and its diastereoisomer and ethyl ester where applicable (see hereinabove) |
|---|---|---|---|
| 200 | 32 | 2-(6-carboxyhexyl)cyclopent-2-en-1-one | nat-(and ent)-15-hydroxy-9-oxo-15,16-trimethylene-17,18,19,20-tetranor-13-trans-prostenoic acid |
| 201 | 33 | 2-(6-carboxyhexyl)cyclopent-2-en-1-one | nat-(and ent)-15-hydroxy-9-oxo-15,16-pentamethylene-17,18,19,20-tetranor-13-trans-prostenoic acid |
| 202 | 34 | 2-(6-carboxyhexyl)cyclopent-2-en-1-one | nat-15S,17R-(and ent-15R,17S)-15-hydroxy-9-oxo-15,17-dimethylene-13-trans-prostenoic acid |
| 203 | 35 | 2-(6-carboxyhexyl)cyclopent-2-en-1-one | nat-15S,17S-(and ent-15R,17R)-15-hydroxy-9-oxo-15,17-dimethylene-13-trans-prostenoic acid |
| 204 | 37 | 2-(6-carboxyhexyl)cyclopent-2-en-1-one | nat-15S,16R-(and ent-15R,16S)-15-hydroxy-9-oxo-15,16-tetramethylene-13-trans-prostenoic acid |
| 205 | 38 | 2-(6-carboxyhexyl)cyclopent-2-en-1-one | nat-15S,16S-(and ent-15R,16R)-15-hydroxy-9-oxo-15,16-tetramethylene-13-trans-prostenoic acid |
| 206 | 39 | 2-(6-carboxyhexyl)cyclopent-2-en-1-one | nat-15R,16S-(and ent-15S,16R)-15-hydroxy-9-oxo-15,16-trimethylene-16-(3-trifluoromethylphenoxy)-17,18,19,20-tetranor-13-trans-prostenoic acid |
| 207 | 40 | 2-(6-carboxyhexyl)cyclopent-2-en-1-one | nat-15R,16R-(and ent-15S,16S)-15-hydroxy-9-oxo-15,16-trimethylene-16-(3-trifluoromethylphenoxy)-17,18,19,20-tetranor-13-trans-prostenoic acid |
| 208 | 30 | 2-(6-carboxyhexyl)cyclopent-2-en-1-one | nat-(and ent)-16-hydroxy-9-oxo-16,17-tetramethylene-18,19,20-trinor-13-trans-prostenoic acid |
| 209 | 41 | 2-(6-carboxyhexyl)cyclopent-2-en-1-one | nat-15R,16S-(and ent-15S,16R)-15-hydroxy-9-oxo-15,16-trimethylene-16-(4-fluorophenoxy)-17,18,19,20-tetranor-13-trans-prostenoic acid |
| 210 | 42 | 2-(6-carboxyhexyl)cyclopent-2-en-1-one | nat-15R,16R-(and ent-15S,16S)-15-hydroxy-9-oxo-15,16-trimethylene-16-(4-fluorophenoxy)-17,18,19,20-tetranor-13-trans-prostenoic acid |
| 211 | 43 | 2-(6-carboxyhexyl)cyclopent-2-en-1-one | nat-15R,16S-(and ent-15S,16R)-15-hydroxy-9-oxo-15,16-trimethylene-16-(3-chlorophenoxy)-17,18,19,20-tetranor-13-trans-prostenoic acid |
| 212 | 44 | 2-(6-carboxyhexyl)cyclopent-2-en-1-one | nat-15R,16R-(and ent-15S,16S)-15-hydroxy-9-oxo-15,16-trimethylene-16-(3-chlorophenoxy)-17,18,19,20-tetranor-13-trans-prostenoic acid |
| 213 | 45 | 2-(6-carboxyhexyl)cyclopent-2-en-1-one | nat-15S,17R-(and ent-15R,17S)-15-hydroxy-9-oxo-15,17-trimethylene-19,20-dinor-13-trans-prostenoic acid |
| 214 | 46 | 2-(6-carboxyhexyl)cyclopent-2-en-1-one | nat-15S,17S-(and ent-15R,17R)-15-hydroxy-9-oxo-15,17-trimethylene-19,20-dinor-13-trans-prostenoic acid |
| 215 | 47 | 2-(6-carboxyhexyl)cyclopent-2-en-1-one | nat-16R,17S-(and ent-16S,17R)-16-hydroxy-9-oxo-16,17-trimethylene-20-methyl-13-trans-prostenoic acid |
| 216 | 48 | 2-(6-carboxyhexyl)cyclopent-2-en-1-one | nat-16R,17R-(and ent-16S,17S)-16-hydroxy-9-oxo-16,17-trimethylene-20-methyl-13-trans-prostenoic acid |

TABLE VII-continued

| Example | Vinyl Iodide or Vinyl Tin of Example | Cyclopent-2-en-1-one | Product 9-oxo-prostaglandin and its diastereoisomer and ethyl ester where applicable (see hereinabove) |
|---|---|---|---|
| 217 | 49 | 2-(6-carboxyhexyl)cyclopent-2-en-1-one | nat-16R,17S-(and ent-16S,17R)-16-hydroxy-9-oxo-16,17-trimethylene-17-(3-trifluoromethylphenoxy)-18,19,20-trinor-13-trans-prostenoic acid |
| 218 | 50 | 2-(6-carboxyhexyl)cyclopent-2-en-1-one | nat-16R,17R-(and ent-16S,17S)-16-hydroxy-9-oxo-16,17-trimethylene-17-(3-trifluoromethylphenoxy)-18,19,20-trinor-13-trans-prostenoic acid |
| 219 | 29a | 2-(5-carboxypentyl)cyclopent-2-en-1-one | nat-15S,16R-(and ent-15R,16S)-15-hydroxy-9-oxo-15,16-trimethylene-2-nor-13-trans-prostenoic acid |
| 220 | 36 | 2-(5-carboxypentyl)cyclopent-2-en-1-one | nat-15S,16S-(and ent-15R,16R)-15-hydroxy-9-oxo-15,16-trimethylene-2-nor-13-trans-prostenoic acid |
| 221 | 31 | 2-(5-carboxypentyl)cyclopent-2-en-1-one | nat-(and ent)-15-hydroxy-9-oxo-15,16-tetramethylene-2,17,18,19,20-pentanor-13-trans-prostenoic acid |
| 222 | 32 | 2-(5-carboxypentyl)cyclopent-2-en-1-one | nat-(and ent)-15-hydroxy-9-oxo-15,16-trimethylene-2,17,18,19,20-pentanor-13-trans-prostenoic acid |
| 223 | 33 | 2-(5-carboxypentyl)cyclopent-2-en-1-one | nat-(and ent)-15-hydroxy-9-oxo-15,16-pentamethylene-2,17,18,19,20-pentanor-13-trans-prostenoic acid |
| 224 | 34 | 2-(5-carboxypentyl)cyclopent-2-en-1-one | nat-15S,17R-(and ent-15R,17S)-15-hydroxy-9-oxo-15,17-dimethylene-2-nor-13-trans-prostenoic acid |
| 225 | 35 | 2-(5-carboxypentyl)cyclopent-2-en-1-one | nat-15S,17S-(and ent-15R,17R)-15-hydroxy-9-oxo-15,17-dimethylene-2-nor-13-trans-prostenoic acid |
| 226 | 39 | 2-(5-carboxypentyl)cyclopent-2-en-1-one | nat-15R,16S-(and ent-15S,16R)-15-hydroxy-9-oxo-15,16-trimethylene-16-(3-trifluoromethylphenoxy)-2,17,18,19,20-pentanor-13-trans-prostenoic acid |
| 227 | 40 | 2-(5-carboxypentyl)cyclopent-2-en-1-one | nat-15R,16R-(and ent-15S,16S)-15-hydroxy-9-oxo-15,16-trimethylene-16-(3-trifluoromethylphenoxy)-2,17,18,19,20-pentanor-13-trans-prostenoic acid |
| 228 | 29a | 2-(7-carboxyheptyl)cyclopent-2-en-1-one | nat-15S,16R-(and ent-15R,16S)-15-hydroxy-9-oxo-15,16-trimethylene-1-homo-13-trans-prostenoic acid |
| 229 | 36 | 2-(7-carboxyheptyl)cyclopent-2-en-1-one | nat-15S,16S-(and ent-15R,16R)-15-hydroxy-9-oxo-15,16-trimethylene-1-homo-13-trans-prostenoic acid |
| 230 | 31 | 2-(7-carboxyheptyl)cyclopent-2-en-1-one | nat-(and ent)-15-hydroxy-9-oxo-15,16-tetramethylene-1-homo-17,18,19,20-tetranor-13-trans-prostenoic acid |
| 231 | 37 | 2-(7-carboxyheptyl)cyclopent-2-en-1-one | nat-15S,16R-(and ent-15R,16S)-15-hydroxy-9-oxo-15,16-tetramethylene-1-homo-13-trans-prostenoic acid |
| 232 | 38 | 2-(7-carboxyheptyl)cyclopent-2-en-1-one | nat-15S,16S-(and ent-15R,16R)-15-hydroxy-9-oxo-15,16-tetramethylene-1-homo-13-trans-prostenoic acid |
| 233 | 41 | 2-(7-carboxyheptyl)cyclopent-2-en-1-one | nat-15R,16S-(and ent-15S,16R)-15-hydroxy-9-oxo-15,16-trimethylene-16-(4-fluorophenoxy)-1-homo-17,18,19,20-tetranor-13-trans-prostenoic acid |
| 234 | 42 | 2-(7-carboxyheptyl)cyclopent-2-en-1-one | nat-15R,16R-(and ent-15S,16S)-15-hydroxy-9-oxo-15,16-trimethylene-16-(4-fluorophenoxy)-1-homo-17,18,19,20-tetranor-13-trans-prostenoic acid |
| 235 | 45 | 2-(8-carboxyoctyl)cyclopent-2-en-1-one | nat-15S,17R-(and ent-15R,17S)-15-hydroxy-oxo-15,17-trimethylene-19,20-dinor-1a,1b-dihomo-13-trans-prostenoic acid |
| 236 | 46 | 2-(8-carboxyoctyl)cyclopent-2-en-1-one | nat-15S,17S-(and ent-15R,17R)-15-hydroxy-oxo-15,17-trimethylene-19,20-dinor-1a,1b-dihomo-13-trans-prostenoic acid |
| 237 | 47 | 2-(8-carboxyoctyl)cyclopent-2-en-1-one | nat-16R,17S-(and ent-16S,17R)-16-hydroxy-9-oxo-16,17-trimethylene-20-methyl-1a,1b-dihomo-13-trans-prostenoic acid |

TABLE VII-continued

| Example | Vinyl Iodide or Vinyl Tin of Example | Cyclopent-2-en-1-one | Product 9-oxo-prostaglandin and its diastereoisomer and ethyl ester where applicable (see hereinabove) |
|---|---|---|---|
| 238 | 48 | 2-(8-carboxyoctyl)cyclopent-2-en-1-one | nat-16R,17R-(and ent-16S,17S)-16-hydroxy-9-oxo-16,17-trimethylene-20-methyl-1a,1b-dihomo-13-trans-prostenoic acid |
| 239 | 49 | 2-(8-carboxyoctyl)cyclopent-2-en-1-one | nat-16R,17S-(and ent-16S,17R)-16-hydroxy-9-oxo-16,17-trimethylene-17-(3-trifluoromethylphenoxy)-18,19,20-trinor-1a,1b-dihomo-13-trans-prostenoic acid |
| 240 | 50 | 2-(8-carboxyoctyl)cyclopent-2-en-1-one | nat-16R,17R-(and ent-16S,17S)-16-hydroxy-9-oxo-16,17-trimethylene-17-(3-trifluoromethylphenoxy)-18,19,20-trinor-1a,1b-dihomo-13-trans-prostenoic acid |
| 241 | 29a | 2-(6-carboxyhex-2-cis-enyl)cyclopent-2-en-1-one | nat-15S,16R-(and ent-15R,16S)-15-hydroxy-9-oxo-15,16-trimethylene-13-trans-5-cis-prostadienoic acid |
| 242 | 36 | 2-(6-carboxyhex-2-cis-enyl)cyclopent-2-en-1-one | nat-15S,16S-(and ent-15R,16R)-15-hydroxy-9-oxo-15,16-trimethylene-13-trans-5-cis-prostadienoic acid |
| 243 | 31 | 2-(6-carboxyhex-2-cis-enyl)cyclopent-2-en-1-one | nat-(and ent)-15-hydroxy-9-oxo-15,16-tetramethylene-17,18,19,20-tetranor-13-trans-5-cis-prostadienoic acid |
| 244 | 32 | 2-(6-carboxyhex-2-cis-enyl)cyclopent-2-en-1-one | nat-(and ent)-15-hydroxy-9-oxo-15,16-trimethylene-17,18,19,20-tetranor-13-trans-5-cis-prostadienoic acid |
| 245 | 33 | 2-(6-carboxyhex-2-cis-enyl)cyclopent-2-en-1-one | nat-(and ent)-15-hydroxy-9-oxo-15,16-pentamethylene-17,18,19,20-tetranor-13-trans-5-cis-prostadienoic acid |
| 246 | 34 | 2-(6-carboxyhex-2-cis-enyl)cyclopent-2-en-1-one | nat-15S,17R-(and ent-15R,17S)-15-hydroxy-9-oxo-15,17-dimethylene-13-trans-5-cis-prostadienoic acid |
| 247 | 35 | 2-(6-carboxyhex-2-cis-enyl)cyclopent-2-en-1-one | nat-15S,17S-(and ent-15R,17R)-15-hydroxy-9-oxo-15,17-dimethylene-13-trans-5-cis-prostadienoic acid |
| 248 | 37 | 2-(6-carboxyhex-2-cis-enyl)cyclopent-2-en-1-one | nat-15S,16R-(and ent-15R,16S)-15-hydroxy-9-oxo-15,16-tetramethylene-13-trans-5-cis-prostadienoic acid |
| 249 | 38 | 2-(6-carboxyhex-2-cis-enyl)cyclopent-2-en-1-one | nat-15S,16S-(and ent-15R,16R)-15-hydroxy-9-oxo-15,16-tetramethylene-13-trans-5-cis-prostadienoic acid |
| 250 | 39 | 2-(6-carboxyhex-2-cis-enyl)cyclopent-2-en-1-one | nat-15R,16S-(and ent-15S,16R)-15-hydroxy-9-oxo-15,16-trimethylene-16-(3-trifluoromethylphenoxy)-17,18,19,20-tetranor-13-trans-5-cis-prostadienoic acid |
| 251 | 40 | 2-(6-carboxyhex-2-cis-enyl)cyclopent-2-en-1-one | nat-15R,16R-(and ent-15S,16S)-15-hydroxy-9-oxo-15,16-trimethylene-16-(3-trifluoromethylphenoxy)-17,18,19,20-tetranor-13-trans-5-cis-prostadienoic acid |
| 252 | 30 | 2-(6-carboxyhex-2-cis-enyl)cyclopent-2-en-1-one | nat-(and ent)-16-hydroxy-9-oxo-16,17-tetramethylene-18,19,20-trinor-13-trans-5-cis-prostadienoic acid |
| 253 | 41 | 2-(6-carboxyhex-2-cis-enyl)cyclopent-2-en-1-one | nat-15R,16S-(and ent-15S,16R)-15-hydroxy-9-oxo-15,16-trimethylene-16-(4-fluorophenoxy)-17,18,19,20-tetranor-13-trans-5-cis-prostadienoic acid |
| 254 | 42 | 2-(6-carboxyhex-2-cis-enyl)cyclopent-2-en-1-one | nat-15R,16R-(and ent-15S,16S)-15-hydroxy-9-oxo-15,16-trimethylene-16-(4-fluorophenoxy)-17,18,19,20-tetranor-13-trans-5-cis-prostadienoic acid |
| 255 | 43 | 2-(6-carboxyhex-2-cis-enyl)cyclopent-2-en-1-one | nat-15R,16S-(and ent-15S,16R)-15-hydroxy-9-oxo-15,16-trimethylene-16-(3-chlorophenoxy)-17,18,19,20-tetranor-13-trans-5-cis-prostadienoic acid |
| 256 | 44 | 2-(6-carboxyhex-2-cis-enyl)cyclopent-2-en-1-one | nat-15R,16R-(and ent-15S,16S)-15-hydroxy-9-oxo-15,16-trimethylene-16-(3-chlorophenoxy)-17,18,19,20-tetranor-13-trans-5-cis-prostadienoic acid |
| 257 | 45 | 2-(6-carboxyhex-2-cis-enyl)cyclopent-2-en-1- | nat-15S,17R-(and ent-15R,17S)-15-hydroxy-9-oxo-15,17-trimethylene- |

TABLE VII-continued

| Example | Vinyl Iodide or Vinyl Tin of Example | Cyclopent-2-en-1-one | Product 9-oxo-prostaglandin and its diastereoisomer and ethyl ester where applicable (see hereinabove) |
|---|---|---|---|
| | | one | 19,20-dinor-13-trans-5-cis-prostadienoic acid |
| 258 | 46 | 2-(6-carboxyhex-2-cis-enyl)cyclopent-2-en-1-one | nat-15S,17S-(and ent-15R,17R)-15-hydroxy-9-oxo-15,17-trimethylene-19,20-dinor-13-trans-5-cis-prostadienoic acid |
| 259 | 47 | 2-(6-carboxyhex-2-cis-enyl)cyclopent-2-en-1-one | nat-16R,17S-(and ent-16S,17R)-16-hydroxy-9-oxo-16,17-trimethylene-20-methyl-13-trans-5-cis-prostadienoic acid |
| 260 | 48 | 2-(6-carboxyhex-2-cis-enyl)cyclopent-2-en-1-one | nat-16R,17R-(and ent-16S,17S)-16-hydroxy-9-oxo-16,17-trimethylene-20-methyl-13-trans-5-cis-prostadienoic acid |
| 261 | 49 | 2-(6-carboxyhex-2-cis-enyl)cyclopent-2-en-1-one | nat-16R,17S-(and ent-16S,17R)-16-hydroxy-9-oxo-16,17-trimethylene-17-(3-trifluoromethylphenoxy)-18,19,20-trinor-13-trans-5-cis-prostadienoic acid |
| 262 | 50 | 2-(6-carboxyhex-2-cis-enyl)cyclopent-2-en-1-one | nat-16R,17R-(and ent-16S,17S)-16-hydroxy-9-oxo-16,17-trimethylene-17-(3-trifluoromethylphenoxy)-18,19,20-trinor-13-trans-5-cis-prostadienoic acid |
| 263 | 29a | 2-(8-carboxyoct-2-cis-cyclopent-2-en-1-one | nat-15S,16R-(and ent-15R,16S)-15-hydroxy-9-oxo-15,16-trimethylene-1a,1b-dihomo-13-trans-5-cis-prostadienoic acid |
| 264 | 36 | 2-(8-carboxyoct-2-cis-enyl)cyclopent-2-en-1-one | nat-15S,16S-(and ent-15R,16R)-15-hydroxy-9-oxo-15,16-trimethylene-1a,1b-dihomo-13-trans-5-cis-prostadienoic acid |
| 265 | 31 | 2-(8-carboxyoct-2-cis-enyl)cyclopent-2-en-1-one | nat-(and ent)-15-hydroxy-9-oxo-15,16-tetramethylene-1a,1b-dihomo-17,18,19,20-tetranor-13-trans-5-cis-prostadienoic acid |
| 266 | 37 | 2-(8-carboxyoct-2-cis-enyl)cyclopent-2-en-1-one | nat-15S,16R-(and ent-15R,16S)-15-hydroxy-9-oxo-15,16-tetramethylene-1a,1b-dihomo-13-trans-5-cis-prostadienoic acid |
| 267 | 38 | 2-(8-carboxyoct-2-cis-enyl)cyclopent-2-en-1-one | nat-15S,16S-(and ent-15R,16R)-15-hydroxy-9-oxo-15,16-tetramethylene-1a,1b-dihomo-13-trans-5-cis-prostadienoic acid |
| 268 | 39 | 2-(8-carboxyoct-2-cis-enyl)cyclopent-2-en-1-one | nat-15R,16S-(and ent-15S,16R)-15-hydroxy-9-oxo-15,16-trimethylene-16-(3-trifluoromethylphenoxy)-1a,1b-dihomo-17,18,19,20-tetranor-13-trans-5-cis-prostadienoic acid |
| 269 | 40 | 2-(8-carboxyoct-2-cis-enyl)cyclopent-2-en-1-one | nat-15R,16R-(and ent-15S,16S)-15-hydroxy-9-oxo-15,16-trimethylene-16-(3-trifluoromethylphenoxy)-13-trans-5-cis-prostadienoic acid |
| 270 | 29a | 2-(6-carboxy-5-oxa-hexyl)-cyclopent-2-en-1-one | nat-15S,16R-(and ent-15R,16S)-15-hydroxy-3-oxa-9-oxo-15,16-trimethylene-13-trans-prostenoic acid |
| 271 | 36 | 2-(6-carboxy-5-oxa-hexyl)-cyclopent-2-en-1-one | nat-15S,16S-(and ent-15R,16R)-15-hydroxy-3-oxa-9-oxo-15,16-trimethylene-13-trans-prostenoic acid |
| 272 | 31 | 2-(6-carboxy-5-oxa-hexyl)-cyclopent-2-en-1-one | nat-(and ent)-15-hydroxy-3-oxa-9-oxo-15,16-tetramethylene-17,18,-19,20-tetranor-13-trans-prostenoic acid |
| 273 | 32 | 2-(6-carboxy-5-oxa-hexyl)-cyclopent-2-en-one | nat-(and ent)-15-hydroxy-3-oxa-9-oxo-15,16-trimethylene-17,18,19,20-tetranor-13-trans-prostenoic acid |
| 274 | 33 | 2-(6-carboxy-5-oxa-hexyl)-cyclopent-2-en-1-one | nat-(and ent)-15-hydroxy-3-oxa-9-oxo-15,16-pentamethylene-17,18,19,-20-tetranor-13-trans-prostenoic acid |
| 275 | 34 | 2-(6-carboxy-5-oxa-hexyl)-cyclopent-2-en-1-one | nat-15S,17R-(and ent-15R,17S)-15-hydroxy-3-oxa-9-oxo-15,17-dimethylene-13-trans-prostenoic acid |
| 276 | 35 | 2-(6-carboxy-5-oxa-hexyl)-cyclopent-2-en-1-one | nat-15S,17S-(and ent-15R,17R)-15-hydroxy-3-oxa-9-oxo-15,17-dimethylene-13-trans-prostenoic acid |
| 277 | 30 | 2-(6-carboxy-5-oxa-hexyl)-cyclopent-2-en-1-one | nat-(and ent)-16-hydroxy-3-oxa-9-oxo-16,17-tetramethylene-18,19,20-trinor-13-trans-prostenoic acid |
| 278 | 41 | 2-(6-carboxy-5-oxa-hexyl)- | nat-15R,16S-(and ent-15S, 16R)-15- |

TABLE VII-continued

| Example | Vinyl Iodide or Vinyl Tin of Example | Cyclopent-2-en-1-one | Product 9-oxo-prostaglandin and its diastereoisomer and ethyl ester where applicable (see hereinabove) |
|---|---|---|---|
| | | cyclopent-2-en-1-one | hydroxy-3-oxa-9-oxo-15,16-trimethylene-16-(4-fluorophenoxy)-17,18,19,20-tetranor-13-trans-prostenoic acid |
| 279 | 42 | 2-(6-carboxy-5-oxa-hexyl)-cyclopent-2-en-1-one | nat-15R,16R-(and ent-15S,16S)-15-hydroxy-3-oxa-9-oxo-15,16-trimethylene-16-(4-fluorophenoxy)-17,18,-19,20-tetranor-13-trans-prostenoic acid |
| 280 | 43 | 2-(6-carboxy-5-thia-hexyl)-cyclopent-2-en-1-one | nat-15R,16S-(and ent-15S,16R)-15-hydroxy-3-thia-9-oxo-15,16-trimethylene-16-(3-chlorophenoxy)-17,18,19,20-tetranor-13-trans-prostenoic acid |
| 281 | 44 | 2-(6-carboxy-5-thia-hexyl)-cyclopent-2-en-1-one | nat-15R,16R-(and ent-15S,16S)-15-hydroxy-3-thia-9-oxo-15,16-trimethylene-16-(3-chlorophenoxy)-17,18,19,20-tetranor-13-trans-prostenoic acid |
| 282 | 45 | 2-(6-carboxy-5-thia-hexyl)-cyclopent-2-en-1-one | nat-15S,17R-(and ent-15R,17S)-15-hydroxy-3-thia-9-oxo-15,17-trimethylene-19,20-dinor-13-trans-prostenoic acid |
| 283 | 46 | 2-(6-carboxy-5-thia-hexyl)-cyclopent-2-en-1-one | nat-15S,17S-(and ent-15R,17R)-15-hydroxy-3-thia-9-oxo-15,17-trimethylene-19,20-dinor-13-trans-prostenoic acid |
| 284 | 47 | 2-(6-carboxy-5-thia-hexyl)-cyclopent-2-en-1-one | nat-16R,17S-(and ent-16S,17R)-16-hydroxy-3-thia-9-oxo-16,17-trimethylene-20-methyl-13-trans-prostenoic acid |
| 285 | 48 | 2-(6-carboxy-5-thia-hexyl)-cyclopent-2-en-1-one | nat-16R,17R-(and ent-16S,17S)-16-hydroxy-3-thia-9-oxo-16,17-trimethylene-20-methyl-13-trans-prostenoic acid |
| 286 | 49 | 2-(6-carboxy-5-thia-hexyl)-cyclopent-2-en-1-one | nat-16R,17S-(and ent-16S,17R)-16-hydroxy-3-thia-9-oxo-16,17-trimethylene-17-(3-trifluoromethylphenoxy)-18,19,20-trinor-13-trans-prostenoic acid |
| 287 | 50 | 2-(6-carboxy-5-thia-hexyl)-cyclopent-2-en-1-one | nat-16R,17R-(and ent-16S,17S)-16-hydroxy-3-thia-9-oxo-16,17-trimethylene-17-(3-trifluoromethylphenoxy)-18,19,20-trinor-13-trans-prostenoic acid |
| 288 | 29a | 2-(6-carboxy-5-thia-hexyl)-cyclopent-2-en-1-one | nat-15S,16R-(and ent-15R,16S)-15-hydroxy-3-thia-9-oxo-15,16-trimethylene-13-trans-prostenoic acid |
| 289 | 36 | 2-(6-carboxy-5-thia-hexyl)-cyclopent-2-en-1-one | nat-15S,16S-(and ent-15R,16R)-15-hydroxy-3-thia-9-oxo-15,16-trimethylene-13-trans-prostenoic acid |
| 290 | 31 | 2-(6-carboxy-5-thia-hexyl)-cyclopent-2-en-1-one | nat-(and ent)-15-hydroxy-3-thia-9-oxo-15,16-tetramethylene-17,18,-19,20-tetranor-13-trans-prostenoic acid |
| 291 | 32 | 2-(6-carboxy-5-oxa-hexyl)cyclopent-2-en-1-one | nat-(and ent)-15-hydroxy-3-oxo-9-15,16-trimethylene-17,18,19,20-tetranor-13-trans-prostenoic acid |
| 292 | 33 | 2-(6-carboxy-5-oxa-hexyl)cyclopent-2-en-1-one | nat-(and ent)-15-hydroxy-3-oxa-9-oxo-15,16-pentamethylene-17,18,19,20-tetranor-13-trans-prostenoic acid |
| 293 | 34 | 2-(6-carboxy-5-oxa-hexyl)cyclopent-2-en-1-one | nat-15S,17R-(and ent-15R,17S)-15-hydroxy-3-oxa-9-oxo-15,17-dimethylene-13-trans-prostenoic acid |
| 294 | 35 | 2-(6-carboxy-5-oxa-hexyl)cyclopent-2-en-1-one | nat-15S,17S-(and ent-15R,17R)-15-hydroxy-3-oxa-9-oxo-15,17-dimethylene-13-trans-prostenoic acid |
| 295 | 30 | 2-(6-carboxy-5-oxa-hexyl)cyclopent-2-en-1-one | nat-(and ent)-16-hydroxy-3-oxa-9-oxo-16,17-tetramethylene-18,19,20-trinor-13-trans-prostenoic acid |
| 296 | 41 | 2-(6-carboxy-5-oxa-hexyl)cyclopent-2-en-1-one | nat-15R,16S-(and ent-15S,16R)-15-hydroxy-3-oxa-9-oxo-15,16-trimethylene-16-(4-fluorophenoxy)-17,18,19,20-tetranor-13-trans-prostenoic acid |
| 297 | 42 | 2-(6-carboxy-5-oxa-hex- | nat-15R,16R-(and ent-15S,16S)- |

TABLE VII-continued

| Example | Vinyl Iodide or Vinyl Tin of Example | Cyclopent-2-en-1-one | Product 9-oxo-prostaglandin and its diastereoisomer and ethyl ester where applicable (see hereinabove) |
|---|---|---|---|
| | | yl)cyclopent-2-en-1-one | 15-hydroxy-3-oxa-9-oxo-15,16-trimethylene-16-(4-fluorophenoxy)-17,-18,19,20-tetranor-13-trans-prostenoic acid |

EXAMPLE 293

Preparation of Ethyl nat(and ent)-9-oxo-15,16-tetramethylene-17,18,19,20-tetranor-15,13-trans-prostadienoate To a solution of 23.211 g of 1-(2-iodovinyl)-1-trimethylsilyloxycyclohexane in 23 ml of dry toluene, cooled to −40° C. under argon, is added 35.1 ml of 2.04 M n-butyllithium in hexane over 10 minutes. The resulting solution is stirred at −40° C. for 2 hours during which time a white precipitate forms. To this mixture is added 60 ml of dry ether and the mixture is warmed to 10° C. over a 20 minute period, producing a clear colorless solution. This solution is recooled to −40° C. and to it is added 34.8 ml of 2.057 M trimethylaluminum in heptane during 5 minutes. the cooling bath is removed and the solution is allowed to warm to 0° C. over a 20 minutes period during which time a white precipitate forms. The mixture is cooled to −78° C. To this mixture is added, over a 5 minute period, 17,653 g of 2-(6-carbethoxyhexyl)cyclopent-2-en-1-one. The cooling bath is removed and the mixture is allowed to warm to room temperature, with stirring, first by hand and then mechanically as the mixture becomes more mobile. Stirring is continued overnight, producing a clear slightly reddish-orange single phase solution. This solution is poured onto 22 ml of concentrated HCl and 400 g of ice, stirred 20 minutes and extracted with ether. The organic phase is washed with water, saturated brine, dried with MgSO$_4$ and evaporated giving 38.04 g of a slightly yellowish oil. This oil is distilled to remove impurities. The pot residue (26.51 g) is dry column chromatographed (Column I) on 800 g of silica gel equilibrated with 80 g of 9:1 benzene:ethyl acetate. The column (62"×2") is eluted with 9:1 benzene:ethyl acetate and 60 ml of solvent is allowed to pass through the column. The column is cut into one inch segments. The product from cuts 41–50 (Rf 0.6–0.81, 7.55 g) is retained for further use. Cuts 24–40 (Rf 0.37–0.65, 15.86 g) is dry column chromatographed (Column II) on 800 g of silica gel equilibrated with 10% by weight of 9:1 benzene:ethyl acetate in a 58"×2" column. The column is eluted with the same solvent and 100 ml of extra solvent is passed through. The column is cut into one inch segments. The product of cuts 41–54 (Rf 0.69–0.93, 8.46 g) is retained for further use. The material from cuts 33–40 is dry column chromatographed (Column III) on 440 g of silica gel equilibrated with 10% by weight of 9:1 benzene:ethyl acetate on a 52"×1½" column. The column is eluted with the same solvent and 150 ml of extra solvent is passed through the column. The product is found in cuts 35–49 (Rf 0.65–0.94, 3.38 g). The following products are combined: Column I, cuts 41–50 (Rf 0.65–0.81, 7.55 g); Column II, cuts 41–54 (Rf 0.69–0.93 8.46 g) and Column III, cuts 35–49 (Rf 0.65–0.94, 3.38 g) giving a total of 19.39 g. This is dissolved in 450 ml of 4:2:1 acetic acid:tetrahydrofuran:water and allowed to stand for 3 minutes at room temperature. The mixture is evaporated in vacuo on a water bath at 40° C., with the aid of 200 ml of xylene giving 13.61 g of an oil. This oil is dry column chromatographed on 830 g of silica gel equilibrated with 10% by weight of 9:1 hexane:ethyl acetate in a 59"×2" column. The column is eluted with the same solvent and 600 ml of extra solvent is passed through the column. The column is monitored by U/V bands. The material in cuts 37–45 (Rf 0.61–0.76, 3.65 g) is distilled, bp 175°–180° C. giving 3.609 g of ethyl nat-(and ent)-9-oxo-15,16-tetramethylene-17,18,19,20trans-prostadienoate.

EXAMPLE 299

Preparation of nat(and ent)-9-oxo-15,16-Tetramethylene-17,18,19,20-tetranor-15,13-trans-prostadienoic Acid A mixture of 2.800 g of ethyl nat(and ent)-9-xo-15,16-tetramethylene-17,18,19,20-tetranor-15,13-trans-prostadienoate and 1.40 g of potassium hydroxide in 40 ml of 1:1 aqueous methanol is stirred at ambient temperature overnight under nitrogen. The mixture is partially evaporated in vacuo, partitioned between ether and HCl and the organic phase is washed well with water and saturated brine, dried with MgSO$_4$ and evaporated giving 2.52 g of a yellowish oil. This oil is evaporatively distilled at 200° C. giving 2.460 g of the desired product as a nearly colorless oil.

We claim:

1. An optically active compound of the formula:

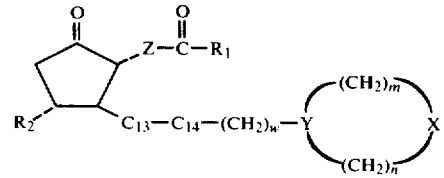

wherein R$_1$ is selected from the group hydroxy, tri-(C$_1$ to C$_4$) alkylsilyloxy and C$_1$ to C$_6$ alkoxy; R$_2$ is selected from the group hydrogen, hydroxy, tri-(C$_1$ to C$_4$) alkylsilyloxy and C$_2$-C$_5$ alkanoyloxy; Y is a trivalent radical selected from the group

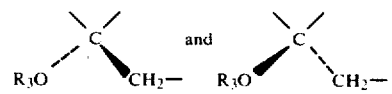

wherein R$_3$ is selected from the group hydrogen, tri-(C$_1$ to C$_4$) alkylsilyloxy and C$_2$-C$_5$ alkanoyl; X is a divalent radical selected from the group

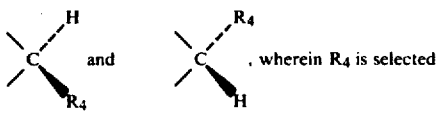

wherein R₄ is selected from the group hydrogen and $C_1$ to $C_7$ alkyl; the moiety $C_{13}$-$C_{14}$ is trans-vinylene; m and n are individually an integer of from 0 to 4 with the proviso that the sum of m and n is equal to from 2 to 4; w is zero or 1; Z is

wherein thereof; the mirror image thereof; and the pharmacologically acceptable cationic salts thereof when $R_1$ is hydrogen.

2. The compound according to claim 5, nat-15S,16S)-15-hydroxy-9-oxo-15,16-trimethylene-13-trans-5-cis-prostadienoic acid.

3. The compound according to claim 1, nat-15S,16S- (and ent-15R,16R)-15-hydroxy-9-oxo-15,16-trimethylene-13-trans-5-cis-prostadienoic acid.

4. A compound according to claim 1, wherein $R_1$, Y, X and Z are as previously defined; and $R_2$ is hydroxy.

5. The compound according to claim 4, nat-11α,15-dihydroxy-9-oxo-15,16-trimethylene-17,18,19,20-tetranor-13-trans-5-cis-prosdienoic acid.

6. The compound according to claim 4, nat-(and ent-)-11α,15-dihydroxy-9-oxo-15,16-trimethylene-17,18,19,20-tetranor-13-trans-5-cis-prosdienoic acid.

7. The compound according to claim 4, nat-11α,16-dihydroxy-9-oxo-16,17-pentamethylene-18,19,20-trinor-13-trans-5-cis-prostadienoic acid.

8. The compound according to claim 4, nat-(and ent-)-11α,16-dihydroxy-9-oxo-16,17-pentamethylene-18,19,20-trinor-13-trans-5-cis-prostadienoic acid.

9. The compound according to claim 4, nat-11α,16-dihydroxy-9-oxo-16,17-tetramethylene-18,19,20-trinor-5-cis-13-trans-protadienoic acid.

10. The compound according to claim 4, nat-(ent)-11α,16-dihydroxy-9-oxo-16,17-tetramethylene-18,19,20-trinor-5-cis,-13-trans-prostadienoic acid.

11. The compound according to claim 4, nat-15S,16R-11α,15-dihydroxy-9-oxo-15,16-trimethylene-13-trans-5-cis-prostadienoic acid.

12. The compound according to claim 4, nat-15S,16R-(and ent-15R,16S-)11α,15-dihydroxy-9-oxo-15,16-trimethylene-13-trans-5-cis-prostadienoic acid.

13. The compound according to claim 4, nat-15S,16S-11α,15-dihydroxy-9-oxo-15,16-trimethylene-13-trans-5-cis-prostadienoic acid.

14. The compound according to claim 4, nat-15S,16S- (and ent-15R,16R)11α,15-dihydroxy-9-oxo-15,16-trimethylene-13-trans-5-cis-prostandienoic acid.

15. The compound according to claim 4, nat-15R,16S-11α,15-dihydroxy-9-oxo15,16-trimethylene-13-trans-5-cis-prostadienoic acid.

16. The compound according to claim 4, nat-15R,16S-(and ent-15S,16R-)11α,15-dihydroxy-9-oxo-15,16-trimethylene-13-trans-5-cis-prostadienoic acid.

17. The compound according to claim 4, nat-15R,16R-11α,15-dihydroxy-9-oxo-15,16-trimethylene-13-trans-5-cis-prostadienoic acid.

18. The compound according to claim 4, nat-15R,16R-(and ent-15S,16S-)11α,15-dihydroxy-9-oxo-15,16-trimethylene-13-trans-5-cis-prostadienoic acid.

19. The compound according to claim 4, nat-11α,15-dihydroxy-9-oxo-15,16-tetramethylene-17,18,19,20-tetranor-5-cis-13-trans-prostadienoic acid.

20. The compound according to claim 4, nat-(and ent-)11α,15-dihydroxy-9-oxo-15,16-tetramethylene-17,18,19,20-tetranor-5-cis-13-trans-prostadienoic acid.

* * * * *